United States Patent
Stoeckius et al.

(10) Patent No.: US 12,071,656 B2
(45) Date of Patent: Aug. 27, 2024

(54) METHODS AND COMPOSITIONS FOR IDENTIFYING OR QUANTIFYING TARGETS IN A BIOLOGICAL SAMPLE

(71) Applicant: New York Genome Center, Inc., New York, NY (US)

(72) Inventors: Marlon Stoeckius, New York, NY (US); Peter Smibert, New York, NY (US); Brian Houck-Loomis, New York, NY (US)

(73) Assignee: New York Genome Center, Inc., New York, NY (US)

( * ) Notice: Subject to any disclaimer, the term of this patent is extended or adjusted under 35 U.S.C. 154(b) by 347 days.

(21) Appl. No.: 17/245,479

(22) Filed: Apr. 30, 2021

(65) Prior Publication Data

US 2021/0371914 A1    Dec. 2, 2021

Related U.S. Application Data

(63) Continuation of application No. 15/887,144, filed on Feb. 2, 2018, now abandoned.

(60) Provisional application No. 62/609,332, filed on Dec. 21, 2017, provisional application No. 62/599,450, filed on Dec. 15, 2017, provisional application No. 62/559,228, filed on Sep. 15, 2017, provisional application No. 62/549,189, filed on Aug. 23, 2017, provisional application No. 62/515,180, filed on Jun. 5, 2017, provisional application No. 62/453,726, filed on Feb. 2, 2017.

(51) Int. Cl.
| | | |
|---|---|---|
| C12Q 1/68 | (2018.01) | |
| C12N 15/10 | (2006.01) | |
| C12Q 1/6804 | (2018.01) | |
| C12Q 1/6844 | (2018.01) | |
| C40B 50/06 | (2006.01) | |

(52) U.S. Cl.
CPC ....... C12Q 1/6844 (2013.01); C12N 15/1093 (2013.01); C12Q 1/6804 (2013.01); C40B 50/06 (2013.01)

(58) Field of Classification Search
CPC ..................................................... C12Q 1/68
See application file for complete search history.

(56) References Cited

U.S. PATENT DOCUMENTS

| | | |
|---|---|---|
| 2011/0171749 A1 | 7/2011 | Alocilja et al. |
| 2015/0267191 A1 | 9/2015 | Steelman et al. |
| 2015/0307874 A1* | 10/2015 | Jaitin ................... C12Q 1/6806 506/26 |
| 2015/0376609 A1 | 12/2015 | Hindson et al. |
| 2016/0053253 A1* | 2/2016 | Salathia ............. C12N 15/1093 506/4 |
| 2018/0094313 A1 | 4/2018 | Hindson et al. |

FOREIGN PATENT DOCUMENTS

| | | |
|---|---|---|
| WO | WO 2012/106385 A2 | 8/2012 |
| WO | WO 2016/040476 A1 | 3/2016 |
| WO | WO 2016/145409 A1 | 9/2016 |

OTHER PUBLICATIONS

Applicant's Response in European Patent Application No. 18747697.3, filed Jun. 18, 2021.
Examination Report dated Sep. 8, 2022 issued in European Patent Application No. 18747697.3.
Applicant's Response in European Patent Application No. 18747697.3, filed Mar. 17, 2023.
Adler, M., et al. Sensitivity by combination: Immuno-PCR and related technologies. Analyst 133, 702-18 (Jun. 2008).
Aitchison, J., Measures of location of compositional data sets., Math. Geol. 21(7): 787-790 (1989).
Albayrak, C. et al. Digital Quantification of Proteins and mRNA in Single Mammalian Cells. Molecular Cell 61, 914-924 (Mar. 2016).
Assarsson, E., et al. Homogenous 96-plex PEA immunoassay exhibiting high sensitivity, specificity, and excellent scalability. Plos One. Apr. 2014;9:e95192.
Baranauskas, A. et al. Generation and characterization of new highly thermostable and processive M-MuLV reverse transcriptase variants, Protein Eng. Des. Sel. 25, 657-668 (Jun. 2012).
Baumgarth, N., Roederer, M. A practical approach to multicolor flow cytometry for immunophenotyping. J Immunol Methods 243, 77-97 (2000).
Bendall, S. C. & Nolan, G. P. From single cells to deep phenotypes in cancer. Nat Biotechnol 1-9 (2012) doi:10.1038/nbt.2283.
Bendall, S.C. et al, A Deep Profiler's Guide to Cytometry, Trends Immunol. Jul. 2012; 33(7):323-332.
Blondel, V.D., et al. Fast unfolding of communities in large networks, J. Stat. Mech. : Theory and Experiment, Mar. 2008, 10: 10008-19.

(Continued)

*Primary Examiner* — Amy M Bunker
(74) *Attorney, Agent, or Firm* — Howson & Howson LLP

(57) ABSTRACT

Compositions, kits and methods are described that comprise one or more constructs, each construct comprising a ligand attached or conjugated to a polymer construct, e.g., an oligonucleotide sequence, by a linker, each ligand binding specifically to a single target located in or on the surface of a cell. The polymer construct comprises a) an Amplification Handle; b) a Barcode that specifically identifies a single ligand; c) an optional Unique Molecular Identifier that is positioned adjacent to the Barcode on its 5' or 3' end; and d) an Anchor for hybridizing to a complementary sequence, e.g., for generation of a double-stranded oligonucleotide. These compositions are used in methods, including high throughput methods, for detecting one or more targets or epitopes in a biological sample. These compositions are also used in a high throughput method for characterizing a cell by simultaneous detection of one or more epitopes located in or on the cell and its transcriptome.

8 Claims, 10 Drawing Sheets

Specification includes a Sequence Listing.

(56) References Cited

OTHER PUBLICATIONS

Breton, G., et al. Defining human dendritic cell progenitors by multiparametric flow cytometry, Nat. Protoc. 10(9): 1407-1422 (Sep. 2015).
Butler, A. & Satija, R. Integrated analysis of single cell transcriptomic data across conditions, technologies, and species. bioRxiv (Jul. 2017). doi: 10.1101/164889.
Cannon, L, Mar. 2017, Single Cell Analysis: A Mini-Report, Life Science Network, p. 1-7 (Mar. 2017) http://lifesciencenetwork.com/blogs/leah- cannon/2017/03/21/single-cell-analysis-a-mini-report.
Cao, Junyue, et al. Comprehensive single cell transcriptional profiling of a multicellular organism by combinatorial indexing. Science, 357(6352):661-667 (Aug. 2017).
Chattopadhyay, P. K. & Roederer, M. Cytometry: Today's technology and tomorrow's horizons. Methods 57(3): 251-258 (Jul. 2012).
Crosetto, N et al.,. Spatially resolved transcriptomics and beyond. Nature Reviews Genetics 16.1 (Jan. 2015): 57-66.
Darmanis, S. et al. Simultaneous Multiplexed Measurement of RNA and Proteins in Single Cells. CellReports 14, 380-389 (Jan. 2016).
Delley, C. L., et al. Combined aptamer and transcriptome sequencing of single cells. Sci. Reports, 8:2919 (Feb. 2018); previously published bioRxiv 1-10 (Dec. 2017). doi:10.1101/228338.
Dezfouli, M et al., Parallel barcoding of antibodies for DNA-Assisted Proteomics, Proteomics, Sep. 2014 14:2432-2436.
Fakruddin, Md, et al. "Nucleic acid amplification: Alternative methods of polymerase chain reaction." Journal of Pharmacy and Bioallied Sciences, 5(4):245-52 (Oct. 2013).
Fan, H.C., et al., Combinatorial labeling of single cells for gene expression cytometry, Science 347 (6222):1258367 (Feb. 2015).
Ferlazzo, G. & Münz, C. J., NK Cell Compartments and Their Activation by Dendritic Cells, J. Immunol. 172, 1333-1339 (Feb. 2004).
Frei, A. P. et al. Highly multiplexed simultaneous detection of RNAs and proteins in single cells. Nature Methods 13(3): 269-275 (Mar. 2016).
Genshaft, A. S. et al. Multiplexed, targeted profiling of single-cell proteomes and transcriptomes in a single reaction. Genome Biol. 17:188 (Sep. 2016). doi:10.1186/s13059-016-1045-6.
Gierahn, T.M. et al. Seq-Well: portable, low-cost RNA sequencing of single cells at high throughput, Nat. Methods 14, 395-398 (Apr. 2017; epub Feb. 13, 2017).
Grün, D. et al. Conservation of mRNA and Protein Expression during Development of C. elegans. Cell Reports 6, 565-577 (Feb. 2014).
Gullberg, M. et al. A sense of closeness: protein detection by proximity ligation. Current Opinion in Biotechnology 14, 82-86 (2003).
Heise, C. and Bier, FF. Immobilization of DNA on microarrays. Immobilization of DNA on Chips II. Springer Berlin Heidelberg, 2005. 1-25.
Hermanson, G.T. Bioconjugation Techniques. 2nd Edition. Academic Press, San Diego, CA (2008).
Hicks, S. C., et al. Missing data and technical variability in single-cell RNA-sequencing experiments. Biostatistics (2017). doi: 10.1093/biostatistics/kxx053.
Hulspas, R. Titration of fluorochrome-conjugated antibodies for labeling cell surface markers on live cells. Curr Protoc Cytom Chapter 6, Unit 6.29 (2010).
Iglesias-Ussel, M. et al. Isolation of microarray-quality RNA from primary human cells after intracellular immunostaining and fluorescence-activated cell sorting. Journal of Immunological Methods 391.1 (May 2013): 22-30.
Islam, Saiful, et al. Quantitative single-cell RNA-seq with unique molecular identifiers. Nature methods 11.2 (Feb. 2014): 163-166.
Kang, H.M. et al., Multiplexing droplet-based single cell RNA-sequencing using natural genetic barcodes, bioRxiv 118778; doi: https://doi.org/10.1101/118778 (Mar. 2017).
Karaiskos, N. et al. The *Drosophila* embryo at single-cell transcriptome resolution. Science. Oct. 13, 2017;358(6360):194-199. doi: 10.1126/science.aan3235. Epub Aug. 31, 2017.
Klein, A. M. et al. Droplet Barcoding for Single-Cell Transcriptomics Applied to Embryonic Stem Cells. Cell 161, 1187-1201 (May 2015).
Krutzik, P. O. & Nolan, G. P. Fluorescent cell barcoding in flow cytometry allows high throughput drug screening and signaling profiling. Nat Meth 3, 361-368 (2006).
Lai, L., et al. A CD45-based barcoding approach to multiplex mass-cytometry (CyTOF). Cytometry 87A, 369-374 (Feb. 2015).
Lai, Shujing, et al. Mapping Human Hematopoietic Hierarchy At Single Cell Resolution By Microwell-seq. bioRxiv (Apr. 2017): 127217.
Lake, B. B. et al. A comparative strategy for single-nucleus and single-cell transcriptomes confirms accuracy in predicted cell-type expression from nuclear RNA. Scientific Reports 7:6031 (Jul. 2017). doi: 10.1038/s41598-017-04426-w.
Lambert, DG. Drugs and Receptors, Continuing Education in Anaesthesia Critical Care & Pain, vol. 4, Issue 6, 181-184, Dec. 1, 2004.
Levine, J. H. et al. Data-Driven Phenotypic Dissection of AML Reveals Progenitor-like Cells that Correlate with Prognosis. Cell 162(1):184-197 (Jul. 2015).
Li, Zhenhua, et al. DNA nanostructure-based universal microarray platform for high-efficiency multiplex bioanalysis in biofluids. ACS Applied Materials & Interfaces, 6(20 2): 17944-17953 (Sep. 2014).
Lizardi, P.M., et al. Mutation detection and single-molecule counting using isothermal rolling-circle amplification. Nat Genet. 1998;19:225-232.
Macosko, E. Z. et al. Highly Parallel Genome-wide Expression Profiling of Individual Cells Using Nanoliter Droplets. Cell 161(5), 1202-1214 (May 2015).
Mortazavi, A. et al. Mapping and quantifying mammalian transcriptomes by RNA-seq. Nature Methods 5, 621-628 (2008).
Murphy, K., Travers, P. & Walport, M. Janeway's Immunobiology 7th ed. (Garland Publishing, 2008).
Nimse, SB et al. Immobilization techniques for microarray: challenges and applications. Sensors 14: 22208-22229 (Nov. 2014).
Paul, F. et al. Transcriptional Heterogeneity and Lineage Commitment in Myeloid Progenitors. Cell 163, 1663-1677 (Dec. 2015).
Peterson, VM et al., Multiplexed quantification of proteins and transcripts in single cells, Nature Biotech. 35:936-939 (Aug. 2017).
Picelli, Simone. Single-cell RNA-sequencing: The future of genome biology is now. RNA Biology, 14(5):637-650 (May 2017).
Poli, A. et al., CD56bright natural killer (NK) cells: an important NK cell subset, Immunology 126(4): 458-465 (Apr. 2009).
Pontén, F. et al. A global view of protein expression in human cells, tissues, and organs. Mol Syst Biol 5, 337 (Dec. 2009).
Poulin, Jean-Francois, et al. Disentangling neural cell diversity using single-cell transcriptomics. Nat Neurosci. Aug. 26, 2016;19(9):1131-41.
Regev, A. et al. Science Forum: The Human Cell Atlas. eLife 6, e27041 (2017).
Renard, P. et al, Development of a sensitive multi-well colorimetric assay for active NFkB, Nucl. Acids Res., Feb. 2001, 29(4):e21.
Robinson, J.P. & Roederer, M., Flow Cytometry Strikes Gold, Science 350, 739-740 (2015).
Roloff, A and Seitz, O., Evolution of Synthetic Polymers., Artificial DNA: PNA & XNA 1:2, 61-63; Oct./Nov./Dec. 2010; © 2010 Landes Bioscience.
Rosenberg, Alexander B., et al. Scaling single cell transcriptomics through split pool barcoding. bioRxiv (Feb. 2017): 105163; also published in Science, 360(6385):176-182 (Apr. 2018).
Roy, N et al., Dynamers: dynamic polymers as self-healing materials, Chem. Soc. Rev., (May 2015) 44:3786.
Sano, T., et al. Immuno-PCR: very sensitive antigen detection by means of specific antibody-DNA conjugates. Science, 258(5079):120-122 (Oct. 1992).
Satija, R., et al, A. Spatial reconstruction of single-cell gene expression data. Nature Biotechnology 33(5): 495-502 (May 2015).
Schwanhäusser, B. et al. Global quantification of mammalian gene expression control. Nature 473, 337-342 (2011).
Shahi, P., et al., Abseq: Ultrahigh-throughput single cell protein profiling with droplet microfluidic barcoding, Sci. Rep. 7, 44447 (Mar. 2017).

(56) References Cited

OTHER PUBLICATIONS

Shekhar, K. et al. Comprehensive Classification of Retinal Bipolar Neurons by Single-Cell Transcriptomics. Cell 166(5), 1308-1323. e30 (Aug. 2016).
Ståhlberg, A. et al. Quantitative PCR analysis of DNA, RNAs, and proteins in the same single cell. Clinical Chemistry 58(12):1682-1691 (Dec. 2012; epub Sep. 2012).
Stegle, O., Teichmann, S. A. & Marioni, J. C. Computational and analytical challenges in single-cell transcriptomics. Nature Publishing Group 16, 133-145 (2015).
Stoeckius M, et al., Simultaneous epitope and transcriptome measurement in single cells, Nat Methods. Sep. 2017;14(9):865-868. doi: 10.1038/nmeth.4380. Epub Jul. 31, 2017.
Stoeckius, M. & Smibert, Cite-seq, Protocol Exchange http://dx.doi.org/10.1038/protex.2017.068 (Jul. 31, 2017).
Stoeckius, M. et al. Global characterization of the oocyte-to-embryo transition in Caenorhabditis elegans uncovers a novel mRNA clearance mechanism. The EMBO Journal 33, 1751-1766 (Jun. 2014).
Stubbington, M. J. T., et al. A. Single-cell transcriptomics to explore the immune system in health and disease. Science 358 (6359): 58-63 (Oct. 2017).
Tanay, A. & Regev, A. Scaling single-cell genomics from phenomenology to mechanism. Nature 541(7637), 331-338 (Jan. 2017).
Tsumoto, K. et al. Antigen-Antibody Binding, ELS, Wiley Online Library, p. 1-8, Dec. 14, 2016.
Tung, P.-Y. et al. Batch effects and the effective design of single-cell gene expression studies. Scientific Reports 7, 39921 (Jan. 2017).
Ullal, AV et al., Cancer cell profiling by barcoding allows multiplexed protein analysis in fine needle aspirates., Sci Transl Med. Jan. 15, 2014; 6(219): 219ra9. doi:10.1126/scitranslmed.3007361.
Van Buggenum, Jagl et al., A covalent and cleavable antibody-DNA conjugation strategy for sensitive protein detection via immuno-PCR, Sci. Reports, 6:22675, DOI: 10.1038/srep22675 (Mar. 2016).
Van Der Maaten, LJP and G.E. Hinton. Visualizing Data Using t-SNE. Journal of Machine Learning Research 9 (Nov. 2008):2579-2605.
Velten, L. et al. Human haematopoietic stem cell lineage commitment is a continuous process. Nature Cell Biology 19(4): 271-281 (Apr. 2017).
Villani, A.-C. et al. Single-cell RNA-seq reveals new types of human blood dendritic cells, monocytes, and progenitors. Science 356(6335): (Apr. 2017). doi:10.1126/science.aah4573.
Wendt, K. et al., Gene and protein characteristics reflect functional diversity of CD56dim and CD56bright NK cells., J. Leukoc. Biol. 80, 1529-1541 (Dec. 2006).
Wilson, N. K. et al. Combined Single-Cell Functional and Gene Expression Analysis Resolves Heterogeneity within Stem Cell Populations. Cell Stem Cell 16, 712-724 (Jun. 2015).
Wright, M. N. & Ziegler, A. ranger: A Fast Implementation of Random Forests for High Dimensional Data in C and R. Journal of Statistical Software 77, (2017).
Wu, Angela R., et al. Quantitative assessment of single-cell RNA-sequencing methods. Nature Methods 11(1):41-46 (Jan. 2014).
Xin, Yurong, et al. Use of the Fluidigm C1 platform for RNA sequencing of single mouse pancreatic islet cells. Proceedings of the National Academy of Sciences (Mar. 2016) 113(12):3293-3298.
Yao, Y et al., CyTOF supports efficient detection of immune cell subsets from small samples, J Immunol Methods., 415: 1-5 (Dec. 2014).
Yuan, J. & Sims, P.A. An Automated Microwell Platform for Large-Scale Single Cell RNA-Seq., Sci. Rep. 6, 33883 (Sep. 2016).
Zhang, Kai, et al. Single-cell isolation by a modular single-cell pipette for RNA-sequencing. Lab on a Chip 16.24 (2016): 4742-4748.
Zhao, Hong, et al. Cell fixation in zinc salt solution is compatible with DNA damage detection by phospho-specific antibodies. Cytometry A. Jun. 2011; 79(6): 470-476.
Zheng, G. X. Y. et al. Massively parallel digital transcriptional profiling of single cells. Nat. Commun. 8, 14049; doi: 10.1038/ncomms14049 (Jan. 2017).
International Search Report dated Apr. 25, 2018 in corresponding International Patent Application No. PCT/US2018/16587.
Written Opinion dated Apr. 25, 2018 in corresponding International Patent Application No. PCT/US2018/16587.
Extended European Search Report dated Nov. 23, 2020 issued in corresponding European Patent Application No. 18747697.3.
Extended European Search Report for European Patent Application No. 23203416.5, dated Apr. 30, 2024.

\* cited by examiner

Probe for ubiquitous cell surface protein:
Integrin Beta-1 (CD29)

- Anti-Mouse CD29 – Barcoded oligo 1

- Anti-Human CD29 – Barcoded oligo 2

SAV = streptavidin-biotin linkage
Direct-link = covalent bond using iEDDA chemistry

METHODS AND COMPOSITIONS FOR IDENTIFYING OR QUANTIFYING TARGETS IN A BIOLOGICAL SAMPLE

CROSS-REFERENCE TO RELATED APPLICATIONS

This application is a continuation of U.S. patent application Ser. No. 15/887,144, filed Feb. 2, 2018, now abandoned, which claims the benefit of U.S. Provisional Patent Application No. 62/453,726, filed Feb. 2, 2017, US Provisional Patent Application No. 62/515,180, filed Jun. 5, 2017, U.S. Provisional Patent Application No. 62/549,189, filed Aug. 23, 2017, U.S. Provisional Patent Application No. 62/559,228, filed Sep. 15, 2017, U.S. Provisional Patent Application No. 62/599,450, filed Dec. 15, 2017, and U.S. Provisional Patent Application No. 62/609,332, filed Dec. 21, 2017, each of which is incorporated by reference in its entirety.

STATEMENT REGARDING FEDERALLY SPONSORED RESEARCH OR DEVELOPMENT

This invention was made with government support under Grant Nos. R21-HG-009748 awarded by the National Institutes of Health. The government has certain rights in this invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "NYG_LIPP35US_ST25.txt", dated Jan. 23, 2018 and contains 11 kB.

BACKGROUND OF THE INVENTION

The ability to characterize individual cells in a heterogeneous population is becoming increasingly important in biological research and clinical diagnostics. The unbiased and high-throughput nature of modern single cell RNA-seq (scRNA-seq) approaches has proven invaluable for describing heterogeneous cell populations[1-3]. Prior to single-cell genomics, cellular states were routinely described using curated panels of fluorescently labeled antibodies directed at cell-surface proteins, which are often reliable indicators of cellular activity and function[7]. Recent studies[8,9] have demonstrated the potential for coupling "index-sorting" measurements from a cell sorter with single-cell transcriptomics; this process allows immunophenotypes to be mapped onto transcriptomically derived clusters. However, massively parallel approaches based on droplet microfluidics[1-3], microwells[47,48] or combinatorial indexing[20,30] are incompatible with cytometry and therefore cannot be augmented with protein information. Targeted methods to simultaneously measure transcripts and proteins in single cells are limited in scale or can only profile a few genes and proteins in parallel[10,14].

Traditionally, most classification methods have relied on optical detection of cell-surface proteins. Downstream analysis of the sorted cells provides an additional layer of information for cellular phenotyping and characterization. With the decreasing costs of high-throughput sequencing over the past few years, a variety of laboratory methods have emerged to isolate and sequence the RNA content of single cells (single-cell RNA sequencing, scRNA-seq). Initial single-cell sequencing approaches employed Fluorescence-Activated Cell Sorting (FACS) to isolate and partition cells from a population into individual wells of a microtiter plate in order to correlate the content of their transcriptomes to the expression of specific cell-surface markers. While effective, FACS/scRNA-seq approaches suffer from relatively low throughput and from an experimental bias in that only cell types chosen a priori are sorted and sequenced. Thus, these methods are not well suited for discovery of novel cell populations or for characterizing complex tissues that require the analysis of tens of thousands of cells.

A transition from plate-based approaches to the microfluidic/nanowell methods developed by Fluidigm and Wafergen allowed researchers to scale to enormous numbers of cells, alleviate the throughput bottleneck, bypass the experimental bias encountered by FACS and automate the cell capture and library preparation processes required for scRNA-seq. The recent adoption of droplet-based microfluidic approaches like Drop-seq[1], InDrop[2], 10× Genomics[3], and an Illumina/Bio-Rad product, has allowed scRNA-seq to scale to massive number of cells. Current droplet-based microfluidic platforms produce nanoliter-sized aqueous-in-oil emulsions at rates exceeding 1,000 droplets per second. Microparticles with unique molecular Barcodes co-encapsulated with cells in droplets allow for grouping of transcripts originating from the same cell. This approach has significantly enhanced throughput by generating tens of thousands of individual single-cell reactions per experiment while achieving significant cost reductions associated with nanoliter volume reagent use. Although droplet-based advances in single-cell genomics have dramatically changed the scale of scRNA-seq experiments, these methods suffer from a key disadvantage: All droplet-based single-cell RNA-sequencing methods lose important phenotypic information other than protein levels in general or cell-surface protein expression in particular (Table 1).

Current approaches to simultaneously detect and/or measure transcripts and proteins in single cells are based on indexed cell sorting using a limited number of markers in combination with plate-based RNA-sequencine[8,9] or proximity ligation assay (PLA and its derivatives) in combination with either digital PCR[10-13], or mass cytometry[14]. These assays are limited in scale and/or can only profile a few genes and proteins in parallel (see Table 1 for comparison of different technologies).

TABLE 1

| Methods for single-cell RNA and protein profiling | | | |
|---|---|---|---|
| TECHNOLOGY | Number | | |
| (references superscripted) | TRANSCRIPTS | PROTEINS | CELLS |
| Single-cell RNA-seq (droplet based)[1, 2, 3] | >4,000 | — | >10,000 |

TABLE 1-continued

Methods for single-cell RNA and protein profiling

| TECHNOLOGY | Number | | |
|---|---|---|---|
| (references superscripted) | TRANSCRIPTS | PROTEINS | CELLS |
| CyTOF[17, 21] | — | <100 | >10,000 |
| FACS[17, 21] | — | <50 | >10,000 |
| Index-sorting RNA-seq[12, 13] | >4,000 | <50 | ~96 - hundreds |
| Wafergen ICELL8 | >4,000 | ~4 | ~1,800 |
| Fluidigm C1 | >4,000 | ~4 | ~96-~800 |
| PLA/PEA & qPCR[13, 14, 15, 16] | ~96 | ~36 | ~96 - hundreds |
| PLAYR[17] | ~20 | ~20 | >10,000 |

Although the transcriptome can serve as a detailed readout of cellular state, it has been shown that mRNA abundance is often a poor proxy for protein levels especially in developmental processes[4-6]. The expression of cell-surface markers is traditionally measured via fluorescently-labeled antibodies by cell cytometry, and complex cell populations can be characterized by the combination of markers they express. For example, elaborate maps of cell types have been determined in recent years, based on protein markers in the immune and nervous systems[7]. This led to the use of cell cytometry as a diagnostic and monitoring tool in a number of disease areas, most prominently in oncology and immunology. However, FACS-based approaches are limited in terms of the number of markers that can be assayed simultaneously and by the fact that cells chosen for analysis are biased by the selection of known surface markers.

Thus, more-efficient compositions and methods are needed for qualitative and quantitative analysis of a multitude of cellular (and other) targets for diagnostic and research applications.

SUMMARY OF THE INVENTION

In one aspect, a composition comprises a construct that comprises a ligand attached or conjugated to a polymer construct, i.e., an oligonucleotide sequence, by a linker. The ligand is designed to bind specifically to a target in a biological sample. The polymer construct, e.g., oligonucleotide sequence, comprises an Amplification Handle; a Barcode that specifically identifies the ligand, an optional Random Molecular Tag (RMT), or Unique Molecular Identifier (UMI), hereafter referred to as "UMI" that is positioned adjacent to the Barcode on its 5' or 3' end; and an Anchor for hybridization to a capture sequence that comprises a sequence complementary to the Anchor and for subsequent generation of double-stranded sequences.

In another aspect, the linker between ligant and polymer construct can be a cleavable covalent bond.

In another aspect, the composition can further contain one or more "additional" constructs, which differ in at least one of target, ligand, and Barcode, as well as UMI from any other construct in the composition. In still a further aspect, a composition comprises one or more "substantially identical" constructs. In certain embodiments, each "substantially identical" construct differs from any other reference construct (e.g., the "first" construct or an "additional" construct) in the composition only in the identity of the sequence of the optional UMI or the absence of an UMI from the reference construct.

In yet another aspect, a kit comprising one or more of the compositions and embodiments described herein, and optional reagents for performance of one or more methods.

In another aspect, a method for detecting one or more targets in a biological sample uses one or more of the compositions and constructs described herein. In one aspect, the target is a cell surface antigen or epitope and the composition contains a single construct directed to that target, i.e., a "first" construct. In another embodiment, the composition contains multiple "substantially identical" constructs, i.e., substantially identical to the "first" construct, or one or more "additional" constructs directed to different targets and with consequently different components, as described above and defined below. The method involves contacting a biological sample with one or more of the compositions described above. Additional steps involve washing to remove unbound constructs, and/or hybridizing each Anchor sequence in individual constructs to a capture sequence. Another step involves extending the capture hybridized to the Anchor sequence to copy the construct Barcode, UMI and Amplification Handle onto double-stranded sequences. The polymer construct Barcode sequences are thereafter amplified or detected to identify whether the biological sample expresses or contains a single target, one or more additional targets, or a combination of multiple targets. Alternatively, the expression level of the targets in the sample are determined by detecting the amount of the corresponding polymer construct Barcodes normalized by an amount of any UMI or the mean amount of two or more UMIs in the treated sample.

In another aspect, a method as described above includes isolating individual cells, cell fragments, or populations of cells, from the biological sample bound to one or more of the constructs directed to detect one or more targets after the washing step. Still another step involves amplifying the double-stranded sequences with primers annealed to the Amplification Handles.

In yet a further aspect, a method uses the compositions described herein for characterizing a cell by simultaneous detection of one or more epitopes located in or on the cell and/or its transcriptome. One such method comprises contacting a biological sample containing cells with one or more of the compositions described herein. In one embodiment of this method the ligands are antibodies or fragments thereof that bind specifically to targeted epitopes located in a cell or on the surface of a cell. Such a method can use the steps of the Drop-seq[1] technique, e.g., encapsulating an individual single cell bound to one or more constructs into an aqueous droplet containing a microfluidics bead. Each bead is conjugated to a capture oligonucleotide sequence. Following cell lysis, mRNAs in the cell and the construct oligonucleotide sequence anneal to the polyT sequences of the capture oligonucleotide on the bead. From the sequences annealed to the bead are generated double-stranded cDNAs containing the bead Barcode sequence and the reverse transcripts of the cellular mRNA and double-stranded DNA containing the bead Barcode sequence and the construct oligonucleotide sequence. An amplification library containing the cDNA from the cell transcripts and the DNA containing the construct oligonucleotide sequence is generated. In this method the transcriptome of the library is associated with the cell identified by the antibody on a specifically identified construct simultaneously. By using the compositions described herein the polymer construct Barcode sequences are used to identify whether the single cell expresses the target epitope. The transcriptome of the library is simultaneously associated with the cell identified as expressing the target.

In still another aspect, the constructs described above are used in a method of batch-barcoding or cell "hashtagging". An above-described construct, e.g., an antibody or any ligand that binds to a cell, conjugated or associated with an oligonucleotide sequence comprising an Amplification Handle; a Barcode that specifically identifies the ligand, an optional Random Molecular Tag (RMT), or Unique Molecular Identifier (UMI), hereafter referred to as "UMI" that that is positioned adjacent to the Barcode on its 5' or 3' end; and an Anchor, e.g., polyA sequence) as described herein is used to label every cell within a sample prior to pooling. Several samples, labeled with such constructs, are then pooled and then analyzed by use of scRNA-seq or CITE-seq methods as described herein. The constructs utilized to label every cell within a sample have a different Amplification Handle sequence than is used for the scRNA-seq or CITE-seq methods. Such multiplexing in labeling allows unequivocal determination of most doublets and the ability to control for batch effects.

In some aspects presented herein is a method for detecting a sample or target in a multiplex assay, the method comprising: a) contacting a first sample with a first construct comprising a first ligand attached to a first oligonucleotide, wherein the first ligand binds specifically to a first target, and the first oligonucleotide comprises: i) a first amplification handle, ii) a first barcode that specifically identifies the first sample, and iii) a first anchor. In some aspects the method further comprises: b) contacting a second sample with a second construct comprising a second ligand attached to a second oligonucleotide, wherein the second ligand binds specifically to a second target, and the second oligonucleotide comprises: i) a second amplification handle, ii) a second barcode that specifically identifies the second sample, and iii) a second anchor. In some embodiments the first target and the second target are the same target, and optionally, the first amplification handle and the second amplification handle are substantially identical, and optionally, the first anchor and the second anchor are substantially identical. In some aspects, the method further comprises: c) contacting the first and the second samples with a third construct comprising a third ligand attached to a third oligonucleotide, wherein the third ligand binds specifically to a third target, and the third oligonucleotide comprises: (i) a third amplification handle, (ii) a third barcode that specifically identifies the third ligand, and (iii) a third anchor. In some aspects, the method further comprises d) contacting the first and the second samples with a fourth construct comprising a fourth ligand attached to a fourth oligonucleotide, wherein the fourth ligand binds specifically to a fourth target, and the fourth oligonucleotide comprises: i) a fourth amplification handle, ii) a fourth barcode that specifically identifies the fourth ligand, and iii) a fourth anchor.

In some embodiments, the third amplification handle and the fourth amplification handle are substantially identical, and are different from the first amplification handle and the second amplification handle. In some embodiments the first anchor, the second anchor, the third anchor and the fourth anchor are substantially identical, and optionally comprise a polyA sequence of at least 10 nucleotides in length. In some embodiments the third target and the fourth target are different targets, and optionally, the third target is different than the first or second targets, and optionally, the fourth target is different than the first or second targets.

In some aspects, the method further comprises e) contacting a third sample with a fifth construct comprising a fifth ligand that binds specifically to a fifth target, wherein the fifth target is optionally the same as the first target, and the fifth ligand is attached to a fifth oligonucleotide comprising: i) a fifth amplification handle, optionally substantially the same as the first amplification handle, ii) a fifth barcode that specifically identifies the third sample, and iii) a fifth anchor, optionally substantially the same as the first anchor, and optionally comprising a polyA sequence.

In aspects, the method further comprises f) contacting the first and the second samples, and optionally additional samples with a sixth construct comprising a sixth ligand, wherein the sixth ligand binds specifically to a sixth target, and is attached to a sixth oligonucleotide comprising: i) a sixth amplification handle, optionally substantially the same as the third amplification handle, ii) a sixth barcode that specifically identifies the sixth target, and iii) a sixth anchor, optionally the same as the third anchor, and optionally comprising a polyA sequence.

In some embodiments, the first and the second samples, an optionally one or more additional samples, comprise one or more cells, and the first, second, third, fourth, fifth and sixth targets are present in, or on the surface of, at least one of the one or more cells. In some embodiments, the contacting of (a), (b), (c), (d), (e) or (f) comprises contacting the one or more cells of the first sample, the second sample, and optional additional samples with the first, second, third, fourth, fifth or sixth constructs. In some embodiments the first and the second samples, an optionally one or more additional samples, comprise one or more cell organelles, mitochondria, exosomes, liposomes, synthetic or naturally occurring vesicles, microvesicles, ectosomes, nuclei, bacteria, virus, beads, particles, microparticles, nanoparticles, macromolecules, and synthetic or naturally occurring lipid, phospholipid or membrane spheres, and the first, second, third, fourth, fifth and sixth targets are present in, or on the surface of, at least one of the one or more cell organelles, mitochondria, exosomes, liposomes, synthetic or naturally occurring vesicles, microvesicles, ectosomes, nuclei, bacteria, virus, beads, particles, microparticles, nanoparticles, macromolecules, and synthetic or naturally occurring lipid, phospholipid or membrane spheres. In some embodiments the contacting of (a), (b), (c), (d), (e) or (f) comprises contacting the one or more cell organelles, mitochondria, exosomes, liposomes, synthetic or naturally occurring vesicles, microvesicles, ectosomes, nuclei, bacteria, virus, beads, particles, microparticles, nanoparticles, macromolecules, and synthetic or naturally occurring lipid, phospholipid or membrane spheres of the first sample, the second sample, and optional additional samples with the first, second, third, fourth, fifth or sixth constructs. In some embodiments the contacting of (a) and (b), and optionally (e) takes place prior to the contacting of any one of (c), (d) or (f). In some embodiments the contacting of (c), (d) or (f) comprises contacting a mixture of the first sample, the second sample and optionally additional samples with the third, fourth or sixth constructs. In some embodiments the first, second, third, fourth, fifth or sixth ligands comprise an antibody, or antigen binding fragment thereof. In some embodiments (i) the first, second, third, fourth, fifth or sixth anchor is located 3' of the first, second, third, fourth, fifth or sixth amplification handle, respectively, and 3' of the first, second, third, fourth, fifth or sixth barcode, respectively; and optionally, (ii) the first, second, third, fourth, fifth or sixth amplification handle is located 5' of the first, second, third, fourth, fifth or sixth barcode, respectively, and 5' of the first, second, third, fourth, fifth or sixth anchor, respectively. In some embodiments, the method further comprises washing the first sample, the second sample, or a mixture of the first sample and the second sample, and optionally additional samples after any one or more of steps (a), (b), (c), (d), (e), or (f) to remove unbound constructs. In some embodiments, after (a), (b), (c), (d), (e), or (f), encapsulating a first single cell of one of the first, second, or third, samples in a first droplet comprising a first bead conjugated to a plurality of a first capture oligonucleotide comprising, from 5' to 3', a seventh amplification handle, a seventh barcode identifying the first bead, and a sequence complementary to the first, second, third, fourth, fifth or sixth Anchor sequence, and optionally encapsulating a second single cell of one of the first, second, or third samples in a second droplet comprising a second bead conjugated to a plurality of a second capture oligonucleotide comprising, from 5' to 3', the seventh amplification handle, an eighth barcode identifying the second bead, and a sequence complementary to the first, second, third, fourth, fifth or sixth Anchor sequence. In some embodiments, the method further comprises lysing the first and second single cells thereby providing a first lysate encapsulated in the first droplet and a second lysate encapsulated in the second droplet, wherein the first and second lysates optionally comprise mRNA. In some embodiments, the method further comprises contacting the lysate of the first and second cells with a polymerase. In some embodiments, the method further comprises generating cDNA and double stranded oligonucleotide sequences of the first, second, third, fourth, fifth or sixth oligonucleotides.

In some aspects, presented herein is a method for detecting one or more targets in a biological sample, the method comprising contacting the biological sample with one or more of: a) a composition comprising a first construct that comprises a first ligand attached or conjugated to a polymer construct by a linker, said first ligand binding specifically to a first target, and said polymer construct comprising: an Amplification Handle; a Barcode that specifically identifies said first ligand; an optional Unique Molecular Identifier that is positioned adjacent to the Barcode on its 5' or 3' end; and an Anchor for hybridizing to a capture sequence that comprises a sequence complementary to said Anchor; b) a composition comprising at least one additional construct, which construct comprises an additional ligand attached or conjugated to an additional polymer construct by a linker, said additional ligand binding specifically to an additional target, and said additional polymer construct comprising an Amplification Handle; an additional Barcode that specifically identifies said additional ligand; an optional additional Unique Molecular Identifier that is positioned adjacent to the additional Barcode on its 5' or 3' end, and an Anchor for hybridizing to a capture sequence that comprises a sequence complementary to said Anchor; and c) a composition comprising one or more substantially identical constructs, each substantially identical construct differing from any other reference first or additional construct in the sequence of its optional Unique Molecular Identifier (UMI) or the absence of the UMI.

In some aspects, presented herein is a high-throughput method for detecting one or more epitopes in a biological sample, the method comprising contacting a biological sample with one or more of (i) a composition comprising a first construct that comprises a first antibody or fragment thereof that binds specifically to a first epitope, said first antibody or fragment attached or conjugated to a first polymer construct by a linker, wherein the first polymer construct comprises: an Amplification Handle; a Barcode Sequence that specifically identifies said first antibody or fragment from any other antibody or fragment that recognizes a different epitope, an optional Unique Molecular Identifier sequence that is positioned adjacent to the 5' or 3' end of the Barcode, and an Anchor sequence for hybridizing to a capture sequence that comprises a sequence complementary to said Anchor; (ii) a composition of (i) comprising at least one additional construct, which comprises an additional antibody or fragment thereof attached or conjugated to an additional polymer construct by a linker, said additional antibody or fragment thereof binding specifically to an additional epitope, and said additional polymer construct comprising: an Amplification Handle; an additional Barcode that specifically identifies said additional antibody or fragment thereof; an optional additional Unique Molecular Identifier that is positioned adjacent to the 5' or 3' end of the additional Barcode, and an Anchor sequence of (i), wherein said additional construct differs from any other construct in the composition in its antibody, epitope, Barcode, and UMI; and (iii) a composition of (i) or (ii) comprising one or more substantially identical constructs, each substantially identical construct differing from any other reference first or additional construct in the sequence of its optional Unique Molecular Identifier (UMI) or the absence of the UMI.

In some aspects, presented herein is a method for detecting at least two targets in at least a first and a second sample, the method comprising: a) contacting the first sample with a first construct comprising a first ligand attached to a first oligonucleotide, wherein the first ligand binds specifically to a first target, and the first oligonucleotide comprises: i) a first amplification handle, ii) a first barcode that specifically identifies the first sample, and iii) an anchor comprising a polyA sequence; b) contacting the second sample with a second construct comprising the first ligand attached to a second oligonucleotide, wherein the second oligonucleotide comprises: i) the first amplification handle, ii) a second barcode that specifically identifies the second sample, and iii) the anchor; c) contacting the first and the second samples with a third construct comprising a second ligand attached to a third oligonucleotide, wherein the second ligand binds specifically to a second target, and the third oligonucleotide comprises: (i) a second amplification handle, (ii) a third barcode that specifically identifies the second ligand, and (iii) the anchor; and d) contacting the first and the second samples with a fourth construct comprising a third ligand attached to a fourth oligonucleotide, wherein the third ligand binds specifically to a third target, and the fourth oligonucleotide comprises: i) the second amplification handle, ii) a fourth barcode that specifically identifies the third ligand, and iii) the anchor.

In some aspects, presented herein is a kit comprising: a) a first construct comprising a first ligand attached to a first oligonucleotide, wherein the first ligand binds specifically to a first target, and the first oligonucleotide comprises: i) a first amplification handle, ii) a first unique barcode configured to specifically identify a first sample, and iii) an anchor comprising a polyA sequence; b) a second construct comprising the first ligand attached to a second oligonucleotide, wherein the second oligonucleotide comprises: i) the first amplification handle, ii) a second unique barcode configured to specifically identify a second sample, and iii) the anchor; c) a third construct comprising a second ligand attached to a third oligonucleotide, wherein the second ligand binds specifically to a second target, and the third oligonucleotide comprises: (i) a second amplification handle, (ii) a third unique barcode configured to specifically identify the second ligand, and (iii) the anchor; and d) a fourth construct comprising a third ligand attached to a fourth oligonucleotide, wherein the third ligand binds specifically to a third target, and the fourth oligonucleotide comprises: i) the second amplification handle, ii) a fourth unique barcode configured to specifically identify the third ligand, and iii) the anchor.

In some aspects, presented herein is a composition comprising a construct comprising a ligand attached to an oligonucleotide, wherein the ligand binds specifically to a target, and the oligonucleotide comprises: i) an amplification handle, ii) a unique barcode configured to specifically identify a first sample, and iii) an anchor, optionally comprising a polyA sequence.

In still another aspect, the methods described herein are high throughput methods and employ other known detection and sequencing techniques.

Other aspects and advantages of these compositions and methods are described further in the following detailed description of the preferred embodiments thereof.

BRIEF DESCRIPTION OF THE DRAWINGS

FIG. 1A is an illustration showing an embodiment of a construct described herein in which antibodies (ligands) are linked to a polymer construct, which in this embodiment is an oligonucleotide sequence a disulfide bridge (linker) and containing functional sequence components (Amplification Handle and PCR handle) and a unique antibody identifier Barcode followed by a polyA tail (Anchor).

FIG. 1B is an illustration showing that Drop-seq beads are microparticles containing the polymer construct oligonucleotide sequence(s) with the functional features of Amplification Handle (PCR handle), a unique cell Barcode, followed by a unique molecular identifier (UMI) and a polyT tail (Anchor).

FIG. 1C is a schematic diagram of an embodiment of the CITE-seq protocol. Cells are incubated with antibodies (1), washed (2) and passed through a microfluidic chip where a single cell and one bead is encapsulated in a droplet (3) and (4). After cell lysis (5), mRNAs and antibody-oligonucleotide constructs bind to Drop-seq beads (6). Reverse transcription and template switch is performed in bulk after droplet emulsion breakage (7). After SMART PCR, full length cDNA (8a) and antibody-oligo construct products (8b) can be separated by size and amplified independently.

FIG. 2A is a gel electrophoresis result as well as illustrations of the detected molecules. Antibody-oligo complexes (1) appear as high molecular weight smear on agarose gel and can be cleaved by reducing the disulfide bond (2).

FIG. 2B are graphs illustrating two antibody-oligos. Anti-Mouse Integrin Beta-1 (CD29) antibodies are linked to Barcoded oligo 1 containing a disulfide bridge linker, an Amplification Handle (also referred to as common sequence or PCR handle), a unique antibody identifier Barcode (5'-ATGTCCT-3') and a UMI containing 4 nt followed by a polyA tail (top panel). Anti-human CD29 antibodies are linked to Barcoded oligo 2 containing a disulfide bridge, a common sequence (Amplification Handle, PCR handle), a unique antibody identifier Barcode (5'-GCCATTA-3') and a UMI containing 4 nt followed by a polyA tail (bottom panel).

FIG. 2C are results of gel electrophoresis and capillary electrophoresis trace of the full length cDNAs and oligos derived from the antibody-oligos. After reverse transcription and SMART PCR, two distinct product populations can be observed (right panel). These can be size separated into full length cDNAs (top panel, capillary electrophoresis trace) and antibody-oligo product (bottom panel) and amplified independently.

FIG. 2D is a dot plot showing the readout from RNA-seq as well as mouse and human antibody specific oligo sequences obtained in the same sequencing run. Human and mouse cells were incubated with oligo-tagged-antibodies specific for human or mouse cell surface markers (integrin beta, CD29). Cells were then passed through the Drop-seq workflow at higher concentration to allow for multiple cell encapsulation. Species in each droplet (dots on scatterplot) were then determined by mRNA sequencing (human RNA: circled by a solid line except for a small number of outliers; mouse RNA: circled by a dashed line except for a small number of outliers; mixed species RNA: rest of the dots except some outliers mentioned above).

FIG. 2E is a dot plot showing the primary classification of counted cells by sequencing mRNA and cDNAs generated therefrom. Dots represented human cells and mouse cells are labelled by a solid circle and a dashed circle respectively.

FIG. 6A is a schematic overview of sample multiplexing by cell hashing. Cells from different samples are incubated with DNA-barcoded antibodies recognizing ubiquitous cell surface proteins. Distinct barcodes (referred to as 'hashtag'-oligos, HTO), on the antibodies allow pooling of multiple samples into one single cell RNA-sequencing experiment. After sequencing, cells can be classified to their sample of origin based on HTO levels.

FIG. 6B is a representative scatter plot showing raw counts for HTO A and HTO B, across all cell barcodes. Both axes are clipped at 99.9% quantiles to exclude visual outliers.

FIG. 6C is a heatmap of all normalized and scaled HTO levels, based on our classifications. Doublets and multiplets express more than one HTO. Negative populations contain HEK-293T and mouse NIH-3T3 cells that were spiked into the experiments as negative controls. Cells with multiple "hashtag" signals are likely doublets, and the frequency of these cells matches with expected multiplet rates for the assay described in Example 10.

FIG. 6D shows tSNE embedding of the HTO dataset. Cells are colored and labeled based on our classifications. Eight singlet clusters and all 28 cross-sample doublet clusters are clearly present.

FIG. 6E shows a distribution of RNA UMIs per cell barcode in cells that were characterized as singlets (red), doublets (violet) or negative (grey).

FIG. 6F shows a transcriptome-based clustering of single-cell expression profiles reveals distinct immune cell populations interspersed across donors. B, B cells; T, T cells; NK, natural killer cells; mono, monocytes; DC, dendritic cells; pDC, plasmacytoid dendritic cells; and plasma cells. Cells are colored based on their HTO classification (donor ID), as in FIG. 6D.

FIG. 7A shows a row-normalized "confusion matrix" comparing demuxlet and HTO classifications. Each value on the diagonal represents the fraction of barcodes for a given HTO classification that received an identical classification from demuxlet.

FIG. 7B is a count distribution of the most highly expressed HTO for groups of concordant and discordant singlets. Both groups have identical classification strength based on cell "hashing".

FIG. 7C shows that discordant singlets have lower UMI counts, suggesting that a lack of sequencing depth contributed to 'ambiguous' calls from demuxlet.

FIG. 7D are RNA UMI distributions for discordant and concordant multiplets. Only concordant multiplets exhibit increased molecular complexity, suggesting that both methods are conservatively overcalling multiplets in discordant cases.

FIG. 7E shows that demuxlet assigns lower multiplets posterior probabilities to discordant calls.

FIGS. 8A to 8C are graphs showing the results of the performance of a titration series to assess optimal staining concentrations for a panel of CITE-seq immunophenotyping antibodies. Normalized ADT counts for CD8 (FIG. 8A) CD45RA (FIG. 8B) and CD4 (FIG. 8C) are depicted for the different concentrations used per test.

FIG. 8D shows a titration curve, depicting the staining index (SI) for these three antibodies across the titration series. The signal/noise ratio for these antibodies begins to saturate at levels similar to manufacturer recommended staining concentrations typical for flow cytometry antibodies.

FIG. 8E shows that cells with low UMI counts can be distinguished from ambient RNA using HTO classifications. Classified singlets group into canonical hematopoietic populations.

FIG. 8F shows barcodes classified as "negative" do not group into clusters, and likely represent 'empty' droplets containing only ambient RNA.

DETAILED DESCRIPTION

Figure 1A:
FIGS. 1A through 1C are schematic graphs showing the CITE-seq process and components enable simultaneous detection of single-cell transcriptomes and protein markers.

Compositions described herein increase the sensitivity of a variety of assay methodologies. Use of the compositions and methods to detect multiple targets in a complex environment is highly scalable and only limited by the number of specific ligands, e.g., antibodies, that are available, as opposed to fluorescent assay methods that are limited by spectral overlap of available fluorophores. For instance, flow cytometry allows the routine measurement of up to 15 parameters per cell[17,18]. The compositions described herein which employ molecular barcoding of ligands (e.g., antibodies) allow multiplexing to virtually any number and should even outcompete mass cytometry-based parallelization (CyTOF up to 100 tags)[18].

For example, one aspect of the compositions and methods described in detail below allows for simultaneous measurement of large numbers of established antibody-based markers along with unbiased single-cell transcriptome data, on the scale of tens of thousands of cells per experiment. We refer to this technique as Cellular Indexing of Transcriptome and Epitopes by sequencing (CITE-seq), using the compositions described herein. However, other techniques may use the described compositions to enhance the study and understanding of cell types and cell populations, such as cataloging cell types in healthy individuals or studying post-transcriptional gene regulation in development and disease. The efficiency of any number of diagnostic techniques and applications for assaying various disease states can be enhanced by use of the compositions described herein. The methods and compositions described herein greatly expand the power of single-cell phenotyping by combining information from both proteins and transcripts from the same single cells at an unprecedented scale.

I. Components of the Compositions and Methods

In the descriptions of the compositions and methods discussed herein, the various components can be defined by use of technical and scientific terms having the same meaning as commonly understood by one of ordinary skill in the art to which this invention belongs and by reference to published texts. Such texts provide one skilled in the art with a general guide to many of the terms used in the present application. The definitions contained in this specification are provided for clarity in describing the components and compositions herein and are not intended to limit the claimed invention.

As used herein, the term "construct" refers to a chemically synthesized or genetically engineered assemblage that comprises a ligand attached (covalently, non-covalently, or otherwise as noted herein) to at least one polymer construct (e.g., in one embodiment, an oligonucleotide sequence) by a linker. Each polymer construct comprises several functional elements: an Amplification Handle; a Barcode that specifically identifies the attached ligand, an optional Unique Molecular Identifier that is positioned adjacent to the Barcode on its 5' or 3' end, and an Anchor for hybridizing to a capture sequence that comprises a sequence complementary to the Anchor. These components of the construct can occur in any order. In one embodiment, the components are listed 5' to 3': Ligand, Linker, Amplification Handle, Barcode, and Anchor with the UMI on either end of the Barcode. In another embodiment, the components are listed 3' to 5': Ligand, Linker, Amplification Handle, Barcode, and Anchor with the UMI on either end of the Barcode. In still other embodiments, these elements of the construct can be in any other order. In still another embodiment, a construct comprises a single ligand linked to multiple identical polymer constructs. In one embodiment, each polymer construct is directly linked to the ligand (one linkage per polymer construct). In another embodiment, the polymer constructs are linked to the ligand as concatamers (multiple polymer constructs per single ligand linkage). For example, a single ligand (i.e., a monoclonal antibody) may be linked to from 1 to 50 polymer constructs.

A single strand of a nucleic often comprises a 5' (5-prime) end and a 3' (3-prime) end. The terms 5' and 3' therefore refer to a relative position on a single strand of a nucleic acid. Accordingly, the relative position of certain elements or sequences of a nucleic acid (e.g., a handle, a barcode and an anchor) can be specified in a sequential order from 5' to 3', or alternatively from 3' to 5'. For example, a nucleic acid may include, from 5' to 3', a handle, a barcode and an anchor and may be represented as: 5'-handle-barcode-anchor-3'. In the above example, the barcode and the anchor may be referred to as being 3' of the handle. Also, in the above example, the handle and the barcode may be referred to as being 5' of the anchor. Further, the position of the handle in the above example may also be referred to as adjacent to the barcode. Similarly, the barcode may be referred to as flanked by the handle and the anchor. Accordingly, one of skill in the art would know what is meant by the positional terms 3' and 5'. Such positional language, as used herein, unless explicitly indicated otherwise, does not imply that additional nucleic acid sequences are not interposed between the reference elements. For example, in the above example, additional sequences (e.g., a UMI) may be present between the handle and the barcode.

The term "polymer" as used herein refers to any backbone of multiple monomeric components that can function to bind to the selected ligand and/or Anchor component and be utilized in a downstream assay. This assay may utilize the activity of one or more enzymes, for example reverse transcriptases, DNA or RNA polymerases, DNA or RNA ligases, etc. Such polymers or monomeric components include oligonucleotides (e.g., DNA, RNA, synthetic or recombinant DNA or RNA bases or analogs of DNA or RNA bases), peptide nucleic acids (i.e., a synthetic nucleic acid analog in which natural nucleotide bases are linked to a peptide-like backbone instead of the sugar-phosphate backbone found in DNA and RNA), locked nucleic acids (LNA; see, e.g., Grunweller A and Hartmann R K, "Locked nucleic acid oligonucleotides: the next generation of antisense agents?" BioDrugs 2007. 21(4):235-43), or polyamide polymers (see, e.g. Dervan, P B and Burli, R W, "Sequence-specific DNA recognition by polyamides", Curr. Opn Chem. Biol. 1999, 3:688-693). For simplicity and ease of understanding, throughout this specification a polymer construct or a functional component thereof (e.g., Anchor, Barcode, UMI or Amplification Handle) may also be exemplified as a specific polymer or monomeric component, such as an oligonucleotide sequence, a nucleic acid, a nucleic acid sequence, etc. However, wherever the term "oligonucleotide", "nucleic acid" or nucleotide" or a similar specific example of a monomer or polymer is used in this specification, it should also be understood to mean that the polymer construct or component may be formed of any suitable polymer as described in this paragraph.

The terms "first", "additional" and "substantially identical" are used throughout this specification as reference terms to distinguish between various forms and components of constructs. For example, a "first construct" may define a construct with certain specified components in which a single specified "first" ligand binds a specific "first" target. The "first" Barcode is specific for the first ligand; the UMI identifies only that "first" polymer construct, and the Anchor binds a specified complementary sequence. The term "additional construct" refers to a construct (e.g., a second, third or fourth construct) that differs from any other construct used in the compositions and methods defined herein in the identity of the target, ligand, and Barcode. In one embodiment, an additional construct differs from other constructs in the compositions or methods by the identity of target, ligand, Barcode, UMI and Anchor. Each additional construct comprises an additional ligand attached or conjugated to an additional polymer construct by a linker. The additional ligand binds specifically to an additional target different from that of the first target. The linker between the ligand and the additional polymer construct may be the same or different from the linker in the first construct. The additional polymer construct also differs in the identity of its functional elements. The Amplification Handle may be the same or different from that used in the first construct. However, the additional Barcode that specifically identifies the additional ligand does not identify any other ligand. The optional additional UMI that is positioned adjacent to the additional Barcode on its 5' or 3' end, is specific for the additional polymer construct. In yet another embodiment, the additional Anchor has the same or a different sequence for hybridizing to the same or a different capture complementary sequence than that to which the first Anchor binds. In one embodiment, each "additional" ligand, "additional" target, "additional" Barcode and "additional" UMI components of each additional construct differs from the corresponding component in any other construct in the described composition or method.

Accordingly, unless indicated otherwise, the terms "first", "second", "third", "fourth", "fifth", "sixth, "seventh" and "eighth", refer to an element of the invention (e.g., construct, ligand, barcode, oligonucleotide, capture oligonucleotide, bead, target, anchor, amplification handle, and the like), where the recited "first", "second", "third", "fourth", "fifth", "sixth, "seventh" and "eighth" elements may be the same or may be different.

The term "specifically binds" or "binds specifically" refers to a ligand that binds to an indicated target in preference to binding to other targets (e.g., other molecules, other peptides, or other antigens) as determined by, for example, a suitable in vitro assay (e.g., an Elisa, Immunoblot, Flow cytometry, and the like). A ligand that binds specifically to a target, displays a specific binding interaction with the target that discriminates over nonspecific binding interactions with other targets (e.g., any other protein, antigen, molecule, etc.) by about 2-fold or more, often about 10-fold or more, and sometimes about 100-fold or more, 1000-fold or more, 10,000-fold or more, 100,000-fold or more, or 1,000,000-fold or more.

The term "substantially" as used herein, means at least 75%, at least 80%, at least 90%, or at least 95%, unless explicitly indicated otherwise. In some embodiments, two or more nucleic acids are substantially identical. Two or more nucleic acids, or portions thereof that are substantially identical refers to a nucleotide sequences of the two or more nucleic acids (e.g., two or more oligonucleotides, capture oligonucleotides, anchors, amplification handles, barcodes, and the like) that share at least 75%, at least 80%, at least 85%, at least 90%, at least 95%, at least 99%, or 100% percent identity. The term "percent identical" or "percent identity" refers to sequence identity between two amino acid sequences. Identity can be determined by comparing a position in each sequence which may be aligned for purposes of comparison. When an equivalent position in the compared sequences is occupied by the same nucleotide, then the nucleic acid sequences are identical at that position. Expression as a percentage of identity refers to a function of the number of identical nucleotides, or a derivative or variant thereof, at corresponding positions (e.g., as defined by an alignment) shared by the compared sequences. Various alignment algorithms and/or programs may be used to determine percent identity, non-limiting examples of which include FASTA, BLAST, or ENTREZ. FASTA and BLAST are available as a part of the GCG sequence analysis package (University of Wisconsin, Madison, WI), and can be used with, e.g., default settings. ENTREZ is available through the National Center for Biotechnology Information, National Library of Medicine, National Institutes of Health, Bethesda, MD The term "substantially identical" construct refers to a number of constructs or components, which differ from a reference construct, e.g., the "first" construct or a specific additional construct, only in the sequence of an optional Unique Molecular Identifier or its absence from the construct. In one embodiment, each one of a substantially identical construct shares the same target, ligand, Amplification Handle, Barcode and Anchor as does the reference (first or additional) construct. In another embodiment, each one of the substantially identical constructs shares the same target, ligand, Barcode and Anchor as does the reference (first or additional) construct. In one embodiment a substantially identical construct to the "first construct" differs from the reference "first" construct in the sequence and/or presence of the UMI. In another embodiment, the substantially identical additional construct differs from the reference additional construct in the UMI and the Amplification Handle.

By the term "attachment" or "attach" as used herein to describe the interaction between the components of the constructs is meant covalent attachments or a variety of non-covalent types of attachment. Other attachment chemistries useful in assembling the constructs described herein include, but are not limited to, thiol-maleimide, thiol-haloacetate, amine-NETS, amine-isothiocyanate, azide-alkyne (CuAAC), tetrazole-cyclooctene (iEDDA) (See, e.g., reference 24 and other references therein). In one embodiment, each polymer construct is linked to the ligand by an irreversible covalent link. In another embodiment, each polymer construct is linked to the ligand by a cleavable covalent link, for example a disulfide link or a photocleavable linker.

As used herein, "target" refers to any naturally occurring or synthetic biological or chemical molecule. In one embodiment, the target refers to any biological or chemical molecule expressed on the surface of a cell. In some embodiments, a target refers to any biological or chemical molecule on the surface of, or within an exosome, a nucleus, a cellular organelle, a virus or a bacteria. In certain embodiments, a target is a cell-surface protein. In some embodiments, a target is a cell. In some embodiments, a target is a nucleus, exosome, bacteria or phage. In another embodiment, the target refers to any biological or chemical molecule expressed intracellularly. In another embodiment, the target refers to any biological or chemical molecule occurring in a naturally occurring, synthetic, recombinantly engineered or isolated library, panel, or mixture of targets. In another embodiment, the target refers to any biological or chemical molecule occurring in a biological sample. The corresponding terms "first target" and each "additional target" (e.g., a second, third, fourth target, or the like) refer to different targets. The first and additional targets may independently be selected from a peptide, a protein, an antibody or antibody fragment, an affibody, a ribonucleic acid sequence or deoxyribonucleic acid sequence, an aptamer, a lipid, a polysaccharide, a lectin, or a chimeric molecule formed of multiples of the same or different targets. In the examples below, the targets are cell surface antigens or epitopes.

In some embodiments, a sample is a biological sample. As used herein, a "biological sample" as used in the methods described herein refers to a naturally-occurring sample or deliberately designed or synthesized sample or library containing one or more selected targets. In one embodiment, a sample contains a population of cells or cell fragments, including without limitation cell membrane components, exosomes, and sub-cellular components. The cells may be a homogenous population of cells, such as isolated cells of a particular type, or a mixture of different cell types, such as from a biological fluid or tissue of a human or mammalian or other species subject. Still other samples for use in the methods and with the compositions include, without limitation, blood samples, including serum, plasma, whole blood, and peripheral blood, saliva, urine, vaginal or cervical secretions, amniotic fluid, placental fluid, cerebrospinal fluid, or serous fluids, mucosal secretions (e.g., buccal, vaginal or rectal). Still other samples include a blood-derived or biopsy-derived biological sample of tissue or a cell lysate (i.e., a mixture derived from tissue and/or cells). Other suitable tissue includes hair, fingernails and the like. Still other samples include libraries of antibodies, antibody fragments and antibody mimetics like affibodies. Such samples may further be diluted with saline, buffer or a physiologically acceptable diluent. Alternatively, such samples are concentrated by conventional means. Still other samples can be synthesized or engineered collections of chemical molecules, proteins, antibodies or any other of the targets described herein. A sample is often obtained from, or derived from a specific source, subject or patient. In some embodiments, a sample is often obtained from, derived from, or associated with a specific experiment, lot, run or repetition. Accordingly, in certain embodiments, each of a plurality of samples (e.g., samples derived from different sources, different subjects, or different runs, for example) can be identified and/or differentiated using a method or composition described herein. In some embodiments, a sample is detected, tracked, tagged and/or identified by a method of hashtagging described herein. In some embodiments, the presence, amount or absence of a sample is determined by a method of hashtagging described herein. In certain embodiments, a target (e.g., a cell, nucleus, protein, etc.) that is derived from a specific sample, or source, is detected, tracked, tagged and/or identified by a method of hashtagging described herein.

In certain embodiments, a sample comprises one or more organelles, mitochondria, exosomes, liposomes, synthetic or naturally occurring vesicles, microvesicles, ectosomes, nuclei, bacteria, virus, phage, beads, particles, microparticles, nanoparticles, macromolecules, synthetic or naturally occurring lipids or membranes, phospholipid membranes, membrane spheres, the like, or combinations thereof. In some embodiments, a sample comprises one or more cells. In some embodiments, a sample comprises one or more nuclei. One or more targets may be present in, or on the surface of, or covalently or non-covalently attached to, an organelle, mitochondria, exosomes, liposome, a synthetic or naturally occurring vesicle, a microvesicle, a macrovesicle, an ectosome, a nuclei, a bacteria, a virus, a phage, a bead, a particle, a microparticle, a nanoparticle, a macromolecule, a synthetic or naturally occurring lipid membrane, a phospholipid membrane, or a membrane or lipid sphere.

The "ligand" used in these compositions and methods refers to any naturally occurring or synthetic biological or chemical molecule which is used to bind specifically to a single identified target. The binding can be covalently or non-covalent, i.e., conjugated or by any known means taking into account the nature of the ligand and its respective target. The terms "first ligand" and "additional ligand" refer to ligands that bind to different targets or different portions of a target. For example, multiple "first ligands" bind to the same target at the same site. Multiple additional ligands bind to a target different than the first ligand and different than any additional ligand. A ligand (e.g., a first ligand, and additional ligands, e.g., a second, third, fourth and fifth ligands, etc.) may independently be selected from a peptide, a protein, an antibody or antibody fragment (e.g., an antigen binding portion of an antibody), an antibody mimetic, an affibody, a ribo- or deoxyribo-nucleic acid sequence, an aptamer, a lipid, a polysaccharide, a lectin, or a chimeric molecule formed of multiples of the same or different ligands. Additional non-limiting examples of a ligand include a Fab, Fab', F(ab')2, Fv fragment, single-chain Fv (scFv), diabody (Dab), synbody, nanobodies, BiTEs, SMIPs, DARPins, DNLs, Duocalins, adnectins, fynomers, Kunitz Domains Albu-dabs, DARTs, DVD-IG, Covx-bodies, peptibodies, scFv-Igs, SVD-Igs, dAb-Igs, Knob-in-Holes, triomAbs, the like or combinations thereof. In some embodiments, a ligand is a recombinant or naturally occurring protein. In certain embodiments, a ligand is a monoclonal or polyclonal antibody, or fragment thereof. In one embodiment, the ligand(s) of the constructs can also be directly labeled with one or more detectable labels, such as fluorophores (see labels discussed below) that can be measured by methods independent of the methods of measuring or detecting the polymer construct described otherwise herein.

An antibody fragment or antigen binding fragment of an antibody refers to a portion of an antibody that binds specifically to a target and may include a Fab, Fab', F(ab')2, Fv fragment, single-chain Fv (scFv), scFv-Igs, and other fragments or portions of an antibody that can bind specifically to a target.

As used herein, the term "detectable label" means a reagent, moiety or compound capable of providing a detectable signal, depending upon the assay format employed. A label may be associated with the construct as a whole, or with the ligand only, or with the polymer construct or a functional portion thereof. Alternatively, different labels may be used for each component of the construct. Such labels are capable, alone or in concert with other compositions or compounds, of providing a detectable signal. In one embodiment, the labels are desirably interactive to produce a detectable signal. Most desirably, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength. Still other label systems that may be utilized in the described methods and constructs are detectable by other means, e.g., colored latex microparticles (Bangs Laboratories, Indiana) in which a dye is embedded may be used in place of enzymes to provide a visual signal indicative of the presence of the labeled ligand or construct in applicable assays. Still other labels include fluorescent compounds, fluorophores, radioactive compounds or elements. In one embodiment, a fluorescent detectable fluorochrome, e.g., fluorescein isothiocyanate (FITC), phycoerythrin (PE), allophycocyanin (APC), coriphosphine-O (CPO) or tandem dyes, PE-cyanin-5 or -7 (PC5 or PC7)), PE-Texas Red (ECD), PE-cyanin-5.5, rhodamine, PerCP, and Alexa dyes. Combinations of such labels, such as Texas Red and rhodamine, FITC+PE, FITC+PECy5 and PE+PECy7, among others may be used depending upon assay method. The selection and/or generation of suitable labels for use in labeling the ligand and/or any component of the polymer construct is within the skill of the art, provided with this specification.

Other components of the compositions and methods described herein can also be detectably labeled. Additionally or alternatively to the labeling of the ligand, the polymer construct(s) can be labeled with one or more detectable labels, such as fluorophores and other labels defined below. The detection of these labels is performed by methods independent of the methods described herein for measurement of the polymer construct or its components. Additionally or alternatively, the ligand and polymer construct(s) can be labeled so that when assembled into the final construct, the successful assembly is detectable, such as for production of the final construct. Additionally or alternatively, in the methods described below, the capture polymer can be labeled with one or more detectable labels. Additionally or alternatively, detectable labels can be used in the methods described below, to provide indications of successful binding. For example, the substrate to which the capture polymer is immobilized can be labeled with one or more detectable labels. Additionally or alternatively, one or more detectable labels can be used to show successful binding of the capture polymer and the polymer construct. In another embodiment, the successful binding of the capture polymer to the substrate can be labeled. Additionally or alternatively, the successful association of the polymer construct and the substrate to which the capture polymer is immobilized can be labeled with one or more detectable labels. Still further, such labels can be used to indicate the successful association of the ligand and the capture polymer. Additionally or alternatively, such labels can be used to indicate the association of the ligand and the substrate to which the capture polymer is immobilized. Still other uses of the detectable labels in these methods and compositions are contemplated.

As used herein, an "antibody or fragment" is a monoclonal antibody, a synthetic antibody, a recombinant antibody, a chimeric antibody, a humanized antibody, a human antibody, a CDR-grafted antibody, a multispecific binding construct that can bind two or more targets, a dual specific antibody, a bi-specific antibody or a multi-specific antibody, or an affinity matured antibody, a single antibody chain or an scFv fragment, a diabody, a single chain comprising complementary scFvs (tandem scFvs) or bispecific tandem scFvs, an Fv construct, a disulfide-linked Fv, a Fab construct, a Fab' construct, a F(ab')2 construct, an Fc construct, a monovalent or bivalent construct from which domains non-essential to monoclonal antibody function have been removed, a single-chain molecule containing one $V_L$, one $V_H$ antigen-binding domain, and one or two constant "effector" domains optionally connected by linker domains, a univalent antibody lacking a hinge region, a single domain antibody, a dual variable domain immunoglobulin (DVD-Ig) binding protein or a nanobody. Also included in this definition are antibody mimetics such as affibodies, i.e., a class of engineered affinity proteins, generally small (~6.5 kDa) single domain proteins that can be isolated for high affinity and specificity to any given protein target.

The "linker" refers to any moiety used to attach or associate the ligand to the polymer construct/oligonucleotide sequence portion of the constructs. Thus in one embodiment, the linker is a covalent bond. In another embodiment, the linker is a non-covalent bond. In another embodiment the linker is composed of at least one to about 25 atoms. Thus in various embodiments, the linker is formed of at least 2, 3, 4, 5, 6, 7, 8, 9, 10, 11, 12, 13, 14, 15, 16, 17, 18, 19, 20, 21, 22, 23, 24 or 25 atoms. In still another embodiment, the linker is at least one to about 60 nucleic acids. Thus in various embodiments, the linker is formed of a sequence of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, up to 60 nucleic acids. In yet another embodiment, the linker refers to at least one to about 30 amino acids. Thus in various embodiments, the linker is formed of a sequence of at least 2, 3, 4, 5, 6, 7, 8, 9, 10, 11, 12, 13, 14, 15, 16, 17, 18, 19, 20, 21, 22, 23, 24, 25, 26, 27, 28, 29, up to about 30 amino acids. In still other embodiments, the linker can be a larger compound or two or more compounds that associate covalently or non-covalently. In still other embodiments, the linker can be a combination of the linkers defined herein. The linkers used in the constructs of the compositions and methods are in one embodiment cleavable. The linkers used in the constructs of the compositions and methods are in one embodiment non-cleavable. Without limitation, in one embodiment, the linker is a cleavable linker, e.g., disulfide bond or photocleavable bond. In the examples below, the exemplified linker comprises a complex of biotin bound to the construct oligonucleotide sequence by a disulfide bond, with streptavidin fused to the ligand. In another embodiment, the biotin is bound to the ligand and the streptavidin is fused to the construct oligonucleotide sequence. Although the examples shows the exemplified linker bound to the 5' end of the oligonucleotide of the construct, in other embodiments, the linker may be covalently attached or conjugated other than covalently to any oligonucleotide sequence portion of the construct. In yet another embodiment, when the ligand is a recombinant or synthesized antibody, the linker can be engineered into the antibody sequence to facilitate 1:1 coupling to the polymer construct, thereby simplifying manufacturing of the ligand, the construct and/or the polymer construct. For example a Halotag® linker can be engineered into the selected ligand (e.g., antibody) or into the polymer construct or component, for such purposes. Additionally or alternatively, the ligand is linked to the polymer construct upon production in the same cell. See, e.g., the Halotag® protocols described by Flexi® Vector Systems Technical Manual (TM254-revised 5/17), copyright 2017 by Promega Corporation; and Janssen D. B., "Evolving haloalkaline dehalogenase", Curr. Opin. Chem. Biol., 2004, 8:150-159.

The "polymer construct" or "construct oligonucleotide sequence" is the portion of the construct which is associated with the ligand. As stated above, this association can be covalent, non-covalent or by any suitable conjugation and employing any suitable linker. The polymer construct is formed by a series of functional polymeric elements, e.g., nucleic acid sequences or other polymers as defined above, each having a function as defined herein. The ligand can be attached to the construct oligonucleotide sequence at its 5' end or at any other portion, provided that the attachment or conjugation does not prevent the functions of the components of the construct oligonucleotide sequence. As discussed above, these components are for each "first" or "additional" construct oligonucleotide sequence, an Amplification Handle; a Barcode, an optional UMI and an Anchor. In general, the polymer construct can be any length that accommodates the lengths of its functional components. In one embodiment, the polymer construct is between 20 and 100 monomeric components, e.g., nucleic acid bases, in length. In some embodiments, the construct oligonucleotide sequence is at least 20, 30, 40, 50, 60, 70, 80, 90 or over 100 monomeric components, e.g., nucleic acid bases, in length.

In other embodiments, the construct oligonucleotide is 200 to about 400 monomeric components, e.g., nucleotides, in length. In one embodiment, the polymer construct is generally made up of deoxyribonucleic acids (DNA). In one embodiment, the construct oligonucleotide is a DNA sequence. In other embodiments, the construct oligonucleotide, or portions thereof, comprises modified DNA bases. Modification of DNA bases are known in the art, and can include chemically modified bases including labels. In other embodiments, the construct oligonucleotide, or portions thereof, comprises ribonucleic acid (RNA) sequences or modified ribonucleotide bases. Modification of RNA bases are known in the art, and can include chemically modified bases including labels. In still other embodiments, different portions of the construct oligonucleotide sequence can comprise DNA and RNA, modified bases, or modified polymer connections (including but not limited to PNAs and LNAs). For a description of modifications to oligonucleotides, see commercial suppliers, e.g., Integrated DNA Technologies, USA website; Custom Oligonucleotide Modifications Guide, Sigma-Aldrich, www.sigmaaldrich.com/technical-documents/articles/biology/custom-dna-oligos-modifications.html, and Modified Oligonucleotides, TriLink, www.trilinkbiotech.com/oligo/modifiedoligos.asp. As described above, in still other embodiments, the polymer construct is composed of polyamides, PNA, etc.

As used herein, the term "Amplification Handle" refers to a functional component of the construct oligonucleotide sequence which itself is an oligonucleotide or polynucleotide sequence that provides an annealing site for amplification of the construct oligonucleotide sequence. The Amplification Handle can be formed of polymers of DNA, RNA, PNA, modified bases or combinations of these bases, or polyamides, etc. In one embodiment, the Amplification Handle is about 10 of such monomeric components, e.g., nucleotide bases, in length. In other embodiments, the Amplification Handle is at least about 5 to 100 monomeric components, e.g., nucleotides, in length. Thus in various embodiments, the Amplification Handle is formed of a sequence of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 80, 91, 92, 93, 94, 95, 96, 97, 98, 99 or up to 100 monomeric components, e.g., nucleic acids. In one embodiment, when present in first or additional construct oligonucleotide sequences, the Amplification Handle can be the same or different, depending upon the techniques intended to be used for amplification. In certain embodiments, the Amplification Handle can be a generic sequence suitable as a annealing site for a variety of amplification technologies. Amplification technologies include, but are not limited to, DNA-polymerase based amplification systems, such as polymerase chain reaction (PCR), real-time PCR, loop mediated isothermal amplification (LAMP, MALBAC), strand displacement amplification (SDA), multiple displacement amplification (MDA), recombinase polymerase amplification (RPA) and polymerization by any number of DNA polymerases (for example, T4 DNA polymerase, Sulfulobus DNA polymerase, Klenow DNA polymerase, Bst polymerase, Phi29 polymerase) and RNA-polymerase based amplification systems (such as T7-, T3-, and SP6-RNA-polymerase amplification), nucleic acid sequence based amplification (NASBA), self-sustained sequence replication (3 SR), rolling circle amplification (RCA), ligase chain reaction (LCR), helicase dependent amplification (HDA), ramification amplification method and RNA-seq[23]. See, also, e.g., ref 27.

The term "Barcode" or "construct Barcode" describes a defined polymer, e.g., a polynucleotide, which when it is a functional element of the polymer construct, is specific for a single ligand. As used in the various methods described herein the term Barcode can be a "cell Barcode" or "substrate Barcode", which describes a defined polynucleotide, specific for identifying a particular cell or substrate, e.g., Drop-seq microbead. In either embodiment, the Barcode can be formed of a defined sequence of DNA, RNA, modified bases or combinations of these bases, as well as any other polymer defined above. In one embodiment, the Barcode is about 2 to 4 monomeric components, e.g., nucleotide bases, in length. In other embodiments, the Barcode is at least about 1 to 100 monomeric components, e.g., nucleotides, in length. Thus in various embodiments, the Barcode is formed of a sequence of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 80, 91, 92, 93, 94, 95, 96, 97, 98, 99 or up to 100 monomeric components, e.g., nucleic acids.

The term "Unique Molecular Identifier" (UMI), also called equivalently a "Random Molecular Tag" (RMT), is a random sequence of monomeric components of a polymer as described above, e.g., nucleotide bases, which when it is a functional element of the polymer construct, is specific for that polymer construct. The UMI permits identification of amplification duplicates of the polymer construct/construct oligonucleotide sequence with which it is associated. In the description of the methods and compositions herein, one or more UMI may be associated with a single polymer construct/construct oligonucleotide sequence. The UMI may be positioned 5' or 3' to the Barcode in the composition. In another embodiment, the UMI may be inserted into the polymer/construct oligonucleotide sequence as part of the described methods. In one embodiment of the methods described herein, depending on which RNA-sequencing method is used, a UMI is added during the method. However, not all RNA-seq methods make use of UMIs. In the example of single cell droplet RNA-sequencing described below, another UMI is introduced during reverse transcription. Each UMI is specific for its construct oligonucleotide sequence. Thus when the compositions or methods comprise multiple "first constructs", each first construct differs only in the sequence of its UMI. Each additional construct will also have its own UMI, which is not present on duplicate additional constructs or additional constructs that differ from each other in target, ligand, Barcode and Anchor specificity. Similarly as used in the various methods described herein, a UMI may be associated with a polymer, e.g., an oligo or polynucleotide sequence, used in a particular assay format or with a polymer, e.g., an oligo or polynucleotide, that is immobilized on a substrate. Each UMI for each polymer construct, e.g., oligonucleotide or polynucleotide, is different from any other UMI used in the compositions or methods. In any embodiment, the UMI is formed of a random sequence of DNA, RNA, modified bases or combinations of these bases or other monomers of the polymers identified above. In one embodiment, a UMI is about 8 monomeric components, e.g., nucleotides, in length. In other embodiments, each UMI can be at least about 1 to 100 monomeric components, e.g., nucleotides, in length. Thus in various embodiments, the UMI is formed of a random sequence of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 80, 91, 92, 93, 94, 95, 96, 97, 98, 99 or up to 100 monomeric components, e.g., nucleic acids.

As used herein, the term "Anchor" refers to a defined polymer, e.g., a polynucleotide or oligonucleotide sequence, which is designed to hybridize to another oligonucleotide sequence, e.g., a capture polymer, a capture oligonucleotide, a primer and the like. In one embodiment of the polymer construct, an Anchor is designed for the purpose of generating a double-stranded construct oligonucleotide sequence. In some embodiments, the Anchor is positioned at the 3' end of an oligonucleotide sequence (e.g., a construct oligonucleotide sequence). In other embodiments, an Anchor is positioned at the 5' end of a construct oligonucleotide sequence. In some embodiments, each Anchor is specific for its intended complementary sequence. For example, in certain embodiments, an anchor is configured to hybridize to a 3' end of a capture oligonucleotide such that the 3' end of the capture oligonucleotide acts as a primer that can generate a second complementary strand of the oligonucleotide in the presence of a polymerase. In certain embodiments, when the compositions or methods comprise multiple "first constructs", each first construct has the same Anchor sequence. In one embodiment, each additional Anchor has a different additional sequence which hybridizes to a different complementary sequence. In other embodiments, each additional Anchor may have the same Anchor sequence as the first or other constructs, depending upon the assay method steps. When used in the various methods described herein, an Anchor may hybridize to a free complementary sequence or with a complementary sequence that is immobilized on a substrate. In certain embodiments, the Anchor can be formed of a sequence of monomers of the selected polymer, e.g., DNA, RNA, modified bases or combinations of these bases, PNAs, polyamides, etc. In one embodiment, an Anchor is about 3 to 15 monomeric components, e.g., nucleotides, in length. In other embodiments, each Anchor can be at least about 3 to 100 monomeric components, e.g., nucleotides, in length. In some embodiments, an anchor comprises 3 to 100, 3 to 50, 3 to 30, 5 to 30, 10 to 20, 5 to 20, or 5 to 15 monomeric components (e.g., nucleotides in length). In various embodiments, an Anchor is formed of a sequence of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 80, 91, 92, 93, 94, 95, 96, 97, 98, 99 or up to 100 monomeric components, e.g., nucleic acids. In some embodiments, and as shown in the examples, an Anchor sequence comprises or consists of a polyA sequence. In certain embodiments, a polyA sequence comprises a nucleic acid sequence comprising ten or more (e.g., 10-40, 10-30 or 10-20) consecutive adenosine nucleotides, derivatives or variants of an adenosine nucleotide, the like, or a combination thereof. In another embodiment, an Anchor sequence comprises or consists of a polyT sequence. In another embodiment, an Anchor sequence is a polyG sequence. In still another embodiment, an Anchor sequence may be a random sequence provided that it can hybridize to its intended complementary sequence (e.g., a capture oligonucleotide, amplification primer, or the like). For example, in some embodiments a method described herein may utilize a plurality of oligonucleotides (e.g., a plurality of constructs comprising a ligand attached to an oligonucleotide), where some or all of the oligonucleotides comprise a different anchor (i.e., an anchor having a different nucleic acid sequence, or an anchor having a substantially different nucleic acid sequence). In some embodiments a method described herein may utilize a plurality of oligonucleotides (e.g., a plurality of constructs comprising a ligand attached to an oligonucleotide), where some or all of the oligonucleotides comprise the same anchor. In some embodiments a method described herein may utilize a plurality of oligonucleotides (e.g., a plurality of constructs comprising a ligand attached to an oligonucleotide), where some or all of the oligonucleotides comprise an anchor that is substantially identical (e.g., comprising a nucleic acid sequence that is substantially identical). In some embodiments a method described herein may utilize a plurality of oligonucleotides (e.g., a plurality of constructs comprising a ligand attached to an oligonucleotide), where some or all of the oligonucleotides comprise an anchor comprising a polyA sequence. In some embodiments, the polyA sequence of a plurality of anchors is substantially identical. As understood by one of skill in the art, polyA sequences that are substantially identical may differ substantially in length. In some embodiments, a polyA sequence (e.g, a polyA sequence of an anchor) is a nucleic acid configured to hybridize to a polyT sequence (e.g., an oligonucleotide or capture oligonucleotide comprising a polyT sequence). As understood by one of skill in the art, depending on hybridization conditions a polyA sequence may comprise one, two, three or four non-polyA nucleotides and still hybridize efficiently to a polyT sequence, thereby providing an annealed polyA-polyT complex comprising one, two, three or more mismatches. Accordingly, in some embodiments, a polyA sequence is a nucleic acid sequence comprising at least 70%, at least 75%, at least 80%, at least 85%, at least 90%, at least 95% or 100% adenosine nucleotides, adenosine analogs, adenosine variants or a combination thereof.

In some embodiments, an oligonucleotide comprises a polyT sequence. In some embodiments, a capture oligonucleotide comprises a polyT sequence (e.g., a 3' polyT sequence). In some embodiments a method described herein may utilize a plurality of oligonucleotides (e.g., a plurality of capture oligonucleotides), where some or all of the oligonucleotides comprise a polyT sequence. In some embodiments, a polyT sequence of a plurality of oligonucleotides is substantially identical. In some embodiments, a plurality of capture oligonucleotides (e.g., a plurality of different capture oligonucleotides, e.g., different bead-specific capture oligonucleotides) comprise a polyT sequence that is substantially identical. As understood by one of skill in the art, polyT sequences that are substantially identical may differ substantially in length. In some embodiments, a polyT sequence comprises 3 to 100, 3 to 50, 3 to 30, 5 to 30, 10 to 20, 5 to 20, or 5 to 15 consecutive nucleotides (e.g., nucleotides in length). In certain embodiments, a polyT sequence comprises a nucleic acid sequence comprising three or more, ten or more, 3 to 100, 3 to 50, 3 to 30, 5 to 30, 10 to 20, 5 to 20, or 5 to 15 consecutive thymidine nucleotides, derivatives or variants of a thymidine nucleotide, the like, or a combination thereof. In some embodiments, a polyT sequence (e.g, a polyT sequence of a capture oligonucleotide) is a nucleic acid configured to hybridize to a polyA sequence. As understood by one of skill in the art, depending on hybridization conditions, a polyT sequence may comprise one, two, three or four non-thymidine nucleotides and still hybridize efficiently to a polyA sequence, thereby providing an annealed polyA-polyT complex comprising one, two, three or more mismatches. Accordingly, in some embodiments, a polyT sequence is a nucleic acid sequence comprising at least 70%, at least 75%, at least 80%, at least 85%, at least 90%, at least 95% or 100% thymidine nucleotides, thymidine analogs, thymidine variants or a combination thereof. In some embodiments, a polyT sequence comprises one or more uracil nucleotides, or derivative thereof.

The "capture oligonucleotide" or "capture oligo" or "capture polymer" is a polymeric sequence, e.g., an oligonucleotide, comprising at least a sequence that is complementary to an Anchor. In some embodiments, the capture polymer/oligo is not part of the first or additional constructs; rather it is any polymeric sequence or oligonucleotide belonging to a construct-purification kit or an mRNA-sequencing kit. As used herein, the term "complementary sequence" refers to a sequence to which an Anchor sequence (or other nucleic acid, e.g., a primer or capture oligonucleotide) is intended to hybridize to, often resulting in a hybridized double stranded complex. In the presence of a polymerase, a hybridized complex can often be extended in a 3' direction where a nucleic acid template is present. Accordingly, in certain embodiments, a sequence complementary to an anchor can hybridize to an anchor sequence thereby providing a primer for amplification and/or to generate a double stranded sequence. In certain embodiments, the capture polymer/oligonucleotide sequence may contain sequences that can be used as Amplification Handles and optionally one or more Unique Molecular Identifiers and Barcode sequences. In the methods described below, the extension of the capture polymer/oligonucleotide with its complementary sequence hybridized to the Anchor sequence copies the Barcode, the UMI and the Amplification Handle from the first or additional constructs onto the capture polymer/oligonucleotide. In any embodiment, the capture polymer/oligonucleotide and its complementary sequence can be formed of DNA, RNA, modified bases or combinations of these bases or of any other polymeric component as defined above. Depending upon the assay steps involved and the intended target, the capture sequence can be unhindered or "free" in the biological sample. In one embodiment, the capture polymer/oligo contains a complementary sequence that is a primer sequence designed to participate in amplifying the polymer construct/construct oligonucleotide sequence. In another embodiment, the capture sequence is immobilized on a substrate. Similarly to the Anchor sequence, each capture sequence can be at least about 3 to about 100 monomeric units, e.g., nucleotides, in length. Thus in various embodiments, the capture or its complementary sequence is formed of a sequence of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 80, 91, 92, 93, 94, 95, 96, 97, 98, 99 or up to 100 monomeric units, e.g., nucleic acids. In one embodiment, and as shown in the examples, a capture oligo contains a complementary sequence polyT sequence when the Anchor sequence is a polyA sequence. In another embodiment, the capture oligo contains a polyA sequence. In still another embodiment, the complementary sequence may be a random polymer, e.g., oligonucleotide sequence, provided that it can hybridize to its intended Anchor sequence.

The terms "cell hashtagging", "cell hashing" or "hashtagging" as used synonymously herein refers to a novel method of tagging a sample, contents of a sample, or targets that are derived from the same sample or source (e.g., a sample obtained from the same subject, same patient, same lot, same run, etc.) where the sample is intended to be later mixed with a plurality of different samples for multiplexing. In some embodiments, a hashtagging method comprises contacting targets of a sample with one or more constructs comprising a unique barcode that identifies the sample. Where two or more constructs are used in a hashtagging method to tag the same sample, sometimes all of the constructs comprise the same barcode. In some embodiments, where two or more constructs are used in a hashtagging method to tag the same sample, all of the constructs comprise the same amplification handle, or amplification handles that are substantially identical. The targets used to hashtag multiple sample can be the same or different targets. In some embodiments, a first sample is tagged with a first construct, a second sample is tagged with a second construct and a third sample is tagged with a third construct, where each of the constructs are configured to bind specifically to the same target, however each of the first, second and third constructs comprise a distinguishable barcode that is substantially different. After washing away unbound constructs, the sample can be pooled for further analysis using a method described herein. The hashtagging allows for later detection, tracking and or quantitation of the each of the samples and targets that are derived from the same sample.

In some embodiments, one first construct as described above, is used to label all cells in a sample prior to pooling multiple samples of cells and prior to performing other scRNA seq or CITE-seq methods using other such constructs having different Amplification Handle sequences. Upon reverse-transcription, the oligonucleotide portions of the cell hashtag constructs are converted to "hashtags" which enable identification and assignment of each cell within a heterogeneous mixture to its respective original population. The cell-hashtag construct thus serves the purposes of identifying all the cells of a particular sample. The ligand in the cell-hashtag construct can be a pool of antibodies to broadly expressed proteins or a single antibody to such a protein, or any other cell-binding ligand. Because the Amplification Handle sequence of the cell hashtag is different from that of the first or additional construct used in the CITE-seq methods, one may follow individual cells of an identified sample through the CITE-seq methods, which are typically used to identify cells within a sample that differentially express specific cell surface proteins.

By the term "immobilized" is mean that the capture polymer/oligonucleotide sequence is attached to a solid substrate resulting in reduction or loss of mobility via physical adsorption through charge-charge interation or hydrophobic interaction, covalent bonding, Streptavidin-Biotin interation or affinity coupling. See, e.g. refs 28 and 29.

By the term "substrate" is meant a microparticle (bead), a microfluidics microparticle (bead), a slide, a multi-well plate or a chip. The substrates are conventional and can be glass, plastic or of any conventional materials suitable for the particular assay or diagnostic protocols. See, e.g. refs. 1 and 31.

The terms "a" or "an" refers to one or more. For example, "an expression cassette" is understood to represent one or more such cassettes. As such, the terms "a" (or "an"), "one or more," and "at least one" are used interchangeably herein.

As used herein, the term "about" means a variability of plus or minus 10% from the reference given, unless otherwise specified.

The words "comprise", "comprises", and "comprising" are to be interpreted inclusively rather than exclusively, i.e., to include other unspecified components or process steps.

The words "consist", "consisting", and its variants, are to be interpreted exclusively, rather than inclusively, i.e., to exclude components or steps not specifically recited.

As used herein, the phrase "consisting essentially of" limits the scope of a described composition or method to the specified materials or steps and those that do not materially affect the basic and novel characteristics of the described or claimed method or composition. Wherever in this specification, a method or composition is described as "comprising" certain steps or features, it is also meant to encompass the same method or composition consisting essentially of those steps or features and consisting of those steps or features.

For simplicity and ease of understanding, throughout this specification, certain specific examples are provided to teach the construction, use and operation of the various elements of the compositions and methods described herein. Such specific examples are not intended to limit the scope of this description.

II. The Compositions

The compositions used in the methods described herein comprise one or more of the constructs, first constructs and additional constructs, and a variety of selection of construct components as described above. The selection of the components of the composition will depend upon the identity of the target sought, the RNA sequencing and amplification protocols employed and the purpose of the assay method. In the methods section below, the exemplified methods employ Drop-seq methodologies; however, other methods may be used. The method used may dictate the selection and compositions of the various components described above which make up the composition. Thus the following description of compositions is not exhaustive, and one of skill in the art can design many different compositions based on the teachings provided herein. The composition may also contain the constructs in a suitable carrier or excipient. The elements of each composition will depend upon the assay format in which it will be employed.

In one embodiment, a composition comprises a "first" construct that comprises a "first" ligand attached or conjugated to a polymer construct, e.g., a construct oligonucleotide sequence, by a linker. In this embodiment, the construct oligonucleotide sequence comprises a) an Amplification Handle; b) a Barcode that specifically identifies the first ligand; c) an optional Unique Molecular Identifier that is positioned adjacent to the Barcode on its 5' or 3' end; and d) an Anchor (e.g., of at least 3 nucleotides) for hybridizing to a capture oligonucleotide sequence that comprises a sequence complementary to the Anchor. In one embodiment, the first ligand binds specifically to a first target located in or on the surface of a cell, such as a cell surface antigen or epitope.

In another embodiment, a composition comprises multiple substantially identical "first" constructs, wherein each substantially identical first construct differs from the reference "first" construct only in the sequence of the optional Unique Molecular Identifier or its absence from the construct. Yet another embodiment of the composition includes at least one additional construct, which comprises an additional ligand attached or conjugated to an additional construct oligonucleotide sequence by a linker, the additional ligand binding specifically to an additional target located in or on the surface of a cell, and the additional construct oligonucleotide sequence comprising: a) an Amplification Handle; b) an additional Barcode that specifically identifies the additional ligand; c) an optional additional Unique Molecular Identifier that is positioned adjacent to the additional Barcode on its 5' or 3' end, and d) an Anchor of at least 3 nucleotides for hybridizing to a complementary sequence. In one embodiment, the Amplification Handle or Anchor also differ from the corresponding components in any other construct in the composition. The components specifically identified as "additional" components differ from the corresponding components in any other construct in the composition. In another embodiment, a composition comprises multiple substantially identical "additional" constructs, wherein each substantially identical additional construct differs from the reference "additional" construct only in the sequence of the optional Unique Molecular Identifier or its absence from the construct. The number of constructs in a single composition is limited only by the number of targets desired to be identified and/or quantified.

As described in the examples below, in one specific composition, the first or additional ligand is an antibody or antibody fragment and the first or additional target is a cell surface epitope. In another specific composition, the first or additional ligand is an antibody or antibody fragment and the first or additional target is an intracellular protein. Any number of compositions may be prepared with various combinations of ligands and targets as discussed above. For example, a cell hashtag construct preferably uses a ligand that targets a broadly expressed cellular protein, based on the differences in intended use of these constructs in contrast to the CITE-seq constructs, as described herein.

In another composition, the first construct comprises a first antibody or fragment thereof attached or conjugated to a construct oligonucleotide sequence by a linker, the first antibody or fragment thereof binding specifically to a first epitope sequence located on the surface of a cell, and the construct oligonucleotide sequence comprising: an Amplification Handle; a Barcode that specifically identifies the first antibody or fragment; an optional Unique Molecular Identifier that is positioned adjacent to the Barcode on its 5' or 3' end; and a polyA Anchor sequence of at least 3 nucleotides for hybridizing to a polyT sequence. This type of composition is particularly suitable wherein the complementary polyT sequence is immobilized on a substrate, e.g., a microfluidics bead. As described in the examples below, this composition's construct contains a linker that comprises biotin, which is bound to the 5' end of the construct oligonucleotide sequence by a disulfide bond; and streptavidin, which is fused to the antibody or antibody fragment. Another composition can be designed containing multiple of these first constructs, which differ only in the sequence of the optional Unique Molecular Identifier or its absence from the construct.

In yet a further embodiment, the composition contains at least one additional construct, which comprises at least one additional antibody or fragment thereof that binds specifically to an additional epitope located in or on the surface of a cell. The additional antibody or fragment is conjugated with an additional construct oligonucleotide sequence by a linker, wherein the additional construct oligonucleotide sequence comprises from 5' to 3': an Amplification Handle; an additional Barcode Sequence that specifically identifies the additional antibody or fragment from any other antibody or fragment that recognizes an additional epitope, an optional additional Unique Molecular Identifier sequence that is positioned adjacent to the Barcode on its 5' or 3' end, and a polyA sequence of at least 3 nucleotides designed for hybridizing to a polyT sequence, wherein the additional components differ from the corresponding components in any other construct. In another embodiment, the Amplification Handle or Anchor differ from the corresponding components in any other construct in the composition.

Another exemplary specific composition contains an antibody mimetic as the first ligand and the first target is an intracellularly expressed protein that is present in a biological sample of biopsy tissue. The first construct comprises the antibody mimetic designed for binding to the target protein covalently attached to a construct oligonucleotide sequence by a linker, e.g., a disulfide linker. The construct oligonucleotide sequence comprises in 5' to 3' order: an Amplification Handle; a Barcode that specifically identifies the first antibody mimetic; a UMI is positioned adjacent to the Barcode on its 5' end; and a polyA Anchor sequence. The composition also contains one or more substantially identical first constructs, where each substantially identical first construct differs from the reference "first construct" by containing a different sequence for the UMI. In one embodiment, a substantially identical construct contains no UMI.

In yet a further exemplary embodiment, the composition contains two additional constructs. Each additional construct comprises a different antibody mimetic which specifically binds a different protein present in the biopsied tissue sample. Each of the two additional constructs comprises the antibody mimetic conjugated with its additional construct oligonucleotide sequence by a linker. Each linker can be an optional chemistry as taught above. In one such additional construct, the construct oligonucleotide sequence comprises from 3' to 5': an Amplification Handle; a Barcode Sequence that specifically identifies the additional antibody mimetic from any other antibody or fragment that recognizes a different protein target from the first constructs, and an additional different UMI sequence that is positioned adjacent to the Barcode on its 3' end, and a polyA sequence of at least 5 nucleotides designed for hybridizing to a polyT sequence. In another embodiment, the second additional construct comprises from 5' to 3': an Amplification Handle; a Barcode Sequence that specifically identifies an antibody mimetic different from those of the first constructs and from the first additional construct, and which recognizes a third protein target different from the first construct or first additional construct. This second additional construct contains no UMI but contains a polyA sequence of at least 3 nucleotides designed for hybridizing to a polyT sequence. These two additional constructs have targets, antibody mimetic ligands, Barcodes, and UMIs (if present) that differ from each other's corresponding components and differ from the corresponding components in the "first" construct and any substantially identical "first" constructs present in the composition. It should further be understood that compositions may also have one or more substantially identical additional constructs, which differ from the reference additional construct by the UMI, as described above.

Many other types of ligands, targets, samples, UMIs, and Barcodes as described above can be used to generate a wide variety of compositions as described herein.

Kits containing the compositions are also provided. Such kits will contain one or more first or additional constructs, one or more preservatives, stabilizers, or buffers, and such suitable assay and amplification reagents depending upon the amplification and analysis methods and protocols with which the composition will be used. Still other components in a kit include optional reagents for cleavage of the linker, a wash buffer, a blocking solution, a lysis buffer, and an encapsulation solution, detectable labels, immobilization substrates, optional substrates for enzymatic labels, as well as other laboratory items.

III. Methods of Use of the Compositions

The compositions and kits described above can be used in diverse environments for detection of different targets, by employing any number of assays and methods for detection or targets in general.

In one embodiment, a method for detecting one or more targets in a biological sample uses the compositions described herein. The method includes the steps of contacting the biological sample with one or more of the compositions described above. In one embodiment, the sample is contacted with a composition comprising a first construct that has a first ligand attached or conjugated to a polymer construct, e.g., a construct oligonucleotide sequence, by a linker. In one embodiment, the first ligand binds specifically to a first target located in a cell or on the surface of a cell, such as a cell surface epitope. The construct oligonucleotide sequence comprises: an Amplification Handle; a Barcode that specifically identifies the first ligand; an optional Unique Molecular Identifier that is positioned adjacent to the Barcode on its 5' or 3' end; and an Anchor for hybridizing to a complementary sequence for generation of a double stranded oligonucleotide sequence. In another embodiment, a biological sample is contacted with a composition comprising substantially identical "first" constructs, wherein each substantially identical first construct differs from the reference "first" construct only in the sequence of the optional UMI or its absence from the construct. Therefore the biological sample is contacted with multiple ligands to the same cell surface epitope target.

In still another embodiment of the method, the sample is contacted with a first construct as described above (or multiples thereof); and a composition comprising at least one additional construct. The additional ligand is covalently attached or conjugated to an additional construct oligonucleotide sequence by a linker, the additional ligand binding specifically to an additional target located in a cell or on the surface of a cell. Thus, the additional target is in one embodiment a different cell surface epitope. The additional construct oligonucleotide sequence comprising: an Amplification Handle; an additional Barcode that specifically identifies the additional ligand; an optional additional Unique Molecular Identifier that is positioned adjacent to the additional Barcode on its 5' or 3' end, and an Anchor of at least 3 nucleotides for hybridizing to a complementary sequence for generation of a double stranded oligonucleotide sequence, wherein the additional components differ from the corresponding components in any other construct in the composition. In yet another embodiment, the Amplification Handle or Anchor differ from the corresponding components in any other construct in the composition. It should be understood, that in this embodiment any number of additional constructs can be designed as described above to bind as many cell epitopes as desired, limited only by the choice and number of ligands. As described herein, in another embodiment the composition may contain one or more substantially identical "additional" constructs, wherein each substantially identical additional construct differs from the reference "additional" construct only in the sequence of the optional UMI or its absence from the construct.

In such a method, following the contacting and binding that occurs between cells in the biological sample and the first ligand in the first construct and desired number of additional ligands in the additional construct(s), the biological sample is washed to remove unbound constructs, if any. For each construct bound to its target epitope, the Anchor sequence is then hybridized to its corresponding capture oligo complementary sequence. This can occur by addition of primers as capture complementary sequences or a capture oligo complementary sequence immobilized on a substrate, such as a bead, a slide, a multi-well plate or a chip. In certain embodiments, the 5' end of the complementary sequence further comprises: an additional Amplification Handle; an additional Barcode that specifically identifies the substrate to which the capture oligo sequence is bound; and an optional additional Unique Molecular Identifier that is positioned adjacent to the additional Barcode on its 5' or 3' end that identifies each capture oligo sequence.

Once the capture oligo with its complementary sequence is present in the sample, generation of double stranded oligonucleotide sequences can occur. In certain embodiments, the method also includes optionally inserting one or more UMIs to a position adjacent to the Barcode on its 5' or 3' end or at any other portion, provided that the insertion does not prevent the functions of the components of the construct oligonucleotide sequence before or after Anchor hybridization.

The detection method, in one embodiment, includes detecting the construct Barcode sequences from each first and additional construct to identify whether the biological sample expresses or contains the first target (e.g., epitope) the additional targets (e.g., one or multiple additional cell surface epitopes) or a combination of the first target and additional targets (e.g., multiple different epitopes).

In yet another embodiment of this detection method, the expression level of the first target or additional targets in the biological sample is determined by detecting the amount of the corresponding construct Barcodes. In one embodiment, the detection is performed by normalization to the amount of any one of Unique Molecular Identifiers or the mean amount of two or more of Unique Molecular Identifiers.

Various embodiments of the methods can include adding to the biological sample the composition containing the first construct(s) only, or compositions containing additional construct(s) simultaneously or sequentially prior to the washing step. Further method steps can include isolating the biological sample into individual cells or populations of cells before the contacting step or after the washing step. Another step involves extending the capture oligonucleotide hybridized to the Anchor sequence to copy a construct barcode, UMI and Amplification handle onto double stranded sequences. The double-stranded oligonucleotide sequences can also be generated after anchor hybridization with primers annealed to the Amplification handles after either anchor hybridization and/or insertion of UMIs.

In some embodiments, an oligonucleotide comprises one or more barcodes. Any suitable barcode can be used for a composition or method described herein. A barcode often comprises or consists of a relatively short nucleic acid sequence of, for example, 2 to 50, 2 to 30, 2 to 20, 2 to 15, 10-20, 4 to 15, or 2 to 5 consecutive nucleotides, where the nucleotide sequence of a barcode is unique to a nucleic acid, an oligonucleotide, a population of oligonucleotides (e.g., a plurality of substantially identical oligonucleotides), a population of substantially identical constructs, a sample, a sample source, a ligand, a lot, a run, or a combination thereof. For example, a barcode that is unique to an oligonucleotide attached to a first ligand, can be used to identify the presence of, or amount of the first ligand after detection of the barcode sequence (e.g., by sequencing, or another suitable method). Accordingly, a barcode that is unique to an oligonucleotide attached to a first ligand can be used to specifically identify the presence, amount or absence of a ligand (e.g., a first ligand, a second ligand or an additional ligand) in a multiplex sample comprising other ligands, other nucleic acids, other oligonucleotides and other barcodes. Such a barcode may be termed a "ligand-specific" barcode, or a barcode that specifically identifies a ligand (e.g., a first ligand, or any specific ligand). Similarly, a barcode that is unique to an oligonucleotide, sample, bead, lot, or run, can be used to specifically identify a particular oligonucleotide, sample, bead, lot, or run in a multiplex sample comprising a plurality of other oligonucleotides, samples, beads, lots, or runs. A barcode that can be used to specifically identify a sample may be termed a "sample-specific" barcode, or a barcode that specifically identifies a sample. A barcode that can be used to specifically identify a bead may be termed a "bead-specific" barcode, or a barcode that specifically identifies a bead. A barcode that can be used to specifically identify an oligonucleotide or nucleic acid may be termed a "oligonucleotide-specific" barcode or a "nucleic acid-specific" barcode, respectively. In some embodiments, an oligonucleotide comprises a unique molecular identifier (UMI). In certain embodiments, a UMI comprises a unique barcode that specifically identifies an individual oligonucleotide from all other oligonucleotides used in a composition or method described herein.

Methods and compositions described herein can be used, in some embodiments, to determine the presence, amount, or absence of a sample, target, construct or oligonucleotide. In some embodiments, determining the amount of a sample, target, construct or oligonucleotide comprises determine an absolute, approximate, mean, average or relative amount of a sample, target, construct or oligonucleotide in a multiplex assay. Accordingly, in certain embodiments, methods and compositions described herein can be used to quantitate amounts of a sample, target, construct or oligonucleotide in a multiplex assay.

In some embodiments, an oligonucleotide comprises an amplification handle. Any suitable amplification handle can be used for a composition or a method described herein. In some embodiments, an amplification handle comprises a relatively short length of consecutive amino acids that is integrated into an oligonucleotide, or nucleic acid described herein. An amplification handle can be any suitable length. In some embodiments, an amplification handle is 5 to 50, 5 to 40, 5 to 35, 5 to 25 or 5 to 15 nucleotides in length. In certain embodiments, an amplification handle is used for capture and/or amplification and/or sequencing of a nucleic acid. An amplification handle may comprise any nucleic acid sequence suitable for primer binding, capture, extension by a polymerase, and/or amplification by a polymerase. In some embodiments, an amplification handle comprises a primer binding site. In some embodiments, a primer comprises a nucleic acid sequence substantially identical to an amplification handle. In certain embodiments an oligonucleotide comprises an interposed nucleic acid flanked by a 5' and 3' amplification handle, or complement thereof, wherein the flanking amplification handles facilitate amplification of the interposed nucleic acid.

Another variation of this method involves cleaving the ligand from the construct prior to or after Anchor hybridization to a complementary sequence. Still another embodiment involves lysing the cell, when desired. In various embodiments, the lysis technique can involve exposure of the cells to detergents, detergent-buffer solutions, such as RIPA buffer, IP-lysis buffers, M-PER or B-PER reagent solutions (Pierce Chemical) and the like. The ligand-oligonucleotide constructs can be used with targets other than cell surface antibodies and ligands other than antibodies as discussed herein.

A further embodiment involves cell permeabilization and an optional fixation procedure before the contacting step or between sequential contacting steps with first or additional constructs. In various embodiments, the permeabilizing technique can involve exposure of the biological samples to organic solvents (for example but not limited to methanol andacetone), detergents (such as Saponin™, Triton X-100™ and Tween-20™), other reagent available to one of skill in the art (such as Zinc Salt Solution[32], eBioscience™ Intracellular Fixation & Permeabilization Buffer Set and FIX & PERM® Cell Fixation & Cell Permeabilization Kit) and any combination thereof. The fixation step is optional before or during the permeabilization. Techniques of fixation are known to one of skill in the art, for example contacting the biological samples with solution containing crosslinking fixatives (such as formaldehyde, glutaraldehyde and other aldehyde), precipitating fixatives (such as methanol, ethanol, acetone and acetic acid), oxidizing agents (such as osmium tetroxide, potassium dichromate, chromic acid and potassium permanganate), mercurials, picrates, Hepes-glutamic acid buffer-mediated organic solvent protection effect (HOPE) fixative, 2,4,6-Trimethylpyridine, eBioscience™ Intracellular Fixation & Permeabilization Buffer Set, FIX & PERM® Cell Fixation & Cell Permeabilization Kit or any combination thereof. In yet a further embodiments, additional step of retrieving a sufficient quantity and quality of constructs, DNA or RNA after the permeabilization is involved. For example, see ref 33.

Further these methods can employ detection protocols, including without limitation, PCR, Immuno-PCR[15] and proximity ligation or proximity extension assay[16] protocols, PEA[26], RCA[25], sequencing and fluorescence hybridization protocols.

In still a further embodiment, the method is a high-throughput method. In one embodiment, the compositions described herein are used in high-throughput protocols such as the following. A high-throughput method for detecting one or more epitopes in a biological sample can employ hundreds or thousands of wells containing the same or different samples. The method comprising contacting a biological sample with a composition comprising a first construct that comprises a first antibody or fragment thereof that binds specifically to a first epitope, the first antibody or fragment attached or conjugated to an construct oligonucleotide sequence by a linker, wherein the construct oligonucleotide sequence comprises: an Amplification Handle, a Barcode Sequence that specifically identifies the first antibody or fragment from any other antibody or fragment that recognizes a different epitope, an optional Unique Molecular Identifier sequence that is positioned adjacent to the Barcode on its 5' or 3' end, and an Anchor sequence (e.g., of at least 3 nucleotides) for hybridizing to a complementary sequence for generating a double-stranded oligonucleotide sequence.

In a similar embodiment, the composition comprises one or more substantially identical constructs, wherein each substantially identical first construct differs only in the sequence of the optional Unique Molecular Identifier or its absence from a reference (e.g., "first" or "additional") construct. In another embodiment, the composition comprises at least one additional construct, which comprises an additional antibody or fragment thereof attached or conjugated to an additional construct oligonucleotide sequence by a linker. The additional antibody or fragment thereof binds specifically to an additional epitope. The additional construct oligonucleotide sequence comprises: the same or different Amplification Handle, an additional Barcode that specifically identifies the additional antibody or fragment thereof; an optional additional Unique Molecular Identifier that is positioned adjacent to the additional Barcode on its 5' or 3' end, and the same or different Anchor, wherein the additional target and the additional antibody or fragment ligand, optional UMI, and additional Barcode components differ from the corresponding components in any other construct in the composition.

High-throughput protocols also involve washing the biological sample to remove unbound constructs; annealing the construct oligonucleotide sequence(s) through their respective Anchors to the corresponding complementary sequences and generating double stranded oligonucleotide sequence(s). UMIs may also be optionally inserted to a position adjacent to the Barcode on its 5' or 3' end before or after Anchor hybridization.

Thereafter such methods involve detecting the construct Barcode sequence(s) to identify whether the biological sample (or samples present in individual wells) expresses or contains the first target, the additional targets, or a combination of first target and additional targets. Alternatively, expression level of the first target or additional targets in the biological sample occurs by detecting the amount of the corresponding Barcodes. In one embodiment, the said detection is performed by normalizing to the amount of a Unique Molecular Identifier or the mean amount of two or more Unique Molecular Identifiers.

The high-throughput methods also can include adding one or more first and additional constructs to a biological sample simultaneously or sequentially prior to the washing step. The methods can also include isolating the biological sample(s) bound to one or more of the first or additional constructs into individual cells or populations of cells after washing; and amplifying the double strand oligonucleotide sequence with primers annealed to Amplification Handles. Any of the other parameters of the compositions can be included that coordinate with the assay protocols used in the detection.

Yet another specific embodiment of use of compositions described here in a target detection method is discussed in the examples below. The compositions described herein are designed and used to overcome the limitations of the currently existing methods for detecting and/or measuring RNA transcripts and proteins in single cells (i.e., droplet technology). The method referred to as Cellular Indexing of Transcriptome and Epitopes by sequencing (CITE-seq) uses the compositions described herein to simultaneously characterize the transcriptome and a potentially unlimited number of cell-surface markers from the same cell in a high-throughput manner. It combines unbiased genome-wide expression profiling with the measurement of specific protein markers in thousands of single cells using droplet microfluidics. The compositions can be used, in addition to adding an extra dimension to single-cell transcriptome data. This method provides a more detailed characterization of cell populations, but also allows study of post-transcriptional (and post-translational) gene regulation in single cells at an unprecedented depth.

As described in detail below, a suspension of mixed human and mouse cells and the Drop-seq protocol were employed with constructs comprising monoclonal antibodies as construct ligands attached to construct oligonucleotides containing the unique antibody identifier sequences (Barcodes). The cell suspension is labeled with the ligand—oligonucleotide sequence constructs (in these case oligo-tagged antibodies) and single cells are subsequently encapsulated into nanoliter-sized aqueous droplets in a microfluidic apparatus. In each droplet, antibody and cDNA molecules are indexed with the same unique Barcode and are converted into libraries that are amplified independently and mixed in appropriate proportions for sequencing in the same lane. As reported in the examples below, the inventors were able to unambiguously identify human and mouse cells based on their species-specific cell surface proteins and independently on their transcriptome.

Cellular processes and disease states can be understood with high information content single-cell transcriptomic and proteomic profiling by performing CITE-seq on mini-Drops in diverse laboratory settings. As one embodiment, this CITE-seq method is useful to characterize the hematopoietic system. CITE-seq allows in-depth characterization of single cells by simultaneous measurement of gene-expression levels and cell-surface proteins, is highly scalable, only limited by the number of specific antibodies that are available and is compatible with other single-cell sequencing systems. Among such known single cell sequencing platforms suitable for integration with the compositions and methods described herein is the Drop-seq method, including, but not limited to, microfluidic, plate-based, or microwell, Seq-Well™ method[35] and adaptations of the basic protocol, and InDrop™ method[2] (1 Cell Bio). In another embodiment, a single cell sequencing platform suitable for integration with the compositions and methods described herein is 10× genomics single cell 3' solution (www.10xgenomics.com/single-cell/)[3], or single cell V(D)J solution (www.10xgenomics.com/vdj/, either run on Chromium controller, or dedicated Chromium single cell controller). Still other useful sequencing protocols for combination with CITE-seq as described herein include Wafergen iCell8™ method[3,38-40] (www.wafergen.com/products/icell8-single-cell-system); Microwell-seq method[41], Fluidigm C1™ method[42-44] and equivalent single cell products. Still other known sequencing protocols useful with the compositions and methods described herein include BD Resolve™ single cell analysis platform[37] (derived from Cyto-seq) and ddSeq[6] (from Illumina® Bio-Rad® SureCell™ WTA 3' Library Prep Kit for the ddSEQ™ System, 2017, Pub. No. 1070-2016-014-B, Illumina Inc., Bio-Rad Laboratories, Inc.). In still other embodiment, the compositions and methods described herein are useful with combinatorial indexing based approaches (sci-RNA-seg™ method[20] or SPLiT-seq™ method[30]) and Spatial Transcriptomics, or comparable spatially resolved sequencing approaches[36]. The methods and compositions described herein can also be used as an added layer of information on standard index sorting (FACS) and mRNA-sequencing-based approaches. In one embodiment, for example, standard FACS panels are supplemented with other CITE-seq tagged antibodies detectable through plate-based sequencing. Still other sequencing protocols can be combined with the compositions and methods specifically described herein.

Any suitable nucleic acid sequencing method can be used to sequence the nucleic acids described herein and/or to detect the presence, absence or amount of the various nucleic acids, constructs, targets, oligonucleotides, amplification products and barcodes described herein.

Thus, a high-throughput method for characterizing a cell by simultaneous detection of one or more epitopes located in or on the cell and the transcriptome involves contacting a biological sample containing cells with one or more of the composition as above described. In one embodiment, a composition that comprises a first antibody or fragment thereof that binds specifically to a first epitope located in or on the surface of a cell, the first antibody or fragment is conjugated to a construct oligonucleotide sequence by a linker, wherein the construct oligonucleotide sequence comprises: an Amplification Handle; a Barcode Sequence that specifically identifies the first antibody or fragment from any other antibody or fragment that recognizes a different epitope, an optional Unique Molecular Identifier sequence that is positioned adjacent to the Barcode on its 5' or 3' end, and a polyA sequence of at least 3 nucleotides designed for hybridizing to a polyT sequence immobilized on a microfluidics bead. In another embodiment, the composition comprises one or more substantially identical "first" constructs, wherein each substantially identical first construct differs only in the sequence of the optional Unique Molecular Identifier or its absence from the reference "first" construct.

In still another embodiment, the composition further comprises at least one additional construct, which comprises an additional antibody or fragment thereof conjugated to an additional construct oligonucleotide sequence by a linker, the additional antibody or fragment thereof binding specifically to an additional epitope, and the additional construct oligonucleotide sequence comprising from 5' to 3': the Amplification Handle; an additional Barcode that specifically identifies the additional antibody or fragment thereof; an optional additional Unique Molecular Identifier that is positioned adjacent to the additional Barcode on its 5' or 3' end, and the Anchor, wherein the additional components differ from the corresponding components in any other construct in the composition. The compositions can be added to the biological sample simultaneously or sequentially prior to a washing step. In another embodiment, the composition comprises one or more substantially identical "additional" constructs, wherein each substantially identical additional construct differs only in the sequence of the optional Unique Molecular Identifier or its absence from the reference "additional" construct.

In such a method an individual single cell bound to one or more constructs is encapsulated into an aqueous droplet with one bead, wherein each bead is conjugated to a construct comprising a unique cell Barcode sequence comprising a 3' polyT sequence. The single cell in each droplet is lysed, wherein mRNAs in the cell and the construct oligonucleotide from the antibody or fragment anneal to the polyT sequences of the bead. From the sequences annealed to the bead are generated double stranded cDNAs containing the cell Barcode sequence and the reverse transcripts of the cellular mRNA and a double-stranded DNA containing the cell Barcode sequence and the construct oligonucleotide sequence(s). This method can also include a step of optionally inserting one or more Unique Molecular Identifiers to a position adjacent to the additional Barcode on its 5' or 3' end before or after the annealing or hybridization step.

Further, such a method involves creating by amplification a library containing the cDNA from the target cell's transcriptome, and the DNA containing the construct oligonucleotide sequence(s). In one embodiment, the construct Barcode sequences are detected to identify whether the single cell expresses the first epitope. In another embodiment of the method, the expression level of the first epitope in the single cell is determined by detecting the amount of the construct Barcode. In yet another embodiment of the method, the detection is performed by normalization of the amount of any of the Unique Molecular Identifiers or the mean amount of two or more Unique Molecular Identifiers. Substantially simultaneously, the transcriptome of the library is associated with the cell identified by the binding and identification of the first and/or additional constructs.

Given the number of variations that one can generate in the constructs using the teachings provided herein, many other methods employing these compositions can be used for rapid and complex target identification.

To help define a cell's phenotype, it is essential to have an understanding of the presence or absence of specific surface-protein markers and/or post-translational modifications of these markers. As demonstrated in the examples below, the compositions and methods described herein provide in one aspect a sequencing-based method that combines highly multiplexed ligand-based (e.g., antibody-based) detection of well-established protein markers together with unbiased transcriptome profiling for thousands of single cells in parallel. Specifically, the examples demonstrate a novel method that can profile many targets, e.g., cellular markers and single-cell transcriptomes on thousands of cells in parallel. These compositions and methods permit point-of-collection cell and single-cell profiling at a large and unexpected scale and detail.

In further embodiments, as an additional step to any of the methods described herein, one may first perform a cell-hashtagging step, by labelling every cell within a sample to be analyzed with the same "first construct" and then pooling multiply such hashtagged samples for further analysis. The further analysis includes analysis by any of the methods described herein. The oligonucleotide portions of the cell hashtag constructs, particularly the Amplification Handle sequences, are different from those used in the "further" analytic methods, which permit cell hashtagging of samples subjected to those methods. This "hashtagging" method performed prior to pooling of samples subjected to additional analyses has several advantages. Multiplexing enables cost savings and the ability to control for batch effects—for example, process treated/untreated at the same time. The cell hashtag constructs allow unequivocal determination of most doublets. Finally, the combination of these two advantages allows us to vastly overload droplet-based scRNA-seqexperiments (i.e., use 20,000 cells, rather than 4,000 cells, per lane), resulting in decreased cost of experiments and increased information produced by the experiments. This hashtagging embodiment can be used to multiplex samples of the same genotype without the need to perform genotyping on samples.

In still further embodiments, the hashtagging methods can be extended to barcoding or identifying nuclei as well as other cellular components.

Still further embodiments follow as "A1 through "E36".

A1. A composition comprising a first construct that comprises a first ligand attached or conjugated to a polymer construct by a linker, said first ligand binding specifically to a first target, and said polymer construct comprising:
  a) an Amplification Handle;
  b) a Barcode that specifically identifies said first ligand;
  c) an optional Unique Molecular Identifier that is positioned adjacent to the Barcode on its 5' or 3' end; and
  d) an Anchor for hybridizing to a capture sequence that comprises a sequence complementary to said Anchor.

A2. The composition according to embodiment A1, comprising at least one additional construct, which construct comprises an additional ligand attached or conjugated to an additional polymer construct by a linker, said additional ligand binding specifically to an additional target, and said additional polymer construct comprising:
  a) an Amplification Handle;
  b) an additional Barcode that specifically identifies said additional ligand;
  c) an optional additional Unique Molecular Identifier that is positioned adjacent to the additional Barcode on its 5' or 3' end, and
  d) an Anchor of at least 3 nucleotides for hybridizing to a capture sequence that comprises a sequence complementary to said Anchor.

A3. The composition according to embodiment A2, wherein said additional ligand, additional target, additional Barcode and additional UMI components of each additional construct differ from the corresponding components in any other construct in the composition.

A4. The composition according to any one of embodiments A1 to A3, comprising one or more substantially identical constructs, each substantially identical construct differing from a single reference construct only in the sequence of its optional Unique Molecular Identifier (UMI) or the absence of the UMI from the reference construct.

A5. The composition according to any one of embodiments A1 to A4, wherein said first or additional ligand is independently, any naturally occurring, recombinant, or synthetic biological or chemical molecule.

A6. The composition according to any one of embodiments A1 to A5, wherein said first or additional target is independently, any biological or chemical molecule expressed on the surface of a cell or intracellularly.

A7. The composition according to any one of embodiments A5 or A6, wherein said biological or chemical molecule is selected independently from a peptide, a protein, an antibody or antibody fragment, an affibody, a ribo- or deoxyribo-nucleic acid sequence, an aptamer, a lipid, a polysaccharide, a lectin, or a chimeric molecule formed of multiples of the same or different said first ligands or targets.

A8. The composition according to any one of embodiments A1 to A7, wherein said first ligand is a naturally occurring, synthetic or recombinant antibody, antibody fragment or affibody, and said first target is an epitope located in the cell or on the cell surface.

A9. The composition according to any one of embodiments A1 to A8, wherein said Amplification Handle is a polynucleotide sequence of about 10 nucleotide bases that provides an annealing site for amplification of the polymer construct.

A10. The composition according to any one of embodiments A1 to A9, wherein the Barcode is a defined polynucleotide sequence of at least 2 nucleotide bases specific for a single first or additional ligand.

A11. The composition according to any one of embodiments A1 to A10, wherein the Unique Molecular Identifier is a random nucleic acid sequence of about 8 nucleotide bases that permits identification of duplicates of said polymer construct.

A12. The composition according to any one of embodiments A1 to A11, wherein the Anchor is a polynucleotide or oligonucleotide sequence of at least 3 nucleotide bases which hybridizes to a complementary sequence of its capture sequence.

A13. The composition according to embodiment A12, wherein said Anchor sequence is a polyA sequence or a polyT sequence, or a random oligonucleotide sequence.

A14. The composition according to any one of embodiments A1 to A13, wherein said capture oligonucleotide sequence comprises a sequence complementary to the Anchor sequence of a first or additional construct.

A15. The composition according to embodiment A14, wherein said capture oligonucleotide sequence further comprises one or more of an Amplification Handle sequence, a UMI and its own Barcode sequence.

A16. The composition according to any one of embodiments A1 to A15, wherein said capture sequence is immobilized to a solid substrate by covalent attachment, physical adsorption through charge-charge interation or hydrophobic interaction, Streptavidin-Biotin interation or affinity coupling.

A17. The composition according to embodiment A16, wherein the Substrate is a bead, a microfluidics bead, a slide, a multi-well plate or a chip.

A18. The composition according to any one of embodiments A1 to A17, wherein said capture complementary sequence is a free sequence or primer sequence designed to participate in amplifying the construct oligonucleotide sequence.

A19. The composition according to embodiment A1, wherein the first construct comprises a first antibody or fragment thereof attached or conjugated to a polymer construct by a linker, said first antibody or fragment thereof binding specifically to a first epitope sequence located on the surface of a cell, and said polymer construct comprising:
a) an Amplification Handle;
b) a Barcode that specifically identifies said first antibody or fragment;
c) an optional Unique Molecular Identifier that is positioned adjacently to the Barcode on its 5' or 3' end; and
d) a polyA Anchor sequence of at least 3 nucleotides for hybridizing to a capture polyT sequence.

A20. The composition according to embodiment A19, wherein said capture sequence is immobilized on a microfluidics bead.

A21. The composition according to embodiment A19, wherein the linker comprises biotin, which is bound to the 5' end of the polymer construct by a disulfide bond; and streptavidin, which is fused to the antibody or antibody fragment.

A22. The composition according to any one of embodiments A19 to A21, comprising at least one additional construct, which comprises at least one additional antibody or fragment thereof that binds specifically to an additional epitope located in or on the surface of a cell, said additional antibody or fragment conjugated with an additional polymer construct by a linker, wherein the additional polymer construct comprises:
a) an Amplification Handle;
b) an additional Barcode Sequence that specifically identifies said additional antibody or fragment from any other antibody or fragment that recognizes a different epitope,
c) an optional additional Unique Molecular Identifier sequence that is positioned adjacent the Barcode on its 5' or 3' end, and
d) a capture sequence comprising a polyA sequence of at least 3 nucleotides designed for hybridizing to a polyT sequence, wherein said additional antibody, additional epitope, additional Barcode, and additional UMI components differ from the corresponding components in any other construct in the composition.

A23. The composition according to any one of embodiments A19 to A22, comprising one or more substantially identical constructs, wherein each substantially identical construct differs from any other reference construct in the composition by having a different or no optional Unique Molecular Identifier.

A24. The composition according to any one of embodiments A1 to A23 further comprising one or more preservatives, stabilizers, buffers in a suitable formulation.

A25. A kit comprising one or more of the compositions of embodiments A1 to A24, and optional reagents which comprise a reagent for cleavage of the linker, a wash buffer, a blocking solution, a lysis buffer, an encapsulation solution.

A26. A method for detecting one or more targets in a biological sample, the method comprising contacting the biological sample with one or more of:
a. a composition comprising a first construct that comprises a first ligand attached or conjugated to a polymer construct by a linker, said first ligand binding specifically to a first target, and said polymer construct comprising: an Amplification Handle; a Barcode that specifically identifies said first ligand; an optional Unique Molecular Identifier that is positioned adjacent to the Barcode on its 5' or 3' end; and an Anchor for hybridizing to a capture sequence that comprises a sequence complementary to said Anchor;
b. a composition comprising at least one additional construct, which construct comprises an additional ligand attached or conjugated to an additional polymer construct by a linker, said additional ligand binding specifically to an additional target, and said additional polymer construct comprising an Amplification Handle; an additional Barcode that specifically identifies said additional ligand; an optional additional Unique Molecular Identifier that is positioned adjacent to the additional Barcode on its 5' or 3' end, and an Anchor for hybridizing to a capture sequence that comprises a sequence complementary to said Anchor; and
c. a composition comprising one or more substantially identical constructs, each substantially identical construct differing from any other reference first or additional construct in the sequence of its optional Unique Molecular Identifier (UMI) or the absence of the UMI.

A27. The method according to embodiment A26, further comprising washing the biological sample to remove unbound constructs of the contacting step.

A28. The method according to embodiments A26 or A27 further comprising:
hybridizing the Anchor sequence to a capture oligonucleotide sequence comprising a sequence complementary to said Anchor and generating double stranded oligonucleotide sequences;
extending the capture oligonucleotide hybridized to the Anchor sequence to copy the construct Barcode, UMI and Amplification Handle onto the double stranded sequences; and
amplifying or detecting the sequences.

A29. The method according to embodiment A28, wherein said amplifying or detecting comprises detecting the construct Barcode sequences to identify whether the biological sample expresses or contains the first target, the additional target, or a combination of first target and additional target.

A30. The method according to embodiment A28, wherein said amplifying or detecting comprises determining the expression level of the first target or additional target in the biological sample by detecting the amount of the corresponding construct Barcodes normalized by the amount of any one of Unique Molecular Identifiers or the mean amount of two or more of Unique Molecular Identifiers.

A31. The method according to any one of embodiments A26 to A30, further comprising inserting one or more Unique Molecular Identifiers adjacent to each construct's Barcode on its 5' or 3' end.

A32. The method according to embodiment A27, wherein the contacting step comprises adding one or more of the compositions of embodiments A1 to A24 to said biological sample simultaneously or sequentially.

A33. The method according to any one of embodiments A28 to A32, further comprising isolating individual cells or populations of cells from the biological sample that are bound to one or more said first or additional constructs before the hybridizing step.

A34. The method according to any one of embodiments A28 to A33, wherein the extending step further comprises amplifying the double strand oligonucleotide sequences with primers annealed to the Amplification Handles.

A35. The method according to any one of embodiments A26 to A34, wherein the method is a high throughput method.

A36. The method according to any one of embodiments A26 to A35, wherein the capture sequence is immobilized on a substrate.

A37. The method according to embodiment A36, wherein the substrate is a bead, a slide, a multi-well plate or a chip.

A38. The method according to any one of embodiments A36 or A37, wherein the capture sequence further comprises an additional Amplification Handle; an additional Barcode that specifically identifies the substrate to which the capture sequence is bound; and an optional additional Unique Molecular Identifier that is positioned adjacent the additional Barcode on its 5' or 3' end that identifies each capture sequence.

A39. The method according to any one of embodiments A26 to A38, wherein said biological sample is a population of the same or a mixture of different cells, cell or cell membrane components, tissue, or a lysate of said cells or tissue.

A40. A high-throughput method for detecting one or more epitopes in a biological sample, the method comprising contacting a biological sample with one or more of
  i. a composition comprising a first construct that comprises a first antibody or fragment thereof that binds specifically to a first epitope, said first antibody or fragment attached or conjugated to a first polymer construct by a linker, wherein the first polymer construct comprises: an Amplification Handle; a Barcode Sequence that specifically identifies said first antibody or fragment from any other antibody or fragment that recognizes a different epitope, an optional Unique Molecular Identifier sequence that is positioned adjacent to the 5' or 3' end of the Barcode, and an Anchor sequence for hybridizing to a capture sequence that comprises a sequence complementary to said Anchor;
  ii. a composition of (i) comprising at least one additional construct, which comprises an additional antibody or fragment thereof attached or conjugated to an additional polymer construct by a linker, said additional antibody or fragment thereof binding specifically to an additional epitope, and said additional polymer construct comprising: an Amplification Handle; an additional Barcode that specifically identifies said additional antibody or fragment thereof; an optional additional Unique Molecular Identifier that is positioned adjacent to the 5' or 3' end of the additional Barcode, and an Anchor sequence of (i), wherein said additional construct differs from any other construct in the composition in its antibody, epitope, Barcode, and UMI; and
  iii. a composition of (i) or (ii) comprising one or more substantially identical constructs, each substantially identical construct differing from any other reference first or additional construct in the sequence of its optional Unique Molecular Identifier (UMI) or the absence of the UMI.

A41. The method according to embodiment A40, further comprising washing the biological sample to remove unbound constructs.

A42. The method according to embodiments A40 or A41, further comprising:
  annealing said construct Anchor sequences to the capture oligonucleotide sequences of the contacted sample and generating a double stranded oligonucleotide sequence.

A43. The method according to any of embodiments A40 to A42 further comprising:
  extending the capture oligonucleotide hybridized to the Anchor sequence to copy the construct Barcode, UMI and Amplification Handle onto the double stranded sequences; and
  amplifying or detecting the sequences.

A44. The method according to embodiment A43, wherein said amplifying step comprises detecting the construct Barcode sequences to identify whether the biological sample expresses or contains the first target, the additional target, or a combination of first target and additional target.

A45. The method according to embodiment A43, wherein said amplifying step comprises determining the expression level of the first target or additional target in the biological sample by detecting the amount of the corresponding construct Barcodes is normalized by the amount of any one of the Unique Molecular Identifiers or the mean amount of two or more of Unique Molecular Identifiers.

A46. The method according to any one of embodiments A40 to A45, further comprising inserting one or more Unique Molecular Identifiers adjacent each construct's Barcode on its 5' or 3' end.

A47. The method according to embodiment A40, wherein the contacting step further comprises adding the compositions (i), (ii), (iii) to said biological sample simultaneously or sequentially.

A48. The method according to any one of embodiments A40 to A47, further comprising isolating individual cells, cell or membrane components, tissues or populations of same from the biological sample that are bound to one or more said first or additional constructs further analysis.

A49. The method according to embodiment A43, wherein the extending step further comprises amplifying the double strand oligonucleotide sequences with primers annealed to the Amplification Handles.

A50. The method according to any one of embodiments A40 to A49, wherein the capture sequence is immobilized on a substrate.

A51. The method according to embodiment A50, wherein the substrate is a bead, a slide, a multi-well plate or a chip.

A52. The method according to any one of embodiments A40 to A51, wherein the capture sequence further comprises an Amplification Handle; a Barcode that specifically identifies a specific substrate; and an optional additional Unique Molecular Identifier that is positioned adjacent to the Amplification Handle on its 3' end or the said Barcode on its 3' end.

A53. A high-throughput method for characterizing a cell by simultaneous detection of one or more epitopes located in or on the cell and the transcriptome, the method comprising contacting a biological sample containing cells with one or more of:
(i) a composition that comprises a first construct that comprises a first antibody or fragment thereof that binds specifically to a first epitope located in or on the surface of a cell, said first antibody or fragment conjugated to a first polymer construct by a linker, wherein the first polymer construct comprises an Amplification Handle; a Barcode Sequence that specifically identifies said first antibody or fragment from any other antibody or fragment that recognizes a different epitope, an optional Unique Molecular Identifier sequence that is positioned adjacent the 5' or 3' end of the Barcode, and a polyA Anchor sequence designed for hybridizing to a capture oligonucleotide sequence comprising a polyT sequence immobilized on a microfluidics bead;
ii. a composition of (i) comprising at least one additional construct, which comprises an additional antibody or fragment thereof conjugated to an additional polymer construct by a linker, said additional antibody or fragment thereof binding specifically to an additional epitope, and said additional polymer construct comprising: the Amplification Handle of (i); an additional Barcode that specifically identifies said additional antibody or fragment thereof; an optional additional Unique Molecular Identifier that is positioned adjacent to the 5' or 3' end of the additional Barcode, and the said Anchor of (i), wherein said additional antibody or fragment, additional Barcode, additional UMI and additional epitope differ from the corresponding components in any other construct in the composition; and
iii. a composition of (i) or (ii) comprising one or more substantially identical constructs, each substantially identical construct differing from any other reference first or additional construct in the sequence of its optional Unique Molecular Identifier (UMI) or the absence of the UMI.

A54. The method according to embodiment A53, further comprising:
encapsulating an individual single cell bound to one or more constructs into an aqueous droplet with one said bead, wherein each bead is conjugated to the capture sequence comprising a unique bead Barcode sequence, an optional UMI, and a 3' polyT sequence.

A55. The method according to embodiment A54, further comprising:
lysing the single cell in each droplet, wherein mRNAs in the cell and said polymer construct released from the antibody or fragment anneal to the polyT sequences of the capture sequence; and
generating from the sequences annealed to the bead (A) double stranded cDNAs containing the bead Barcode sequence and the reverse transcripts of the cellular mRNA and (B) a double-stranded DNA containing the bead Barcode sequence and the polymer construct.

A56. The method according to embodiment A55, further comprising creating by amplification a library comprising the cDNA of (A) and the DNA containing the polymer construct of (B); and detecting the sequences.

A57. The method according to embodiment A56, wherein the detecting step comprises detecting the construct Barcode sequences to identify whether the single cell expresses the first epitope.

A58. The method according to embodiment A56, wherein the detecting step comprises determining the expression level of the first or additional epitope in the single cell by detecting the amount of the construct Barcode normalized by the amount of any of the Unique Molecular Identifiers or the mean amount of two or more Unique Molecular Identifiers.

A59. The method according to any one of embodiments A57 or A58, further comprising associating the transcriptome or components of the transcriptome of the library with the cell on which the target epitope was identified.

A60. The method according to any one of embodiments A53 to A59, wherein the contacting step further comprises adding the compositions (i), (ii), (iii) to said biological sample simultaneously or sequentially.

B1. A method for detecting at least two targets in at least a first and a second sample, the method comprising:
a) contacting the first sample with a first construct comprising a first ligand attached to a first oligonucleotide, wherein the first ligand binds specifically to a first target, and the first oligonucleotide comprises:
i) a first amplification handle,
ii) a first barcode that specifically identifies the first sample, and
iii) an anchor comprising a polyA sequence;
b) contacting the second sample with a second construct comprising the first ligand attached to a second oligonucleotide, wherein the second oligonucleotide comprises:
i) the first amplification handle,
ii) a second barcode that specifically identifies the second sample, and
iii) the anchor;
c) contacting the first and the second samples with a third construct comprising a second ligand attached to a third oligonucleotide, wherein the second ligand binds specifically to a second target, and the third oligonucleotide comprises:
(i) a second amplification handle,
(ii) a third barcode that specifically identifies the second ligand, and
(iii) the anchor; and
d) contacting the first and the second samples with a fourth construct comprising a third ligand attached to a fourth oligonucleotide, wherein the third ligand binds specifically to a third target, and the fourth oligonucleotide comprises:
i) the second amplification handle,
ii) a fourth barcode that specifically identifies the third ligand, and
iii) the anchor.

B2. The method of embodiment B1, wherein first and second samples comprise cells.

B3. The method of embodiment B1 or B2, wherein the contacting of c) comprises contacting the cells of the first or second samples with the third construct and the contacting of d) comprises contacting the cells of the first and second samples with the fourth construct.

B4. The method of any one of embodiments B1 to B3, wherein the contacting of a) and b) takes place prior to the contacting of c) or d).

B5. The method of any one of embodiments B1 to B4, wherein the contacting of c) comprises contacting a mixture of the first and second samples with the third construct and the contacting of d) comprises contacting the mixture with the fourth construct.

B6. The method of any one of embodiments B1 to B5, wherein first, second, or third ligands comprise an antibody, or antigen binding fragment thereof.

B7. The method of any one of embodiments B1 to B6, wherein (i) the anchor of the first oligonucleotide is located 3' of the first amplification handle of the first oligonucleotide and 3' of the first barcode; (ii) the anchor of the second oligonucleotide is located 3' of the first amplification handle of the second oligonucleotide and 3' of the second barcode; (iii) the anchor of the third oligonucleotide is located 3' of the second amplification handle of the third oligonucleotide and 3' of the third barcode; and (iv) the anchor of the fourth oligonucleotide is located 3' of the second amplification handle of the fourth oligonucleotide and 3' of the fourth barcode.

B8. The method of any one of embodiments B1 to B7, wherein (i) the first amplification handle of the first oligonucleotide is located 5' of the first barcode and 5' of the anchor of the first oligonucleotide; (ii) the first amplification handle of the second oligonucleotide is located 5' of the second barcode and 5' of the anchor of the second oligonucleotide; (iii) the second amplification handle of the third oligonucleotide is located 5' of the third barcode and 5' of the anchor of the third oligonucleotide; and (iv) the second amplification handle of the fourth oligonucleotide is located 5' of the fourth barcode and 5' of the anchor of the fourth oligonucleotide.

B9. The method of any one of embodiments B2 to B8, wherein the first, the second and the third targets comprise a protein or molecule located in, or on a surface of, one or more of the cells of the first and second samples.

B10. The method of any one of embodiments B1 to B9, wherein the polyA sequence comprises a sequence comprising ten or more consecutive adenosine nucleotides, or a derivative of an adenosine nucleotide.

B11. The method of any one of embodiments B1 to B10, wherein the first ligand, the second ligand and the third ligand comprise an antibody or antigen binding fragment thereof.

B12. The method of any one of embodiments B1 to B11, further comprising washing the first sample after step a) and washing the second sample after step b) to remove unbound constructs.

B13. The method of any one of embodiments B1 to B12, wherein the contacting of step a) takes place before, after or at the same time as the contacting step b).

B14. The method of any one of embodiments B1 to B13, wherein the contacting of step c) takes place before, after or at the same time as the contacting step d).

B15. The method of any one of embodiments B1 to B14, further comprising washing the first and the second samples after step c) or after step d) to remove unbound constructs.

B16. The method of any one of embodiments B2 to B15, further comprising, after c) and d), encapsulating a first single cell of the first sample in a first droplet comprising a first bead conjugated to a plurality of a first capture oligonucleotide comprising, from 5' to 3', a third amplification handle, a fifth barcode identifying the first bead, and a polyT sequence, and encapsulating a second single cell of the second sample in a second droplet comprising a second bead conjugated to a plurality of a second capture oligonucleotide comprising, from 5' to 3', the third amplification handle, a sixth barcode identifying the second bead, and a polyT sequence.

B17. The method of embodiment B16, further comprising, lysing the first and second single cells thereby providing a first lysate encapsulated in the first droplet and a second lysate encapsulated in the second droplet, wherein the first and second lysates comprise mRNA.

B18. The method of embodiment B16 or B17, further comprising contacting the lysate of the first and second cells with a polymerase.

B19. The method of any one of embodiments B16 to B18, further comprising generating cDNA and double stranded oligonucleotide sequences of the first, second, third and fourth oligonucleotides.

B20. The method of any one of embodiments B16 to B19, further comprising amplifying or detecting the first, second, third, fourth, fifth and sixth barcode sequences.

B21. The method of embodiment B20, wherein the amplifying or detecting comprises determining the presence or absence of the second, or third targets in the first and second samples.

B22. The method of any one of embodiments B1 to B21, wherein the first, second, third or fourth oligonucleotides, or the first or second capture oligonucleotides comprise a UMI.

C1. A kit comprising:
a) a first construct comprising a first ligand attached to a first oligonucleotide, wherein the first ligand binds specifically to a first target, and the first oligonucleotide comprises:
i) a first amplification handle,
ii) a first unique barcode configured to specifically identify a first sample, and
iii) an anchor comprising a polyA sequence;
b) a second construct comprising the first ligand attached to a second oligonucleotide, wherein the second oligonucleotide comprises:
i) the first amplification handle,
ii) a second unique barcode configured to specifically identify a second sample, and
iii) the anchor;
c) a third construct comprising a second ligand attached to a third oligonucleotide, wherein the second ligand binds specifically to a second target, and the third oligonucleotide comprises:

(i) a second amplification handle,
(ii) a third unique barcode configured to specifically identify the second ligand, and
(iii) the anchor; and
d) a fourth construct comprising a third ligand attached to a fourth oligonucleotide, wherein the third ligand binds specifically to a third target, and the fourth oligonucleotide comprises:
i) the second amplification handle,
ii) a fourth unique barcode configured to specifically identify the third ligand, and
iii) the anchor.

C2. The kit of embodiment B1, further comprising a plurality of beads, wherein each bead is independently conjugated to a plurality of a capture oligonucleotide comprising:
i) a fourth amplification handle
ii) a bead-specific barcode unique to each bead; and
iii) a polyT sequence.

C3. The kit of embodiment C1 or C2, wherein first, second, or third ligands comprise an antibody, or antigen binding fragment thereof.

C4. The kit of any one of embodiments C1 to C3, wherein (i) the anchor of the first oligonucleotide is located 3' of the first amplification handle of the first oligonucleotide and 3' of the first barcode; (ii) the anchor of the second oligonucleotide is located 3' of the first amplification handle of the second oligonucleotide and 3' of the second barcode; (iii) the anchor of the third oligonucleotide is located 3' of the second amplification handle of the third oligonucleotide and 3' of the third barcode; and (iv) the anchor of the fourth oligonucleotide is located 3' of the second amplification handle of the fourth oligonucleotide and 3' of the fourth barcode.

C5. The kit of any one of embodiments C1 to C4, wherein (i) the first amplification handle of the first oligonucleotide is located 5' of the first barcode and 5' of the anchor of the first oligonucleotide; (ii) the first amplification handle of the second oligonucleotide is located 5' of the second barcode and 5' of the anchor of the second oligonucleotide; (iii) the second amplification handle of the third oligonucleotide is located 5' of the third barcode and 5' of the anchor of the third oligonucleotide; and (iv) the second amplification handle of the fourth oligonucleotide is located 5' of the fourth barcode and 5' of the anchor of the fourth oligonucleotide.

C6. The kit of any one of embodiments C1 to C5, wherein the first, the second and the third targets comprise a protein or molecule located in, or on a surface of, a cell.

C7. The kit of any one of embodiments C1 to C6, wherein the polyA sequence comprises a sequence comprising ten or more consecutive adenosine nucleotides, or a derivative of an adenosine nucleotide.

C8. The kit of any one of embodiments C2 to C7, wherein the polyT sequence comprises a sequence comprising ten or more consecutive thymidine nucleotides, or a derivative of a thymidine nucleotide.

C9. The kit of any one of embodiments C2 to C7, wherein the polyT sequence comprises a sequence comprising ten or more consecutive uridine nucleotides, or a derivative of a uridine nucleotide.

D1. A composition comprising a construct comprising a ligand attached to an oligonucleotide, wherein the ligand binds specifically to a target, and the oligonucleotide comprises:

i) an amplification handle,
ii) a unique barcode configured to specifically identify a first sample, and
iii) an anchor comprising a polyA sequence.

D2. The composition of embodiment D1, wherein the ligand comprises an antibody or an antigen binding fragment thereof.

D3. The composition of embodiment D1 or D2, wherein the polyA sequence comprises a sequence comprising ten or more consecutive adenosine nucleotides, or a derivative of an adenosine nucleotide.

D4. The composition of any one of embodiments D1 to D3, wherein (i) the anchor is located 3' of the amplification and 3' of the unique barcode.

D5. The composition of any one of embodiments D1 to D4, the amplification handle is located 5' of the unique barcode and 5' of the anchor.

D6. The composition of any one of embodiments D1 to D5, wherein the target comprises a protein or molecule located in, or on a surface of, a cell.

E1. A method for detecting at least two targets in at least a first and a second sample, the method comprising:
a) contacting the first sample with a first construct comprising a first ligand attached to a first oligonucleotide, wherein the first ligand binds specifically to a first target, and the first oligonucleotide comprises:
i) a first amplification handle,
ii) a first barcode that specifically identifies the first sample, and
iii) an anchor comprising a polyA sequence;
b) contacting the second sample with a second construct comprising the first ligand attached to a second oligonucleotide, wherein the second oligonucleotide comprises:
i) the first amplification handle,
ii) a second barcode that specifically identifies the second sample, and
iii) the anchor;
c) contacting the first and the second samples with a third construct comprising a second ligand attached to a third oligonucleotide, wherein the second ligand binds specifically to a second target, and the third oligonucleotide comprises:
(i) a second amplification handle,
(ii) a third barcode that specifically identifies the second ligand, and
(iii) the anchor; and
d) contacting the first and the second samples with a fourth construct comprising a third ligand attached to a fourth oligonucleotide, wherein the third ligand binds specifically to a third target, and the fourth oligonucleotide comprises:
i) the second amplification handle,
ii) a fourth barcode that specifically identifies the third ligand, and
iii) the anchor.

E2. The method of embodiment E1, wherein first and second samples comprise cells.

E3. The method of embodiment E1 or E2, wherein the contacting of c) comprises contacting the cells of the first or second samples with the third construct, and the contacting of d) comprises contacting the cells of the first and second samples with the fourth construct.

E4. The method of any one of embodiments E1 to E3, wherein the contacting of a) and b) takes place prior to the contacting of c) or d).

E5. The method of any one of embodiments E1 to E4, wherein the contacting of c) comprises contacting a mixture of the first and second samples with the third construct and the contacting of d) comprises contacting the mixture with the fourth construct.

E6. The method of any one of embodiments E1 to E5, wherein the first, second, or third ligands comprise an antibody, or antigen binding fragment thereof.

E7. The method of any one of embodiments E1 to E6, wherein (i) the anchor of the first oligonucleotide is located 3' of the first amplification handle of the first oligonucleotide and 3' of the first barcode; (ii) the anchor of the second oligonucleotide is located 3' of the first amplification handle of the second oligonucleotide and 3' of the second barcode; (iii) the anchor of the third oligonucleotide is located 3' of the second amplification handle of the third oligonucleotide and 3' of the third barcode; and (iv) the anchor of the fourth oligonucleotide is located 3' of the second amplification handle of the fourth oligonucleotide and 3' of the fourth barcode.

E8. The method of any one of embodiments E1 to E7, wherein (i) the first amplification handle of the first oligonucleotide is located 5' of the first barcode and 5' of the anchor of the first oligonucleotide; (ii) the first amplification handle of the second oligonucleotide is located 5' of the second barcode and 5' of the anchor of the second oligonucleotide; (iii) the second amplification handle of the third oligonucleotide is located 5' of the third barcode and 5' of the anchor of the third oligonucleotide; and (iv) the second amplification handle of the fourth oligonucleotide is located 5' of the fourth barcode and 5' of the anchor of the fourth oligonucleotide.

E9. The method of any one of embodiments E2 to E8, wherein the first, the second and the third targets comprise a protein or molecule located in, or on a surface of, one or more of the cells of the first and second samples.

E10. The method of any one of embodiments E1 to E9, wherein the polyA sequence comprises a sequence comprising ten or more consecutive adenosine nucleotides, or a derivative of an adenosine nucleotide.

E11. The method of any one of embodiments E1 to E10, further comprising washing the first sample after step a) and washing the second sample after step b) to remove unbound constructs.

E12. The method of any one of embodiments E1 to E11, wherein the contacting of step a) takes place before, after or at the same time as the contacting step b).

E13. The method of any one of embodiments E1 to E12, wherein the contacting of step c) takes place before, after or at the same time as the contacting step d).

E14. The method of any one of embodiments E1 to E13, further comprising washing the first and the second samples after step c) or after step d) to remove unbound constructs.

E15. The method of any one of embodiments E2 to E14, further comprising, after c) and d), encapsulating a first single cell of the first sample in a first droplet comprising a first bead conjugated to a plurality of a first capture oligonucleotide comprising, from 5' to 3', a third amplification handle, a fifth barcode identifying the first bead, and a polyT sequence, and encapsulating a second single cell of the second sample in a second droplet comprising a second bead conjugated to a plurality of a second capture oligonucleotide comprising, from 5' to 3', the third amplification handle, a sixth barcode identifying the second bead, and a polyT sequence.

E16. The method of embodiment E15, further comprising, lysing the first and second single cells thereby providing a first lysate encapsulated in the first droplet and a second lysate encapsulated in the second droplet, wherein the first and second lysates comprise mRNA.

E17. The method of embodiment E15 or E16, further comprising contacting the lysate of the first and second cells with a polymerase.

E18. The method of any one of embodiments E15 to E17, further comprising generating cDNA and double stranded oligonucleotide sequences of the first, second, third and fourth oligonucleotides.

E19. The method of any one of embodiments E15 to E18, further comprising amplifying or detecting the first, second, third, fourth, fifth and sixth barcode sequences.

E20. The method of embodiment E19, wherein the amplifying or detecting comprises determining the presence or absence of the second, or third targets in the first and second samples.

E21. The method of any one of embodiments E1 to E20, wherein the first, second, third or fourth oligonucleotides, or the first or second capture oligonucleotides comprise a UMI.

E22. A kit comprising:
 a) a first construct comprising a first ligand attached to a first oligonucleotide, wherein the first ligand binds specifically to a first target, and the first oligonucleotide comprises:
  i) a first amplification handle,
  ii) a first unique barcode configured to specifically identify a first sample, and
  iii) an anchor comprising a polyA sequence;
 b) a second construct comprising the first ligand attached to a second oligonucleotide, wherein the second oligonucleotide comprises:
  i) the first amplification handle,
  ii) a second unique barcode configured to specifically identify a second sample, and
  iii) the anchor;
 c) a third construct comprising a second ligand attached to a third oligonucleotide, wherein the second ligand binds specifically to a second target, and the third oligonucleotide comprises:
  (i) a second amplification handle,
  (ii) a third unique barcode configured to specifically identify the second ligand, and
  (iii) the anchor; and
 d) a fourth construct comprising a third ligand attached to a fourth oligonucleotide, wherein the third ligand binds specifically to a third target, and the fourth oligonucleotide comprises:
  i) the second amplification handle,
  ii) a fourth unique barcode configured to specifically identify the third ligand, and
  iii) the anchor.

E23. The kit of embodiment E22, further comprising a plurality of beads, wherein each bead is independently conjugated to a plurality of a capture oligonucleotide comprising:
 i) a fourth amplification handle
 ii) a bead-specific barcode unique to each bead; and
 iii) a polyT sequence.

E24. The kit of embodiment E22 or E23, wherein first, second, or third ligands comprise an antibody, or antigen binding fragment thereof.

E25. The kit of any one of embodiments E22 to E24, wherein (i) the anchor of the first oligonucleotide is located 3' of the first amplification handle of the first oligonucleotide and 3' of the first barcode; (ii) the anchor of the second oligonucleotide is located 3' of the first amplification handle of the second oligonucleotide and 3' of the second barcode; (iii) the anchor of the third oligonucleotide is located 3' of the second amplification handle of the third oligonucleotide and 3' of the third barcode; and (iv) the anchor of the fourth oligonucleotide is located 3' of the second amplification handle of the fourth oligonucleotide and 3' of the fourth barcode.

E26. The kit of any one of embodiments E22 to E25, wherein (i) the first amplification handle of the first oligonucleotide is located 5' of the first barcode and 5' of the anchor of the first oligonucleotide; (ii) the first amplification handle of the second oligonucleotide is located 5' of the second barcode and 5' of the anchor of the second oligonucleotide; (iii) the second amplification handle of the third oligonucleotide is located 5' of the third barcode and 5' of the anchor of the third oligonucleotide; and (iv) the second amplification handle of the fourth oligonucleotide is located 5' of the fourth barcode and 5' of the anchor of the fourth oligonucleotide.

E27. The kit of any one of embodiments E22 to E26, wherein the first, the second and the third targets comprise a protein or molecule located in, or on a surface of, a cell.

E28. The kit of any one of embodiments E22 to E27, wherein the polyA sequence comprises a sequence comprising ten or more consecutive adenosine nucleotides, or a derivative of an adenosine nucleotide.

E29. The kit of any one of embodiments E23 to E28, wherein the polyT sequence comprises a sequence comprising ten or more consecutive thymidine nucleotides, or a derivative of a thymidine nucleotide.

E30. The kit of any one of embodiments E23 to E28, wherein the polyT sequence comprises a sequence comprising ten or more consecutive uridine nucleotides, or a derivative of a uridine nucleotide.

E31. A composition comprising a construct comprising a ligand attached to an oligonucleotide, wherein the ligand binds specifically to a target, and the oligonucleotide comprises:
  i) an amplification handle,
  ii) a unique barcode configured to specifically identify a first sample, and
  iii) an anchor comprising a polyA sequence.

E32. The composition of embodiment E31, wherein the ligand comprises an antibody or an antigen binding fragment thereof.

E33. The composition of embodiment E31 or E32, wherein the polyA sequence comprises a sequence comprising ten or more consecutive adenosine nucleotides, or a derivative of an adenosine nucleotide.

E34. The composition of any one of embodiments E31 to E33, wherein (i) the anchor is located 3' of the amplification and 3' of the unique barcode.

E35. The composition of any one of embodiments E31 to E34, the amplification handle is located 5' of the unique barcode and 5' of the anchor.

E36. The composition of any one of embodiments E31 to E35, wherein the target comprises a protein or molecule located in, or on a surface of, a cell.

The following examples disclose the CITE-seq method and a cell hashtagging method as merely two embodiments of use of the compositions described herein. These examples should be construed to encompass any and all variations that become evident as a result of the teaching provided herein.

EXAMPLES

Example 1: Design and Validation of Antibody-Oligo Complexes

Figure 2A:
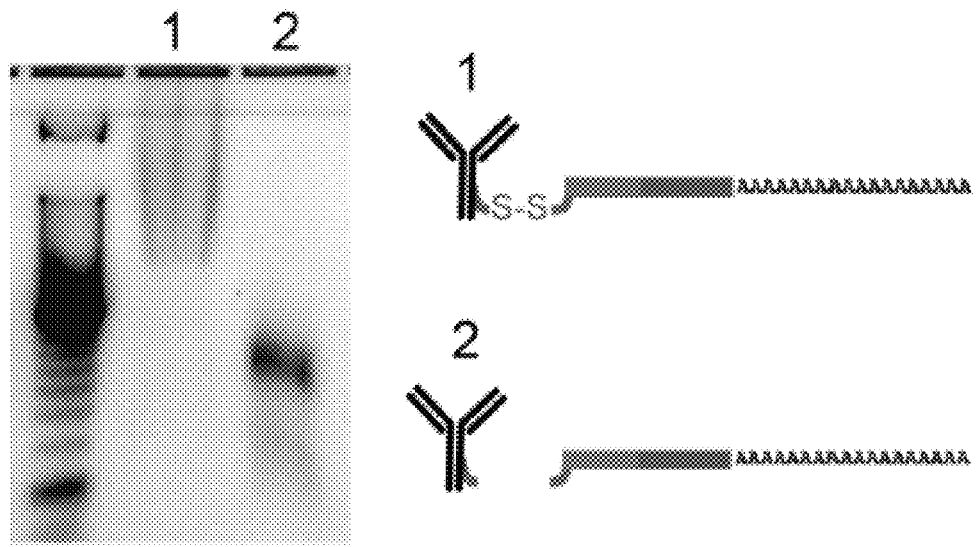
FIGS. 2A through 2E are graphs showing that CITE-seq accurately identifies different species in mixing experiment.
Figure 2B:
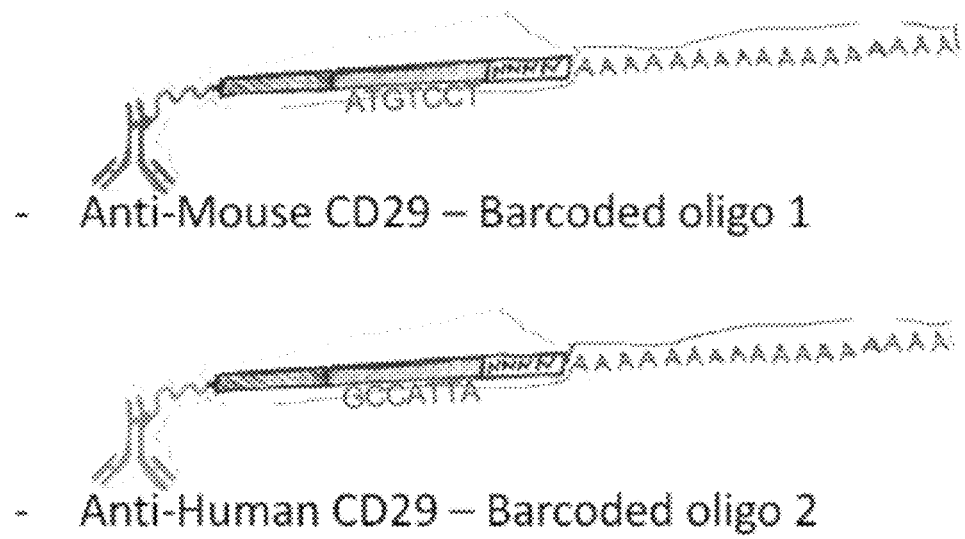

Antibody-oligos were designed with the following characteristics: a generic Amplification Handle (PCR handle) for next-generation sequencing library preparation, a unique Barcode sequence specific for each antibody, and a polyA stretch at the 3' end (FIG. 1A). Two antibody-oligos were generated. Anti-Mouse Integrin Beta-1 (CD29) antibodies were linked to Barcoded oligo 1 containing a disulfide bridge, a common sequence (Amplification Handle, PCR handle), a unique antibody identifier Barcode (5'-ATGTCCT-3') and a UMI containing 4 nt followed by a polyA tail (FIG. 2B, top panel). Anti-human CD29 antibodies were linked to Barcoded oligo 2 containing a disulfide bridge, a common sequence (Amplification Handle, PCR handle), a unique antibody identifier Barcode (5'-GC-CATTA-3') and a UMI containing 4 nt followed by a polyA tail (FIG. 2B, bottom panel).

For the experiments presented in Examples 1 to 7, the oligos were modified with biotin and a disulfide bond at the 5' end of the oligo and were bound to streptavidin modified antibodies. The oligo could be released from the antibody by reducing the disulfide bond. Specifically, a commonly used streptavidin-biotin (SAV) interaction to link antibodies to oligonucleotides[19] was adopted for Examples 1 to 7. A commercially available kit to streptavidin label antibodies (generally used for subsequent fluorophore labelling for FACS) was used. Antibodies were linked to biotinylated oligos (FIG. 2A, Lane and Panel #1). Reducing a disulfide bond at the 5' end of the oligo released these oligos from antibodies (FIG. 2A, Lane and Panel #2). Other attachment chemistries are useful, including but not limited to thiol-maleimide, thiol-haloacetate, amine-NHS, amine-isothiocyanate, azide-alkyne (CuAAC), tetrazole-cyclooctene (iEDDA, used in Example 7,[45] (refs. 25, 45 and 46 and references therein), and can be cleavable or non-cleavable covalent linkages.

Example 2: Methods and Materials

Conjugation of Antibodies to DNA-Barcoding Oligonucleotides.

Highly specific, flow-cytometry-tested monoclonal antibodies were conjugated to oligonucleotides containing unique antibody-identifier sequences and a polyA tail.

We adopted a commonly used streptavidin-biotin interaction to link oligos to antibodies[19]. Antibodies were streptavidin labeled using the LYNX Rapid Streptavidin Antibody Conjugation Kit (Bio-Rad, USA) according to manufacturer's instructions with modifications. Specifically, we labeled 15 µg of antibody with 10 µg of streptavidin. At this ratio, an average of two streptavidin tetramers will be conjugated per antibody molecule, which results in an average of eight binding sites for biotin on each antibody. DNA oligonucleotides with a 5' amine modification were purchased at IDT (USA) and biotinylated using NETS-chemistry according to manufacturer's instructions (EZ Biotin S-S NHS, Thermo Fisher Scientific, USA). The optional disulfide bond allows separation of the oligo from the antibody with reducing agents in some embodiments. Separation of the oligo from the antibody may not be needed for all applications. Excess Biotin-NHS was removed by gel filtration (Micro Biospin 6, Bio-Rad) and ethanol precipitation. Streptavidin-labeled antibodies were incubated with biotinylated oligonucleotides in equimolar ratio (assuming two streptavidin tetramers per antibody on average) overnight at 4° C. in PBS containing 0.5 M NaCl and 0.02% Tween. Unbound oligo was removed from antibodies using centrifugal filters with a 50 KDa MW cutoff (Millipore, USA). Removal of excess oligo was verified by 4% agarose gel electrophoresis. Antibody-oligo conjugates were stored in PBS supplemented with sodium azide (0.05%) and BSA (1 µg/µl) at 4° C.

List of Antibodies Used for CITE-Seq.

Antibodies and clones used were CD3e (Clone UCHT1, BioLegend, USA); CD19 (Clone HIB19, BioLegend, USA); CD4 (Clone RPA-T4, BioLegend, USA); CD8a (Clone RPA-T8, BioLegend, USA); CD56 (Clone MEM-188, BioLegend, USA); CD16 (Clone B73.1, BioLegend, USA); CD11c (Clone B-ly6, BD Pharmingen, USA); CCR7 (Clone 150603, R&D Systems, USA); CCR5 (Clone J418F1, BioLegend, USA); CD34 (Clone 581, BioLegend, USA); CD14 (Clone M5E2, BioLegend, USA); CD10 (Clone HI10a, BioLegend, USA); CD45RA (Clone HI100, BioLegend, USA); D29 (Clone MA1-19105, Thermo Fisher, USA); CD29 (Clone MA5-16707, Thermo Fisher, USA); CD2 (Clone RPA-2.10, BioLegend, USA); CD57 (Clone H-NK1, BioLegend, USA). See Ref 46, supplementary Table 2, incorporated by reference herein.

Antibody-Oligo Sequences.

We leverage the DNA-dependent DNA polymerase activity of commonly used reverse transcriptases[56] to convert CITE-seq DNA oligonucleotides into cDNA during reverse transcription at the same time as mRNAs. The DNA-dependent DNA polymerase activity of MMLV reverse transcriptases is well established. All SMART (switching mechanism at 5' end of RNA template) library prep protocols (e.g., commercialized by Clontech) rely on this activity. The RT enzyme switches at the end of the RNA template to a template-switch oligo (TSO), for further cDNA synthesis. Single cell RNA-seq protocols (including 10× Genomics and Drop-seq) also rely entirely on this activity to append a PCR handle to the 5' end of full-length cDNAs. The PCR handle is used for subsequent amplification. Depending on the application, the PCR amplification handle in the antibody-barcoding oligos must be changed depending on which sequence read is used for RNA readout (e.g., 10× Single Cell 3' v1 uses read 1, while Drop-seq and 10× Single Cell 3' v2 use read 2). Our proof-of-principle human and mouse antibody-barcoding oligonucleotide designs included:

UMIs, which are redundant for Drop-seq and 10× protocols due to the UMI addition to the cDNA at reverse transcription. UMIs on the antibody-conjugated oligonucleotide may be useful for other iterations of the method where UMIs are not part of the scRNA-seq library preparation protocol.

Species mixing, Drop-seq (containing Nextera read 2 handle).
BC6:
SEQ ID NO: 1
/5AmMC12/GTCTCGTGGGCTCGGAGATGTGTATA

AGAGACAGGCCAATNNBAAAAAAAAAAAAAAAAAAAA

AAAAAAAAAAAAAAA

BC12:
SEQ ID NO: 2
/5AmMC12/GTCTCGTGGGCTCGGAGATGTGT

ATAAGAGACAGCTTGTANNBAAAAAAAAAAAAAAAAAAA

AAAAAAAAAAAAAAAA

Species mixing, 10x (single cell 3' version 1, Nextera read1 handle).
BC6:
SEQ ID NO: 3
/5AmMC12/TCGTCGGCAGCGTCAGATGT

GTATAAGAGACAGGCCAATNNBAAAAAAAAAAAAAAAAA

AAAAAAAAAAAAAAAAAA

BC12:
SEQ ID NO: 4
/5AmMC12/TCGTCGGCAGCGTCAGATGTGTATA

AGAGACAGCTTGTANNBAAAAAAAAAAAAAAAAAAAAA

AAAAAAAAAAAAAAA

CBMC profiling-(Drop-seq and 10x v2 compatible oligos, containing TruSeq small RNA read 2 handle).
v2_BC1:
SEQ ID NO: 5
/5AmMC12/CCTTGGCACCCGAGAATTCCAATCACGBAA

AAAAAAAAAAAAAAAAAAAAAAAAAAAA v2_BC2:
SEQ ID NO: 6
/5AmMC12/CCTTGGCACCCGAGAATTCCAC

GATGTBAAAAAAAAAAAAAAAAAAAAAAAAAAAAA

AAAA v2_BC3:
SEQ ID NO: 7
/5AmMC12/CCTTGGCACCCGAGAATTCCAT

TAGGCBAAAAAAAAAAAAAAAAAAAAAAAAAAAAAA v2_BC4:
SEQ ID NO: 8
/5AmMC12/CCTTGGCACCCGAGAATTC

CATGACCABAAAAAAAAAAAAAAAAAAAAAAAAAAA

AAAA v2_BC6:
SEQ ID NO: 9
/5AmMC12/CCTTGGCACCCGAGAATTCCAGC

CAATBAAAAAAAAAAAAAAAAAAAAAAAAAAAAAAA v2_BC9:
SEQ ID NO: 10
/5AmMC12/CCTTGGCACCCGAGAATTCC

AGATCAGBAAAAAAAAAAAAAAAAAAAAAAAAAAAA

AAA

-continued v2_BC10:
SEQ ID NO: 11
/5AmMC12/CCTTGGCACCCGAGAATTCC
ATAGCTTBAAAAAAAAAAAAAAAAAAAAAAAAAAA
AAA v2_BC12:
SEQ ID NO: 12
/5AmMC12/CCTTGGCACCCGAGAATT
CCACTTGTABAAAAAAAAAAAAAAAAAAAAAAAAAA
AAAAA v2_BC8:
SEQ ID NO: 13
/5AmMC12/CCTTGGCACCCGAGAATTCC
AACTTGABAAAAAAAAAAAAAAAAAAAAAAAAAAA
AAA v2_BC11:
SEQ ID NO: 14
/5AmMC12/CCTTGGCACCCGAGAATTCC
AGGCTACBAAAAAAAAAAAAAAAAAAAAAAAAAAA
AAA v2_BC13:
SEQ ID NO: 15
/5AmMC12/CCTTGGCACCCGAGAATTCC
AAGTCAABAAAAAAAAAAAAAAAAAAAAAAAAAAAA v2_BC14:
SEQ ID NO: 16
/5AmMC12/CCTTGGCACCCGAGAATTCC
AAGTTCCBAAAAAAAAAAAAAAAAAAAAAAAAAAA v2_BC5:
SEQ ID NO: 17
/5AmMC12/CCTTGGCACCCGAGAATTCC
AACAGTGBAAAAAAAAAAAAAAAAAAAAAAAAAAAAAAA Cell 'Staining' with DNA-Barcoded Antibodies for CITE-Seq.

Roughly 500,000 cells were resuspended in cold PBS containing 2% BSA and 0.01% Tween and filtered through 40 µm cell strainers (Falcon, USA) to remove potential clumps and large particles. Cells were then incubated for 10 minutes with Fc receptor block (TruStain FcX, BioLegend, USA) to block nonspecific antibody binding. Subsequently, cells were incubated with mixtures of barcoded antibodies for 30 min at 4° C. Antibody concentrations were 1 µg per test, as recommended by the manufacturer (BioLegend, USA) for flow cytometry applications. Cells were washed 3× by resuspension in PBS containing 2% BSA and 0.01% Tween, followed by centrifugation (~480 g 5 min at 4° C.) and supernatant exchange. After the final wash, cells were resuspended at appropriate cell concentration in PBS for Drop-seq1 or 10× Genomics3 applications.

CITE-Seq on Drop-Seq Platform.

Drop-seq was performed as described with modifications. For the human/mouse mixing experiment, cells were loaded at a concentration of 400 cells/µL, to achieve a high doublet rate. For PBMC experiments, cells were loaded at 150 cells/µL. cDNA was amplified for ten cycles, and products were then size separated with Ampure Beads (Beckman Coulter, USA) into <300 nt fragments containing antibody-derived tags (ADTs) and >300 nt fragments containing cDNAs derived from cellular mRNA. ADTs were amplified for ten additional cycles using specific primers that append P5 and P7 sequences for clustering on Illumina flowcells. Alternatively, antibody tags can be amplified directly from thoroughly washed Dropseq beads after RNA-cDNA amplification using specific primers for the antibody oligo and Drop-seq bead-RT oligo. cDNAs derived from mRNA were converted into sequencing libraries by tagmentation as described[1]. After quantification, libraries were merged at desired concentrations (10% of a lane for ADT, 90% cDNA library). Sequencing was performed on a HiSeq 2500 Rapid Run with v2 chemistry per manufacturer's instructions (Illumina, USA).

CITE-Seq on 10× Platform.

The 10× single-cell run was performed according to the manufacturer's instructions (10× Genomics, USA) with modifications. For the human/mouse mixing experiment (run on Single Cell 3' version 1) ~17,000 cells were loaded to yield ~10,000 cells with an intermediate/high doublet rate. For CBMC profiling (run on Single Cell 3' version 2), ~7,000 cells were loaded to obtain a yield of ~4,000 cells. For CBMC profiling we spiked-in mouse cells at low frequency (~4%). This allowed us to draw antibody signal-to-noise cutoffs and to estimate the true doublet rates (4%) in our experiments and compare these rates to the estimates provided by the equipment manufacturer (~3.1%) (see below). cDNA was amplified for ten cycles, and products were then size separated with Ampure Beads (Beckman Coulter, USA) into <300 nt fragments containing antibody-derived tags (ADTs) and >300 nt fragments containing cDNAs derived from cellular mRNA. ADTs were amplified for ten additional cycles using specific primers that append P5 and P7 sequences for clustering on Illumina flowcells. A sequencing library from cDNAs derived from RNA was generated using a tagmentation-based approach akin to that used in Drop-seq for the Single Cell 3' v1 experiments, or according to manufacturer's instructions for the Single Cell 3' v2 experiments. ADT and cDNA libraries were merged and sequenced as described above.

Cell Culture.

HeLa (human), 4T1 (mouse) and 3T3 (mouse) cells were maintained according to standard procedures in Dulbecco's Modified Eagle's Medium (Thermo Fisher, USA) supplemented with 10% fetal bovine serum (FBS, Thermo Fisher, USA) at 37° C. with 5% CO2. For the species mixing experiment, HeLa and 4T1 cells were mixed in equal proportions and incubated with DNA barcoded CITE-seq antibodies as described above. For the low frequency mouse spike-ins, ~5% 3T3 cells were mixed into CBMC pool before performing CITE-seq.

Blood Mononuclear Cells.

Cord blood mononuclear cells (CBMCs) were isolated from cord blood (New York Blood Center) as described[57]. Cells were kept on ice during and after isolation. Peripheral blood mononuclear cells were obtained from Allcells (USA).

Comparing Flow Cytometry and CITE-Seq.

Cells were stained with a mixture of fluorophore (CD8a-FITC, BioLegend, USA) labeled antibodies and CITE-seq oligo-labeled antibodies from the same monoclonal antibody clone (RPA-T8) targeting CD8a, at concentrations recommended by the manufacturer (1 ug per test, BioLegend, USA). Cells were also stained with Anti-CD4-APC antibody (RPA-T4, BioLegend, USA). Cells were sorted into pools of different CD8a expression levels using the Sony SH800 cell sorter, which was operated per manufacturer's instructions. Pools were then split into two and reanalyzed by flow cytometry using Sony SH800 or processed for CITE-seq using Drop-seq as described above. Flow cytometry data were plotted using FlowJo v9 (USA).
Multiparameter Flow Cytometry.

Cells were stained with the following mouse anti-human antibodies, which were purchased from BD Biosciences (USA). Antibodies, clones and fluorophores used were CD3e (clone SK7) Hilyte 750 Allophycocyanin (H7APC), CD4 (clone SK3) Brilliant Blue (BB) 630, CD8a (clone SK1) Phycoerythrin (PE), CD14 (clone M5E2) Brilliant Violet (BV) 750, CD19 (clone HIB19) BV570, CD11c (clone B-ly6) Cyanin5 PE, CD2 (clone RPA-2.10) Brilliant Ultraviolet (BUV) 805, and CD57 (clone, NK-1) BB790. After washing cells in PBS and fixing them in 0.5% paraformaldehyde, samples were acquired on a BD Symphony A5 flow cytometer and data was analyzed using FlowJo v9 (USA).
Computational Methods.

Single-cell RNA data processing and filtering. The raw Drop-seq data were processed with the standard pipeline (Drop-seq tools version 1.12 from McCarroll lab). 10× data from the species mixing experiment were processed using Cell Ranger 1.2 using default parameters, and no further filtering was applied. 10× data from CBMC experiments (v2 chemistry) were processed using the same pipeline as used for our Drop-seq data. Reads were aligned to the human reference sequence GRCh37/hg19 (CD8a FACS comparison) or to an hg19 and mouse reference mm10 concatenation (species mixing experiment, CBMCs).

Drop-seq data of the species mixing experiment were filtered to contain only cells with at least 500 UMIs mapping to human genes or 500 UMIs mapping to mouse genes. For the CD8a FACS comparison data, we kept only cells with PCT USABLE BASES >0.5 (fraction of bases mapping to mRNA, this is part of the metrics output by the default processing pipeline). We further removed any cells with less than 200 genes detected and cells with a total number of UMIs or genes (in log 10 after adding a pseudocount) that is more than 3 s.d. above or below the mean. The same filtering strategy was used for the CBMC data, the only difference being a gene threshold of 500.
Single-Cell ADT Data Processing and Filtering.

Antibody and cell barcodes were directly extracted from the reads in the fastq files. Since the antibody barcodes were sufficiently different in the species mixing experiment, we also counted sequences with Hamming distance less than 4. For the CBMCs we counted sequences with Hamming distance less than 2. Reads with the same combination of cellular, molecular and antibody barcode were only counted once. We kept only cells that passed the RNA-specific filters and had a minimum number of total ADT counts (minimum counts used: species mixing, 10; CD8a FACS comparison, 1; CBMC, 50).
CBMC RNA Normalization and Clustering.

After read alignment and cell filtering, we assigned the species to each cell barcode. If more than 90% of UMI counts were coming from human genes, the cell barcode was considered to be human. If it was less than 10% of UMI counts, the assigned species was mouse. Cell barcodes in between 10% and 90% human were considered mixed species. The resulting assignment was 8,005 human, 579 mouse, 33 mixed. Unless stated otherwise, analysis was performed on only the human cells and genes from the human reference genome.

We converted the matrix of UMI counts into a log-normalized expression matrix x with $$xi,j=\log \{cij \times 10,1000/mj\}$$

where cij is the molecule count of gene i in cell j, and mj is the sum of all molecule counts for cell j. After normalization each gene was scaled to have mean expression 0 and variance 1.

We identified 556 highly variable genes by fitting a smooth line (LOESS, span=0.33, degree=2) to log 10(var (UMIs)/mean(UMIs)) as a function of log 10(mean(UMIs)) and keeping all genes with a standardized residual above 1 and a detection rate of at least 1%.

To cluster the cells, we performed dimensionality reduction followed by modularity optimization. We ran principal component analysis (PCA) using the expression matrix of variable genes. To determine the number of significant dimensions, we looked at the percent change in successive eigenvalues. The last eigenvalue to feature a reduction of at least 5% constituted our significant number of dimensions (in this case the number was 13). For clustering we used a modularity optimization algorithm that finds community structure in the data[57]. The data are represented as a weighted network with cells being nodes and squared Jaccard similarities as edge weights (based on Euclidian distance of significant PCs and a neighborhood size of 40 (0.5% of all cells)). The clustering algorithm, as implemented in the "cluster_louvain" function of the igraph R package, find a partitioning of the cells with high density within communities as compared to between communities. For 2D visualization we further reduced the dimensionality of the data to 2 using t-SNE[58,34,59].

CBMC antibody-derived tag normalization and clustering. Since each ADT count for a given cell can be interpreted as part of a whole (all ADT counts assigned to that cell), and there are only 13 components in this experiment, we treated this data type as compositional data and applied the centered log ratio (CLR) transformation[61]. Explicitly, we generated a new CLR-transformed ADT vector y for each cell where $$y=clr(x)=[\ln((x1/g(x)), \ln((x2/g(x)), \ldots \ln((x5/g(x)))],$$

and x is the vector of ADT counts (including one pseudo-count for each component), and g(x) is the geometric mean of x.

We noticed that the ADT counts were on slightly different scales for the different antibodies, which was perhaps caused by differences in antibody specificity and/or epitope abundance. To compensate for the resulting shifts in the nonspecific baseline ADT signal, we examined the density distribution of the CLR-transformed ADT counts of all antibodies separately for human and mouse cells. For each ADT we determined the mean and variance of the mouse cells and defined the species-independent cutoff (separating 'off' state from 'on' state where protein is present) to be one s.d. larger than the mean.

To cluster cells based on ADT counts, the same general approach as for the RNA data was taken, except no dimensionality reduction was performed. Instead we subtracted the mouse-derived cutoffs from the CLR-transformed ADT counts for each antibody. Cell-to-cell weights were squared Jaccard similarities based on Euclidean distance and neighborhood size of 0.5% of the total number of cells.
Estimation of Doublet Rate Using Low Frequency Mouse Spike-in.

Spiking-in mouse cells at low frequency allowed us to estimate the true doublet rates (4%) in our CMBC profiling experiment and compare these to the estimates provided by the equipment manufacturer (~3.1%). For estimation of the doublet rate in our experiments, we modeled the droplet cell capture process as a Poisson distribution with a loading rate lambda and a fixed mouse fraction of 6.5%. We optimized lambda so that simulated data would most closely match the observed species distribution. The resulting lambda was 0.068, and the doublet rate (fraction of droplets with more than one cell of all droplets with at least one cell) observed in the simulations was 4%.

Example 3: Identification of Different Species in Mixing Sample

Figure 1B:
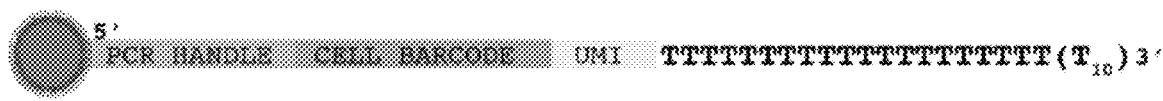
Figure 1C:
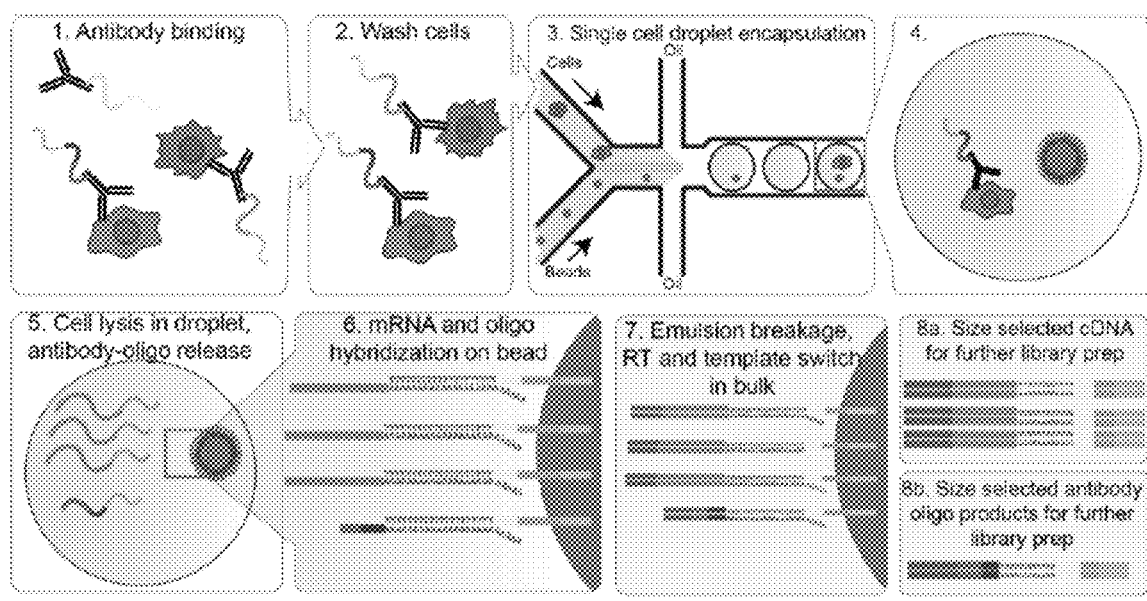

The antibody-oligo complexes described in Example 1 were incubated with cells using conditions established for flow cytometry, such as ref 22. The cells were washed to remove unbound antibodies, then single cells were encapsulated into nanoliter-sized aqueous droplets in a microfluidic apparatus designed to perform Drop-seq' (FIG. 1C). After cell lysis (which happened immediately in the droplets when the lysis buffer contacted cells), cellular mRNAs annealed to polyT containing Drop-seq beads (FIG. 1B) via their polyA tail (FIG. 1C #6). Oligos from the antibodies also annealed to the Drop-seq beads via their poly-A stretch at the 3' end. A unique Barcode sequence on the Drop-seq bead indexed the transcriptome of each co-encapsulated cell. After breaking the emulsion and removing the oil, reverse transcription extended the Barcoded oligo to create the first-strand cDNA from both mRNA and antibody-derived oligo templates. The cDNA and the antibody-derived tags were separated by size (FIG. 2C) and converted into Illumina-ready libraries independently. The two library types were sequenced together. Due to the advantages of generating libraries separately, relative proportions of the libraries are also tailored to ensure appropriate sequencing depth is obtained.

Figure 2C:
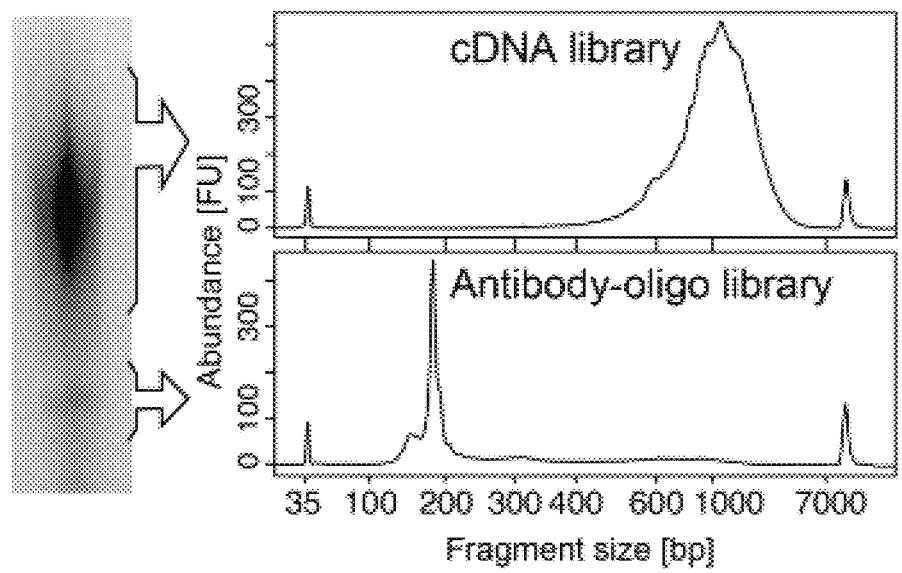
Figure 2D:
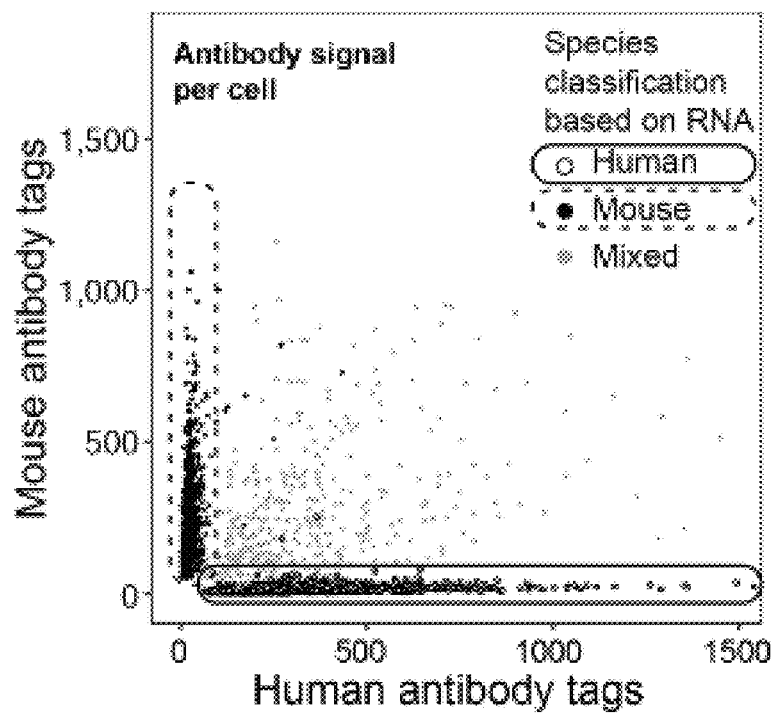
Figure 2E:
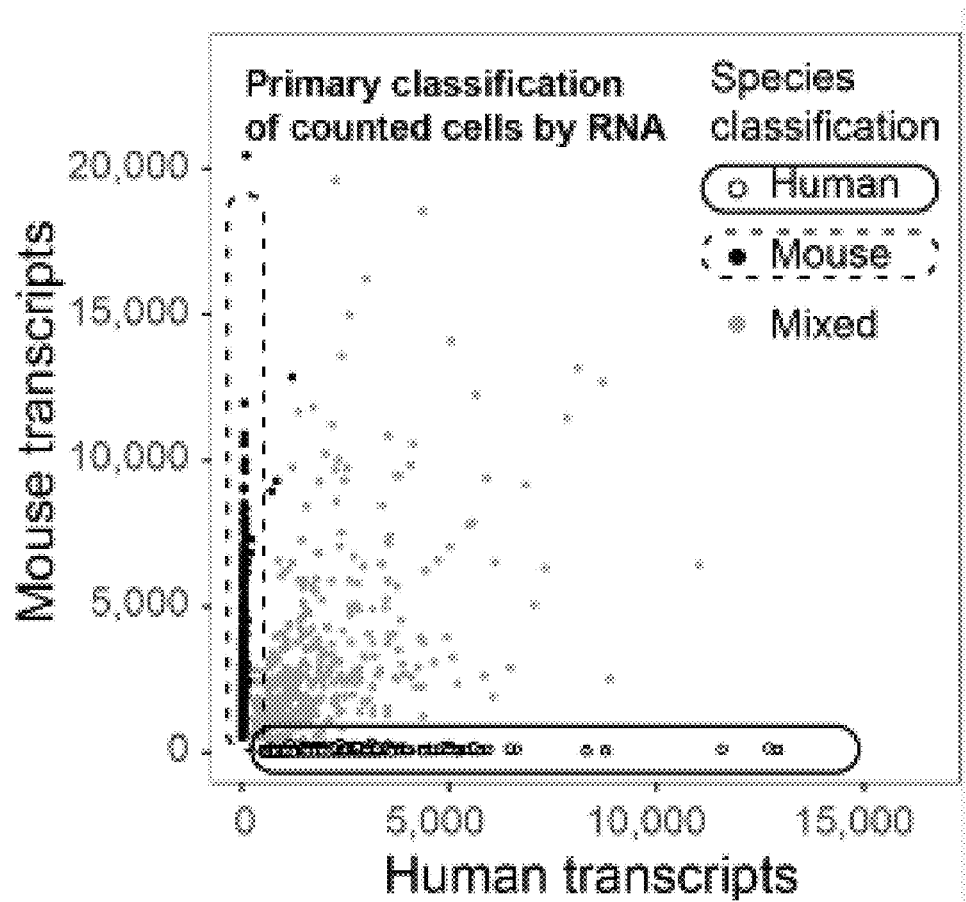

Both cDNA libraries and libraries of recovered oligo tags from antibody-labelled single-cell pools were generated and physically separated before independently preparing libraries for sequencing as shown in FIG. 2C. Sequencing of libraries of recovered oligo tags were performed. All human and all mouse cells in a suspension of hundreds of thousands of mixed human and mouse cells were unambiguously identified based on their species-specific cell-surface proteins (FIG. 2D) after independently using their transcriptome data to identify them (FIGS. 2D and 2E). The vast majority of droplets that were identified as containing either human cells (FIGS. 2D and 2E, circled by solid line), mouse cells (FIGS. 2D and 2E, circled by dashed line) by transcriptome alignment, were also identified as having the same surface-bound species epitopes using the oligo-labelling approach (FIG. 2D).

In this experiment, a high cell concentration was deliberately used to obtain high rates of doublets (droplets containing two or more cells), in order to correlate mixed-species transcriptome data to mixed-species protein signals from individual droplets. See, e.g., FIGS. 2D and 2E, in which the dots not on the axis are mixed signals. Droplets that contained human and mouse cell mixtures also clearly had sequencing reads from both human and mouse antibodies (FIG. 2D, uncircled dots). This result illustrated that signals from multiple antibodies can be obtained from one droplet.

This method is expanded to simultaneously measure large numbers of established antibody-based cell markers and transcriptome in tens of thousands of cells in parallel.

A further experiment yields qualitative cell-surface protein-expression measurements in conjunction with transcriptome-wide expression data. The experiment is performed to confirm that the signal from the oligo on the antibody is reflective of cell-surface epitope concentration. Experimental biases has been identified as coming from the following sources: 1) artificial signal arising from sequencing-library PCR duplicates, 2) cross-reactivity and availability of enough well-characterized antibody species, and 3) variable levels of oligo conjugation to the antibodies leading to inaccurate estimation of epitope concentration.

Methods of correcting the above identified biases include the following. First, PCR duplicates in sequencing datasets are filtered by the use of unique molecular identifiers (UMI) that are built into the design of the Drop-seq oligo. Second, to address antibody cross reactivity, the use of antibodies with low specificity is avoided and only highly optimized and tested flow-cytometry antibodies are used for benchmarking experiments. The optimized antibodies are available from large consortia such as the Human Protein Atlas which are continuously producing more antibodies to supplement the already existing pool of thousands of specific antibodies[7]. Third, the use of streptavidin-biotin conjugation, from the manufacturer's literature, it was estimated that roughly 4-12 oligonucleotide molecules are bound to each antibody molecule.

Different antibody-oligo conjugation strategies, as identified above in the definition for "attachment", for labelling antibodies with a defined number of oligonucleotide molecules are tested in order to obtain a more quantitative measurement. Tagging one oligo molecule to each antibody, together with the use of UMIs, makes the method at least as quantitative as Immuno-PCR-based approaches. For this purpose, evaluations are performed to test whether single-molecule signals can be confidently measured above noise in the final library quantification. The optimal antibody concentration is also determined by titration experiments with individual antibodies as performed in flow cytometry. As a reference standard, the same monoclonal antibodies in a flow-cytometry run using the same cell populations is tested. This allows a determination of sensitivity and quantitative power of the sequencing-based ligonucleotide measurement.

Example 4: Identification of Myeloid and Lymphoid Cell Lineages

Myeloid and lymphoid cell lineages have been extensively studied by cell-surface marker expression in flow cytometry and can be also identified based on their gene-expression profiles. A number of well-established and highly specific flow-cytometry antibodies recognizing global markers for the myeloid and lymphoid lineages and for specific cell subpopulations within these lineages are linked to oligos described in Example 1.

The antibody-oligo complexes generated thereby are incubated with cells using conditions established for flow cytometry. The cells are washed to remove unbound antibodies, then single cells are encapsulated into nanoliter-sized aqueous droplets in a microfluidic apparatus designed to perform Drop-seq' (FIG. 1C). After cell lysis (which happens immediately in the droplets when the lysis buffer contacted cells), cellular mRNAs anneal to polyT containing Drop-seq beads (FIG. 1B) via their polyA tail. Oligos from the antibody anneal to the Drop-seq beads via their poly-A stretch at the 3' end. A unique Barcode sequence on the Drop-seq bead indexes the transcriptome of each co-encapsulated cell. After breaking the emulsion and removing the oil, reverse transcription extends the Barcoded oligo to create the first-strand cDNA from both mRNA and antibody-derived oligo templates. The cDNA and the antibody-derived tags are separated by size, converted into Illumina-ready libraries and sequenced.

Multiple number of antibody-oligo complexes are used to test the multiplexing capability of the method. In a further experiment, more than 100 antibody-oligo complexes are tested.

Example 5: Identification of Cells Based on Protein Expressed Intracellularly Different mild cell permeabilization and fixation procedures that are used for intracellular antibody staining in signaling-specific FACS assays[18] are investigated to determine whether these are compatible with RNA. Antibody-oligo complexes recognizing intracellular proteins are generated as described in Example 1. Furthermore, the established permeabilization and fixation procedure is performed before the incubation step of the CITE-seq protocol. Cells are identified based on protein expressed intracellularly and the mRNAs transcripts. This method not only provides a more detailed characterization of cell populations, but also allows studying post-transcriptional and post-translational gene regulation in single cells at an unprecedented depth.

Example 6: Identification of Cells

The methods described in Examples 1 to 5 are adapted to other droplet- or microwell-based single-cell sequencing technologies as described above. The polyA stretch at the 3' end of the antibody-oligos, allows capture in any oligo-dT-based mRNA-seq protocol, such as that described in Mortazavi et al[23]. The run-specific parameters are evaluated and the utility of the method is assessed for commercially-available instruments (e.g., 10x Genomics) and other technologies that are under development[11].

Example 7: Enhanced Cell Clustering and Classification of Cord Blood Mononuclear Cells A CITE-seq analysis was performed on 8,700 mononuclear blood cells labeled with 10 antibody constructs as described herein having the components as set out in Table 2. tSNE (t-distributed Stochastic Neighbor Embedding)[34] and clustering were performed using canonical correlation analysis, which integrates protein and RNA measurements.

TABLE 2

CITE-seq Constructs

| No. | Antibody/ Target | Conjugation chemistry | Cleavable Linker | Amplification Handle | Barcode | Anchor |
|---|---|---|---|---|---|---|
| 1 | Anti-CD3 for target CD3 | SAV | Disulfide | Illumina ® TruSeq ® Small RNA compatible sequence CCTTGGCACCCGAG AATTCCA SEQ ID NO: 18 | ATCACG | 30x A |
| 2 | Anti-CD19 for target CD19 | SAV | Disulfide | Same as for No. 1 | CGATGT | 30x A |
| 3 | Anti-CD4 for target CD4 | SAV | Disulfide | Same as for No. 1 | TGACCA | 30x A |
| 4 | Anti-CD8a for target CD8a | SAV | Disulfide | Same as for No. 1 | GCCAAT | 30x A |
| 5 | Anti-CD56 for target CD56 | SAV | Disulfide | Same as for No. 1 | CTTGTA | 30x A |
| 6 | Anti-CD16 for target CD16 | SAV | Disulfide | Same as for No. 1 | TTAGGC | 30x A |
| 7 | Anti-CD11c for target CD11c | SAV | Disulfide | Same as for No. 1 | TAGCTT | 30x A |
| 8 | Anti-CD34 for target CD34 | SAV | Disulfide | Same as for No. 1 | GGCTAC | 30x A |

TABLE 2-continued

CITE-seq Constructs

| No. | Antibody/ Target | Conjugation chemistry | Cleavable Linker | Amplification Handle | Barcode | Anchor |
|---|---|---|---|---|---|---|
| 9 | Anti-CD14 for target CD14 | SAV | Disulfide | Same as for No. 1 | AGTCAA | 30x A |
| 10 | Anti-CD10 for target CD10 | SAV | Disulfide | Same as for No. 1 | AGTTCC | 30x A |

Figure 3A:
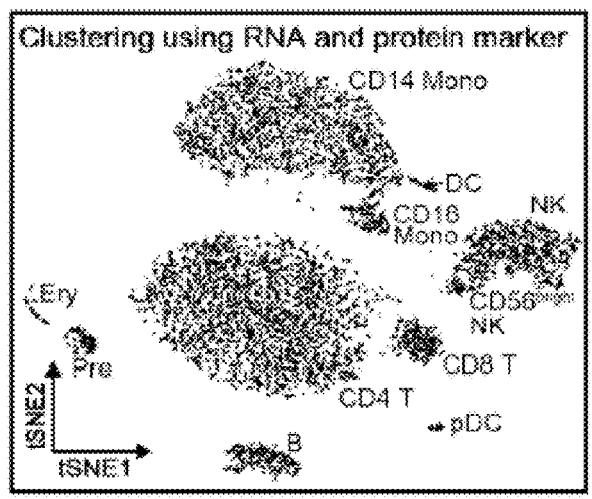
FIG. 3A is a plot displaying the results of a CITE-seq analysis of 8,700 mononuclear blood cells labeled with 10 CITE-seq antibody constructs as described herein having the components as set out in Table 2 (See Example 7 below). tSNE (t-distributed Stochastic Neighbor Embedding)' and clustering are performed using canonical correlation analysis, which integrates protein and RNA measurements. These data show that CITE-seq allows enhanced cell clustering and classification of cord blood mononuclear cells.

One result of this analysis is the dot blot of FIG. 3A. This plot shows that CITE-seq allows enhanced cell clustering and classification of cord blood mononuclear cells.

Figure 3B:
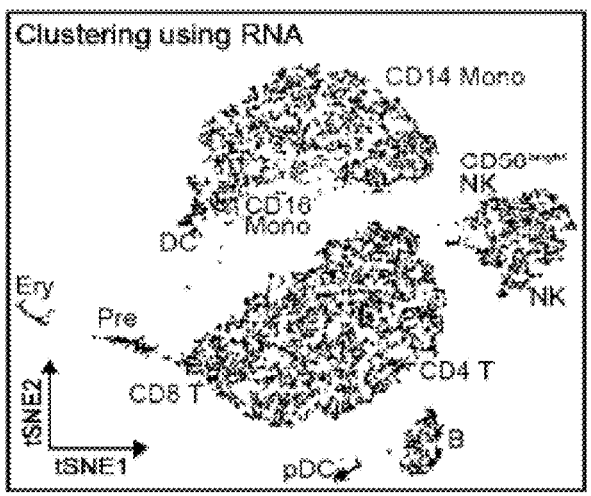
FIG. 3B is a CITE-seq analysis of the same dataset of FIG. 3A using RNA data alone. The symbols in the figure are Mono (for monocytes), B for B cells, T for T cells, NK for natural killer cells, DC for conventional dendritic cells, pDC for plasmacytoid DC, Pre for precursors, and Ery for erythroblasts. Comparing FIG. 3A and FIG. 3B demonstrates enhanced resolution when using multi-modal data.

Another CITE-seq analysis of the same dataset of FIG. 3A was performed using RNA data alone. For example, CD8 and CD4 T cells were not separated into distinct populations. These results are shown in FIG. 3B, in which the dot plot demonstrates enhanced resolution when using multi-modal data. The symbols in the figure are Mono (for monocytes), B for B cells, T for T cells, NK for natural killer cells, DC for conventional dendritic cells, pDC for plasmacytoid DC, Pre for precursors, and Ery for erythroblasts.

Figure 3C:
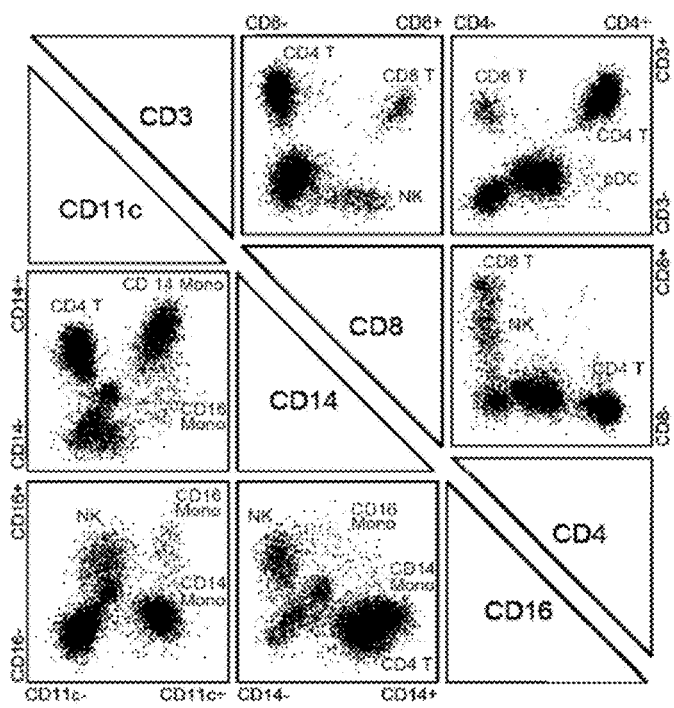
FIG. 3C shows bi-axial plots of CITE-seq antibody data for select antibodies, i.e. Construct Nos. 1, 3, 4, 6, 7, and 9 of Table 2 (See Example 7). These data show that, in contrast to information obtained by flow cytometry, using CITE-seq methodology and compositions makes available the transcriptome for every single cell (every dot) within the plot. Cells can therefore be further analyzed and classified based on their RNA data, protein data, or both.

Finally, the bi-axial plots of CITE-seq antibody data for select antibodies, i.e. Construct Nos. 1-10 of Table 2, are demonstrated in FIG. 3C. The data are comparable to what is obtained by flow cytometry with the significant difference that the transcriptome for every single cell (every dot) within the plot is also available when using the CITE-seq methodology and constructs. Cells can therefore be further analyzed and classified based on their RNA data, protein data, or both.

Figure 4:
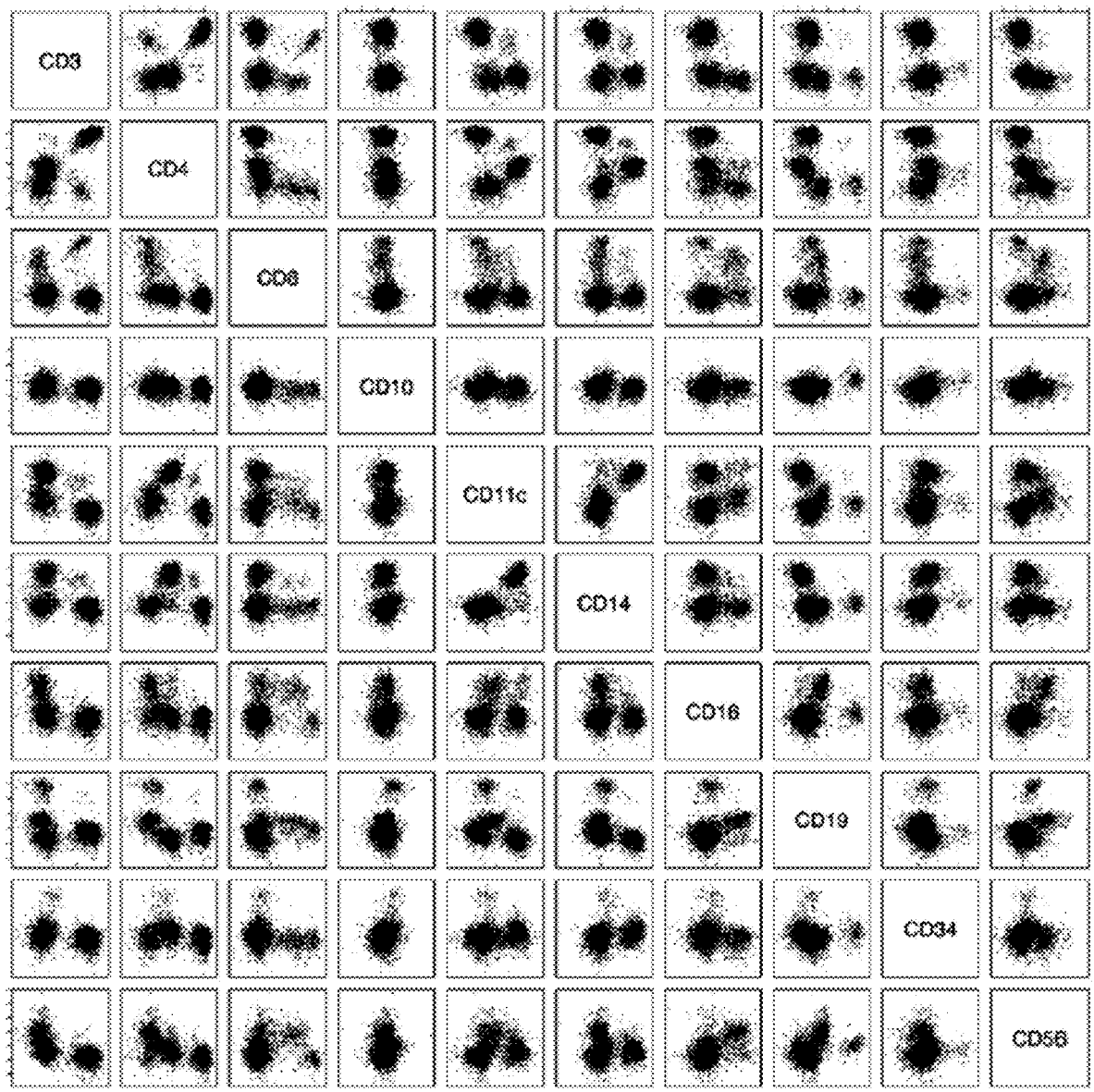
FIG. 4 is a series of bi-axial plots generated by multiplexing 8,700 mononuclear blood cells labeled with the 10 antibody constructs of Table 2 (Example 7) in a CITE-seq analysis as described herein. Shown are bi-axial plots of CITE-seq antibody data for all 10 antibodies. These data are comparable to the information obtained by flow cytometry, using CITE-seq methodology and compositions also makes available the transcriptome for every single cell (every dot) within the plot. Cells can therefore be further analyzed and classified based on their RNA data, protein data, or both.

Another series of bi-axial plots was generated by multiplexing 8,700 mononuclear blood cells labeled with the 10 antibody constructs of Table 2 in a CITE-seq analysis as described above. FIG. 4 shows bi-axial plots of CITE-seq antibody data for all 10 antibody constructs of Table 2. The data is comparable to what is obtained by flow cytometry with the significant difference that the transcriptome for every single cell (every dot) within these plots is also available when using CITE-seq. Cells can therefore be further analyzed and classified based on their RNA data, protein data, or both.

Example 8: Cite SEQ

We describe cellular indexing of transcriptomes and epitopes by sequencing (CITE-seq), a method in which oligonucleotide-labeled antibodies are used to integrate cellular protein and transcriptome measurements into an efficient, single-cell readout. CITE-seq is compatible with existing single-cell sequencing approaches and scales readily with throughput increases. The CITE-seq method combines highly multiplexed protein marker detection with unbiased transcriptome profiling for thousands of single cells. The method is readily adaptable to two high-throughput scRNA-seq applications and shows that multimodal data analysis can achieve a more detailed characterization of cellular phenotypes than transcriptome measurements alone.

We devised a digital, sequencing-based readout for protein levels by conjugating antibodies to oligonucleotides (oligos) that can be captured by oligo-dT primers (used in most scRNA-seq library preparations), contain a barcode for antibody identification and include a handle for PCR amplification. A commonly used streptavidin-biotin interaction links the 5' end of oligos to antibodies. The antibody-oligo complexes are incubated with single-cell suspensions in conditions comparable to flow cytometry staining protocols; after this incubation, cells are washed to remove unbound antibodies and processed for scRNA-seq. In our example, we encapsulated single cells into nanolitersized aqueous droplets in a microfluidic apparatus designed to perform Drop-seq[1]. After cell lysis in droplets, cellular mRNAs and antibody-derived oligos both anneal via their 3' polyA tails to Drop-seq beads containing oligo-dT and are indexed by a shared cellular barcode during reverse transcription. The amplified cDNAs and antibody-derived tags (ADTs) can be separated by size and converted into Illumina-sequencing libraries independently. Importantly, because the two library types are generated separately, their relative proportions can be adjusted in a pooled single lane to ensure that the required sequencing depth is obtained for each library. See, e.g., ref 46, and online data incorporated by reference herein.

To assess our method's ability to distinguish single cells based on surface protein expression, we designed a proof-of-principle 'species-mixing' experiment that leverages the species-specific and highly expressed marker CD29 (Integrin beta-1). A suspension of human (HeLa) and mouse (4T1) cells was incubated with a mixture of DNA-barcoded anti-mouse and anti-human CD29 antibodies. After washing to remove unbound antibodies, we performed Drop-seq[1] to investigate the concordance between species of origin of the transcripts and ADTs. We deliberately used a high cell concentration to obtain high rates of multiplets (droplets containing two or more cells) to correlate mixed-species transcriptome data with mixed-species ADT signals from individual droplets. Most droplets (97.2%) that were identified as containing human, mouse or mixed cells by transcriptome received the same species classification by ADT counts. Cell counts based on RNA or ADT are highly correlated between both methods, and this demonstrates the low dropout rate of ADT signals. We performed the same experiment using a commercially available system from 10× Genomics and obtained comparable results.

We sought to characterize the quantitative nature of the CITEseq protein readout. Flow cytometry is the gold standard for enumerating cell subsets based on quantitative differences in surface markers[47,48]. We therefore aimed to benchmark the sensitivity of CITE-seq protein detection to flow cytometry using CITE-seq antibodies directed against common flow cytometry markers to identify and discriminate immune subpopulations. We performed multiparameter flow cytometry and CITE-seq experiments using the same set of antibodies on aliquots of the same pool of peripheral blood mononuclear cells. Using ADT levels, we were able to construct cytometry-like 'biaxial' gating plots and compare these qualitatively and quantitatively to the flow cytometry data. Cell distribution profiles based on expression of marker proteins associated with various T-cell subsets, B cells, plasmacytoid, myeloid dendritic cells and monocytes were remarkably similar.

Next, we asked whether quantitative differences in expression observed by flow cytometry can be observed by CITE-seq. For this, we focused on the marker CD8a, since its levels vary widely across immune cell populations. We incubated cord blood mononuclear cells (CBMCs) with CITE-seq antibody conjugates and fluorophore-conjugated antibodies, so that some CD8a epitopes on each cell would be labeled by fluorophore and some by oligo. Cells were subjected to fluorescence-activated cell sorting (FACS) into separate pools based on CD8a fluorescence (very high (+++), high (++), intermediate (+) and low (+/−)). Each pool was then split and separately reanalyzed by flow cytometry and CITE-seq. For each pool defined by FACS, similar relative CD8a expression levels were observed by both methods. We conclude that CITE-seq ADT levels are consistent with gold standard flow cytometry and can therefore enable high-resolution immunophenotyping in concert with transcriptomics.

The immune system has been extensively profiled using cell surface markers' and scRNA-seq[3,9,49], and both methods reliably identify the same cell types at consistent proportions. A complex immune cell population is therefore an ideal system for validating the multimodal readout of CITE-seq. We prepared a CITE-seq panel of 13 well-characterized monoclonal antibodies that recognize cell-surface proteins routinely used as markers for immune-cell classification. To estimate nonspecific background antibody binding within experiments, we developed a low-level 'spike-in' control. A rare spiked-in population of murine cells should be easily distinguished transcriptomically but should not cross-react with our anti-human antibodies; this would enable us to define background ADT levels directly from the data. We therefore spiked mouse 3T3 fibroblasts (~4%) into our CBMCs, incubated the cell pool with our CITE-seq antibody panel and ran the 10× Genomics single-cell workflow on a total of 8,005 cells. Unsupervised graph-based clustering using RNA expression revealed recognizable cell types that express select marker genes. Murine cells clustered separately (data not shown) and exhibited low ADT counts for each marker, and this allowed us to set a baseline for signal versus noise to more clearly delineate positive from negative cell populations. Through this thresholding step, we identified three antibody-oligo conjugates with no specific binding (i.e., no signal-over-background threshold) and excluded these from further analysis.

We detected strong ADT enrichment in the correct immune populations—CD3e within the T-cell cluster; CD4 and CD8a in largely nonoverlapping T-cell subpopulations; CD19 almost exclusively in B-cells; CD56, CD16 and CD8a in the NK cluster; and CD11c and CD14 in the monocyte and dendritic cell cluster. We also identified a rare precursor cell population at less than 2% in cord blood (CD34+ cells). Per-cell ADT counts were higher than mRNA levels for the same genes and were less prone to 'dropout' events. Consistent with this, we found low correlations between mRNA and ADT on a single cell basis and higher correlation when averaging expression within clusters. We used the ADT levels and transcriptome-based clustering information to construct multimodal CITE-seq 'biaxial' gating plots; this revealed similar profiles that are well-established by flow cytometry. For example, we could resolve strong anti-correlation of CD4 and CD8a ADT levels in T cells and quantitative differences in marker expression between subsets—these included expression differences of CD8a between NK and T cells or of CD4 between monocytes and T cells. In addition, clustering based on ADT levels results in clear and consistent cell-type separation (see Ref 46 for figures of data not shown).

We next asked whether multimodal data from CITE-seq could enhance the characterization of immune cell phenotypes compared to scRNA-seq alone. We noted an opposing gradient of CD56 and CD16 ADT levels within our transcriptomically derived NK cell cluster, potentially revealing CD56bright and CD56dim subsets[50,51]; therefore, we subdivided our NK cell cluster based on CD56 ADT levels. When comparing the molecular profiles of these groups, we observed protein and RNA changes that were highly consistent with the literature[50,51]. We observed an apparent complementarity between levels of CD16 and to a lesser extent of CD8a ADTs compared with CD56 ADTs within these two subsets. For 11 genes that have previously been characterized as differentially expressed within these subtypes[50-52], we detected upregulation or downregulation consistent with the literature in ten cases, including those of GZMB, GZMK and PRF1. This illustrates the potential for integrated and multimodal analyses to enhance discovery and description of cellular phenotypes, particularly when differentiating between cell populations with subtle transcriptomic differences.

The ability to layer additional molecular measurements on top of scRNA-seq data represents an exciting direction for the single-cell research community. CITE-seq enables multimodal analysis of single cells at the scale afforded by droplet-based single-cell sequencing approaches. We demonstrated the value of multimodal analysis to reveal phenotypes that could not be discovered by using scRNA-seq alone, and we also envision the use of CITE-seq for studies of post-transcriptional gene regulation at the single-cell level. In contrast to flow and mass cytometry, detection of oligo-bar-coded antibodies is not limited by signal collision; a 10-nt sequence can easily encode more barcodes than there are human proteins, and this enables large-scale immunophenotyping with panels of tens to hundreds of antibodies. In addition, mild cell permeabilization and fixation procedures used for intracellular cytometry assays should also be compatible with CITE-seq, and they may significantly expand the number of useful markers.

A modified version of CITE-seq in which only ADTs are analyzed on a massively parallel scale without capturing cellular mRNAs (cytometry by sequencing) can also be envisaged.

Finally, we have shown that the CITE-seq is fully compatible with a commercially available single-cell platform (10× Genomics) and should be readily adaptable to other droplet-, microwell- and combinatorial-indexing-based high-throughput single-cell sequencing technologies[2,54,55,20,30] with either no or minor customizations.

Example 9: Cite-Seq Variations

In one experiment, the CITE-seq readout was compared from different conjugation technologies. One technology used the biotin-streptavidin (SAV) linkage previously described in Examples 1-8. Another method for antibody-oligo conjugation employed covalent conjugation via iEDDA chemistry as described previously[45]. The iEDDA conjugation chemistry used is comparable to conjugation chemistries offered in commercially available kits (Innova Biosciences, Thunderlink PLUS kit).

A CITE-seq analysis was performed on 4000 peripheral blood mononuclear cells (PBMCs) labeled with one of 6 antibody constructs as described herein having the components as set out in Table 3. tSNE (t-distributed Stochastic Neighbor Embedding)[34] and clustering were performed using canonical correlation analysis, which integrates protein and RNA measurements.

TABLE 3

CITE-seq Constructs

| No. | Antibody/ Target | Conjugation chemistry | Amplification Handle | Barcode | Anchor |
|---|---|---|---|---|---|
| 1 | Anti-CD3 for target CD3 | SAV | Illumina ® TruSeq ® SmallRNA compatible sequence CCTTGGCACCCGAGAATTCCA SEQ ID NO: 19 | TTC AGG T SEQ ID NO: 20 | GTG 30x A |
| 2 | Anti-CD3 for target CD3 | covalent | Same as for No. 1 | TCT A SEQ ID NO: 21 | TCG TCC 30x A |
| 3 | Anti-CD4 for target CD4 | SAV | Same as for No. 1 | ATG C SEQ ID NO: 22 | CTC TAC 30x A |
| 4 | Anti-CD4 for target CD4 | covalent | Same as for No. 1 | TAG GCT G SEQ ID NO: 23 | ACA 30x A |
| 5 | Anti-CD8 for target CD8 | SAV | Same as for No. 1 | ATG GTA G SEQ ID NO: 24 | GAG 30x A |
| 6 | Anti-CD8 for target CD8 | covalent | Same as for No. 1 | AGA ACC C SEQ ID NO: 25 | TGA 30x A |

Figure 5A:
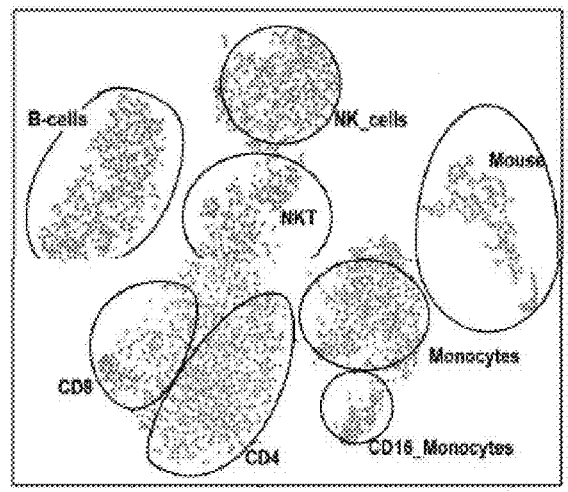
FIG. 5A is a plot showing the RNA clustering of about 4,000 peripheral blood mononuclear cells (PBMC), containing B cells, NK cells, mouse cells, Natural Killer T cells, Monocytes, CD16 Monocytes, CD4 cells and CD8 cells. tSNE (t-distributed Stochastic Neighbor Embedding)[34] and clustering are performed using canonical correlation analysis using RNA expression data.
Figure 5B:
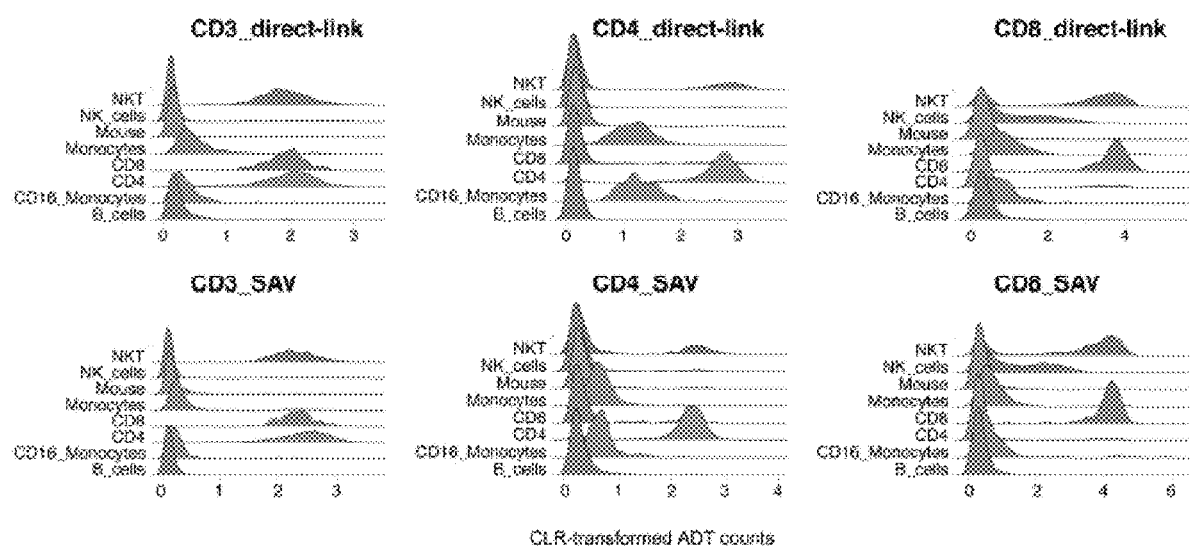
FIG. 5B shows 6 histogram profiles of CLR (centered log ratio)-transformed ADT (antibody derived tag) levels in clusters of B cells, NK cells, mouse cells, Natural Killer T cells, Monocytes, CD16 Monocytes, CD4 cells and CD8 cells exposed to compositions as described in Table 3. One such composition comprises a Ligand which is either an anti-CD3 antibody, anti-CD4 antibody or anti-CD8 antibody, covalently (directly) linked to a polymer construct, in this example a DNA oligonucleotide, containing an Amplification Handle compatible with Illumina Truseq Small RNA, a 10 nucleotide Barcode that is unique to each antibody to identify the Ligand, and a 30 nucleotide polyA tail Anchor for hybridizing to a capture sequence that comprises a sequence complementary to the Anchor. Other such compositions comprises a Ligand which is either an anti-CD3 antibody, anti-CD4 antibody or anti-CD8 antibody, linked via a streptavidin-biotin linkage (SAV) as used in proof of principle experiments (FIGS. 1-4) to a polymer, in this example a DNA oligonucleotide, containing an Amplification Handle compatible with Illumina Truseq Small RNA, a 10 nucleotide Barcode that unique to each antibody to identify the Ligand, and a 30 nucleotide polyA tail Anchor for hybridizing to a capture sequence that comprises a sequence complementary to the Anchor. The histogram profiles in the different populations (e.g., NK cells, CD4, CD8) are comparable between the SAV and direct conjugation.

In the attached FIGS. 5A and 5B, the profiles (histograms) in different populations (e.g. NK cells, CD4, CD8) look comparable in the SAV and direct conjugation.

Example 10: Variations in Use of Cite-Seq Constructs

Despite rapid developments in single-cell sequencing technology, sample-specific batch effects, detection of cell doublets, and the cost of generating massive datasets remain outstanding challenges. Here, we introduce cell "hashing", where oligo-tagged antibodies against ubiquitously expressed surface proteins are used to uniquely label cells from distinct samples, which can be subsequently pooled. By sequencing these tags alongside the cellular transcriptome, we can assign each cell to its sample of origin, and robustly identify doublets originating from multiple samples. We demonstrate our approach by pooling eight human PBMC samples on a single run of the 10× Chromium system, substantially reducing our per-cell costs for library generation. Cell "hashing" is inspired by, and complementary to, elegant multiplexing strategies based on genetic variation", which we also leverage to validate our results. We therefore envision that our approach will help to generalize the benefits of single-cell multiplexing to diverse samples and experimental designs.

Single-cell genomics offers enormous promise to transform our understanding of heterogeneous processes and to reconstruct unsupervised taxonomies of cell types[63,64]. As studies have progressed to profiling complex human tissues[65,66] and even entire organisms,[20,67] there is a growing appreciation of the need for massively parallel technologies and datasets to uncover rare and subtle cell states.[1-3] While the per-cell cost of library prep has dropped, routine profiling of tens to hundreds of thousands of cells remains costly both for individual labs, and for consortia such as the Human Cell Atlas[68]. Broadly related challenges also remain, including the robust identification of artifactual signals arising from cell doublets or technology-dependent batch effects[69].

In particular, reliably identifying expression profiles corresponding to more than one cell (hereby referred to as 'multiplets') remains an unsolved challenged in single cell RNA-seq (scRNA-seq) analysis, and a robust solution would simultaneously improve data quality and enable increased experimental throughput. While multiplets are expected to generate higher complexity libraries compared to singlets, the strength of this signal is not sufficient for unambiguous identification[69]. Similarly, technical and "batch" effects have been demonstrated to mask biological signal in the integrated analysis of scRNA-seq experiments[70], necessitating experimental solutions to mitigate these challenges.

Recent developments have poignantly demonstrated how sample multiplexing can simultaneously overcome multiple challenges.[71,72] For example, the demuxlet[71] algorithm enables the pooling of samples with distinct genotypes together into a single scRNA-seq experiment. Here, the sample-specific genetic polymorphisms serve as a fingerprint for the sample of origin, and therefore can be used to assign each cell to an individual after sequencing. This workflow also enables the detection of multiplets originating from two individuals, reducing nonidentifiable multiplets at a rate that is directly proportional to the number of multiplexed samples. While this elegant approach requires pooled samples to originate from previously genotyped individuals, in principle any approach assigning sample fingerprints that can be measured alongside scRNA-seq would enable a similar strategy. For instance, sample multiplexing is frequently utilized in flow and mass cytometry by labeling distinct samples with antibodies to the same ubiquitously expressed surface protein, but conjugated to different fluorophores or isotopes, respectively[73,74].

We recently introduced CITE-seq[46], where oligonucleotide-tagged antibodies are used to convert the detection of cell-surface proteins into a sequenceable read-out alongside scRNA-seq. We reasoned that a defined set of oligo-tagged antibodies against ubiquitous surface proteins could uniquely label different experimental samples. This enables us to pool these together, and use the barcoded antibody signal as a fingerprint for reliable demultiplexing. We refer to this approach as cell "hashing", as our set of oligos defines a "look up table" to assign each multiplexed cell to its original sample. We demonstrate this approach by labeling and pooling eight human PBMC samples, and running them simultaneously in a single droplet based scRNA-seq run. Cell hashtags allow for robust sample multiplexing, confident multiplet identification, and the discrimination of low-quality cells from ambient RNA. In addition to enabling "super-loading" of commercial scRNA-seq platforms to substantially reduce costs, this strategy represents a generalizable approach for doublet identification and multiplexing that can be tailored to any biological sample or experimental design.

Figure 6A:
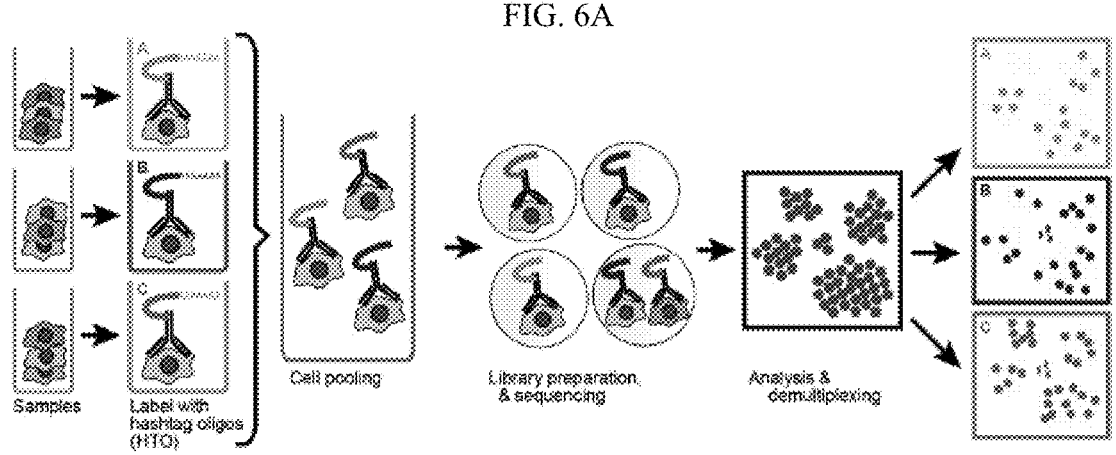
FIGS. 6A-6F show sample multiplexing using DNA-barcoded antibodies.

A. Hashtag-Enabled Demultiplexing Based on Ubiquitous Surface Protein Expression We sought to extend antibody-based multiplexing strategies[73,74] to scRNA-seq using a modification of our CITE-seq method. We chose a set of monoclonal antibodies directed against ubiquitously and highly expressed immune surface markers (CD45, CD98, CD44, and CD11a), combined these antibodies into eight identical pools (pool A through H), and subsequently conjugated each pool to a distinct hashtag oligonucleotide (henceforth referred to as HTO, FIG. 6A). The HTOs contain a unique 12-bp barcode that can be sequenced alongside the cellular transcriptome, with only minor modifications to standard scRNA-seq protocols. We utilized an improved and simplified conjugation chemistry compared to our previous approach using iEDDA click chemistry to covalently attach oligonucleotides to antibodies[45].

We designed our strategy to enable CITE-seq and cell "hashing" to be performed simultaneously, but to generate separate sequencing libraries. Specifically, the HTOs contain a different amplification handle than our standard CITE-seq antibody derived tags (ADT). This allows HTOs, ADTs, and scRNA-seq libraries to be independently amplified and pooled at desired quantities. Notably, we have previously observed robust recovery of antibody signals from highly expressed epitopes due to their extremely high copy number. This is in contrast to the extensive "drop-out" levels observed for scRNA-seq data, and suggests that we can faithfully recover HTOs from each single cell, enabling assignment to sample of origin with high fidelity.

To benchmark our strategy and demonstrate its utility, we obtained PBMCs from eight separate human donors (referred to as donors A through H), and independently stained each sample with one of our HTO-conjugated antibody pools, while simultaneously performing a titration experiment with a pool of seven immunophenotypic markers for CITE-seq. We subsequently pooled all cells together in equal proportion, alongside an equal number of unstained HEK-293T cells (and 3% mouse NIH-3T3 cells) as negative controls, and ran the pool in a single lane on the 10× Genomics Chromium Single Cell 3' v2 system. Following the approach in Kang et al[71], we "super-loaded" the 10× Genomics instrument, loading cells at a significantly higher concentration with an expected yield of 20,000 single cells and 5,000 multiplets. Based on Poisson statistics, 4,365 multiplets should represent cell combinations from distinct samples and can potentially be discarded, leading to an unresolved multiplet rate of 3.1%. Notably, achieving a similar multiplet rate without multiplexing would yield ~4,000 singlets. As the cost of commercial droplet-based systems is fixed per run, multiplexing therefore allows for the profiling of ~400% more cells for the same cost.

We performed partitioning and reverse transcription according standard protocols, utilizing only a slightly modified downstream amplification strategy to generate transcriptome, HTO, and ADT libraries. We pooled and sequenced these on an Illumina HiSeq2500 (two rapid run flowcells), aiming for a 90%:5%:5% contribution of the three libraries in the sequencing data. Additionally, we performed genotyping of all eight PBMC samples and HEK-293T cells with the Illumina Infinium CoreExome array, allowing us to utilize both HTOs and sample genotypes (assessed by demuxlet[71]) as independent demultiplexing approaches.

Figure 6B:
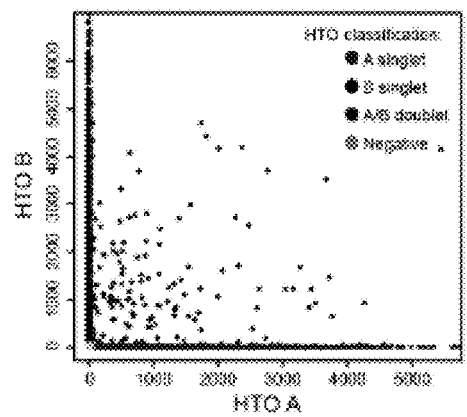
Figure 6C:
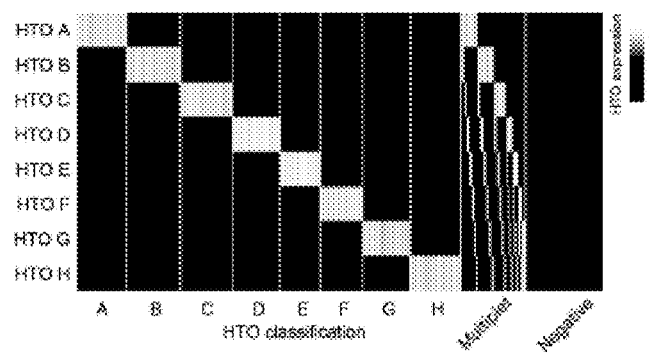
Figure 6D:
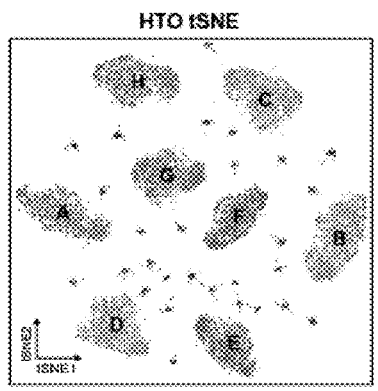
Figure 6E:
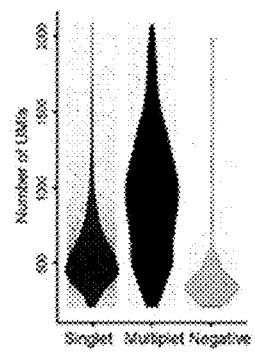
Figure 6F:
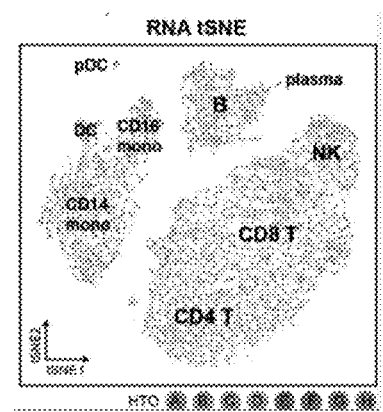

When examining pairwise expression of two HTO counts, we observed relationships akin to "species-mixing" plots (FIG. 6B), suggesting mutual exclusivity of HTO signal between singlets. Extending beyond pairwise analysis, we developed a straightforward statistical model to classify each barcode as "positive" or "negative" for each HTO. Briefly, we modeled the "background" signal for each HTO independently as a negative binomial distribution, estimating background cells based on the results of an initial k-medoids clustering of all HTO reads. Barcodes with HTO signals above the 99% quantile for this distribution were labeled as "positive", and barcodes that were "positive" for more than one HTO were labeled as multiplets. We classified all barcodes where we detected at least 200 RNA UMI, regardless of HTO signal. Our classifications (visualized as a heatmap in FIG. 6C) suggested clear identification of eight singlet populations, as well as multiplet groups. We also identified barcodes with negligible background signal for any of the HTOs (labeled as "negatives"), consisting primarily (87.5%) of HEK and mouse cells. We removed all HEK and mouse cells from downstream analyses, with the remaining barcodes representing 13,964 singlets, and 2,463 identifiable multiplets, in line with expectations. Our classifications were also fully concordant with a tSNE embedding, calculated using only the eight HTO signals, which enabled the clear visualization not only of the 8 groups of singlets (donors A through H), but also the 28 small groups representing all possible doublet combinations (FIG. 6D). Moreover, we observed a clear positive shift in the distribution of RNA UMI/barcode for multiplets, as expected (FIG. 6E), while the remaining negative barcodes expressed fewer UMIs and may represent failed reactions or "empty" droplets containing only ambient RNA. These results strongly suggest that HTOs successfully assigned each barcode into its original sample, and enabled robust detection of cross-sample multiplets. Performing transcriptomic clustering of the classified singlets enabled clear detection of nine hematopoietic subpopulations, which were interspersed across all eight donors (FIG. 6F).

B. Genotype-Based Demultiplexing Validates Cell "Hashing"

Figure 7A:
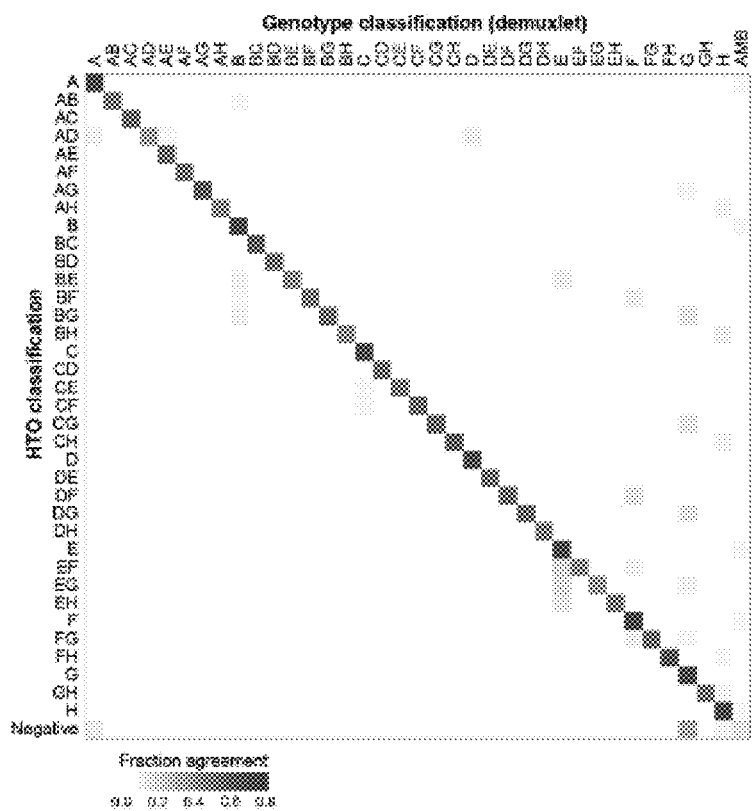
FIGS. 7A-7E show the validation of cell "hashing" using demuxlet.
Figure 7B:
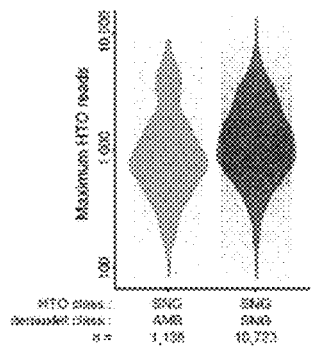
Figure 7C:
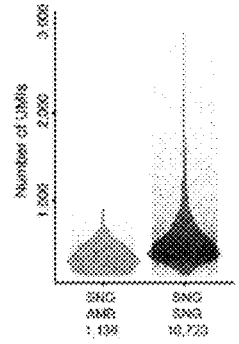

We next compared our HTO-based classifications to those obtained by demuxlet[71]. Overall we observed strong concordance between the techniques, even when considering the precise sample mixture in called doublets (FIG. 7A). Exploring areas of disagreement, we identified 1,138 barcodes that were classified based on HTO levels as singlets, but were identified as "ambiguous" by demuxlet. Notably, the strength of HTO classification for these discordant barcodes (represented by the number of reads assigned to the most highly expressed HTO) was identical to barcodes that were classified as singlets by both approaches (FIG. 7B). However, discordant barcodes did have reduced RNA UMI counts (FIG. 7C). We conclude that these barcodes likely could not be genetically classified at our shallow sequencing depth, which is below the recommended depth for using demuxlet, but likely represent true single cells based on our HTO classifications.

Figure 7D:
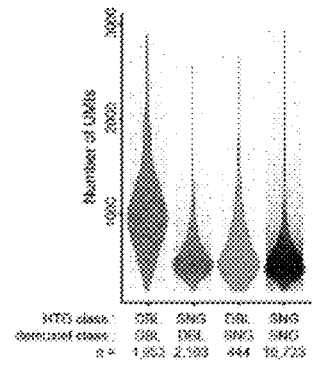
Figure 7E:
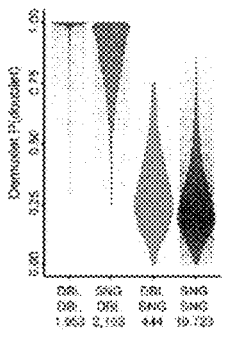

In addition, we also observed 2,547 barcodes that received discordant singlet/doublet classifications between the two techniques (FIG. 7D). We note that this does reflect a minority of barcodes (compared to 12,676 concordant classifications), and that in these discordant cases it is difficult to be certain which of these methods is correct. However, when we examined the UMI distributions of each classification group, we observed that only barcodes classified as doublets by both techniques exhibited a positive shift in transcriptomic complexity (FIG. 7D). This suggests that these discordant calls are largely made up of true singlets, but represent conservative false positives from both methods, perhaps due to ambient RNA or HTO signal. Consistent with this interpretation, when we restricted our analysis to cases where demuxlet called barcodes as doublets with >95% probability, we observed a 71% drop in the number of discordant calls (FIG. 7E).

C. Cell Hashing Enables the Efficient Optimization of CITE-Seq Antibody Panels

Our multiplexing strategy not only enables pooling across donors, but also the simultaneous profiling of multiple experimental conditions. This is widely applicable for simultaneous profiling of diverse environmental and genetic perturbations, but we reasoned that we could also efficiently optimize experimental workflows, such as the titration of antibody concentrations for CITE-seq experiments. In flow cytometry, antibodies are typically run individually over a large dilution series to assess signal to noise ratios and identify optimal concentrations[75]. While such experiments would be extremely cost prohibitive if run as individual 10× Genomics lanes, we reasoned that we could multiplex these experiments together using cell "hashing".

Figure 8A:
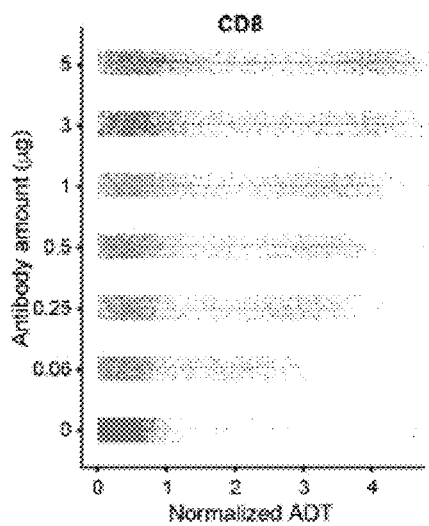
FIGS. 8A-8F show that cell "hashing" enables efficient experimental optimization and identification of low-quality cells.
Figure 8B:
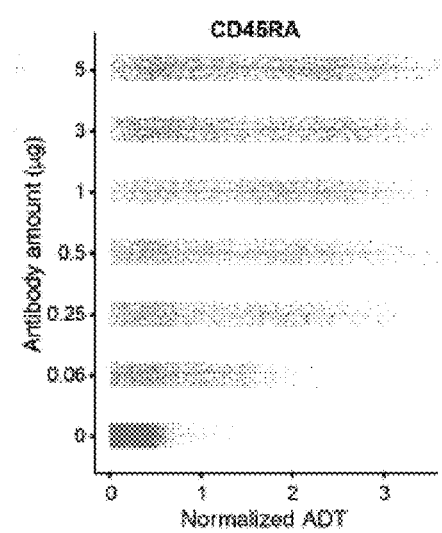
Figure 8C:
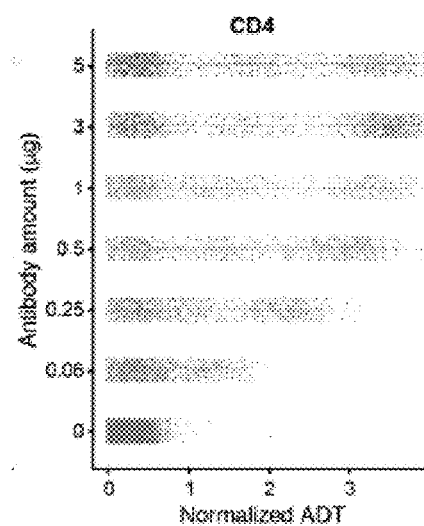
Figure 8D:
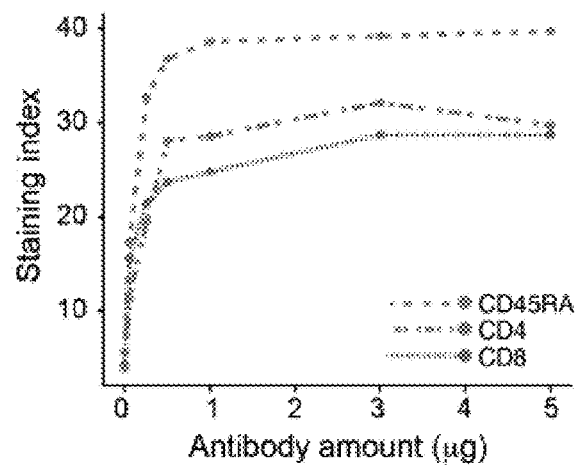

We therefore incubated the PBMCs from different donors with a dilution series of antibody concentrations ranging over three orders of magnitude. Concentrations of CITE-seq antibodies were staggered between the different samples to keep the total amount of antibody and oligo consistent in each sample. After sample demultiplexing, we examined ADT distributions across all concentrations for each antibody (examples in FIGS. 8A-8C), and assessed signal-to-noise ratio by calculating a staining index similar to commonly used metrics for flow cytometry optimization (FIG. 8D).

All antibodies exhibited only background signal in the negative control conditions, and very weak signal-to-noise at 0.06 µg/test. We observed that the signal-to-noise ratio for most antibodies began to saturate within the concentration range of 0.5 to 1 µg/test, comparable to the recommended concentrations for flow cytometry (FIG. 8D). This experiment was meant as a proof-of-concept; an ideal titration experiment would use cells from the same donor for all conditions and a larger range of concentrations, but clearly demonstrates how cell "hashing" can be used to rapidly and efficiently optimize experimental workflows.

D. Cell Hashtags Enable the Discrimination of Low Quality Cells from Ambient RNA Our cell hashtags can discriminate single cells from doublets based on the clear expression of a single HTO, and we next asked whether this feature could also distinguish low quality cells from ambient RNA. If so, this would enable us to reduce our UMI "cutoff" (previously set at 200), and would allow for the possibility that certain barcodes representing ambient RNA may express more UMI than some true single cells. Most workflows set stringent UMI cutoffs to exclude all ambient RNA, biasing scRNA-seq results against cells with low RNA content, and likely skewing proportional estimates of cell type.

Figure 8E:
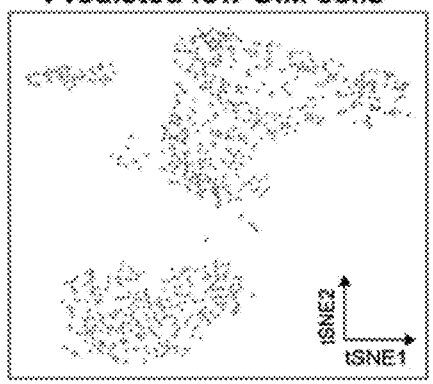
Figure 8F:
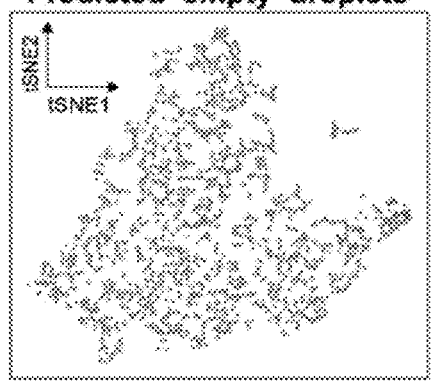

Indeed, when considering 3,473 barcodes containing 50-200 UMI, we recovered 954 additional singlets based on HTO classifications, with 2,432 barcodes characterized as negatives. We classified each barcode as one of our previously determined nine hematopoietic populations (FIG. 6F), and visualized the results on a transcriptomic tSNE embedding, calculated independently for both "singlet" and "negative" groups. For predicted singlets, barcodes projected to B, NK, T, and myeloid populations which were consistently separated on tSNE, suggesting that these barcodes represent true single cells (FIG. 8E). In contrast, 'negative' barcodes did not separate based on their forced classification, consistent with these barcodes reflecting ambient RNA mixtures that may blend multiple subpopulations. We therefore conclude that by providing a readout of sample identity that is independent of the transcriptome, cell "hashing" can help recover low-quality cells that can otherwise be difficult to distinguish from ambient RNA (FIG. 8F).

E. Methods

PBMC genotyping: Peripheral blood mononuclear cells were obtained from AllCells (USA). Genomic DNA was purified using the All-prep kit (Qiagen, USA) and genotyped using the Infinium core exome 24 array (Illumina, USA) according to manufacturer's instructions.

Cell culture: HEK293T (human) and NIH-3T3 (mouse) cells were maintained according to standard procedures in Dulbecco's Modified Eagle's Medium (Thermo Fisher, USA) supplemented with 10% fetal bovine serum (Thermo Fisher, USA) at 37° C. with 5% $CO_2$.

Antibody-oligo conjugates: Antibody-oligo conjugates directed against CD8 [clone: RPA-T8], CD45RA [clone: HI100], CD4 [clone: RPA-T4], HLA-DR [clone: L243], CD3 [clone: UCHT1], CCR7 [clone: G043H7] and PD-1 [clone: EH12.2H7] were provided by BioLegend (USA) containing 1-2 conjugated oligos per antibody on average.

Antibodies used for cell hashing were obtained as purified, unconjugated reagents from BioLegend (CD45 [clone: HI30], CD98 [clone: MEM-108], CD44 [clone: BJ18], and CD11a [clone: HI111]) and were covalently and irreversibly conjugated to HTOs by iEDDA-click chemistry as previously described[45]. In short, antibodies were washed into 1× borate buffered saline (50 mM borate, 150 mM NaCl pH 8.5) and concentrated to 1 mg/ml using an Amicon Ultra 0.5 ml 30 kDa MWCO centrifugal filter (Millipore). Methyltetrazine-PEG4-NHS ester (Click Chemistry Tools, USA) was dissolved in dry DMSO and added as a 30-fold excess to the antibody and allowed to react for 30 minutes at room temperature. Residual NHS groups were quenched by the addition of glycine and unreacted label was removed via centrifugal filtration. 5'-amine HTOs were ordered from Integrated DNA Technologies (USA) and reacted with a 20-fold excess of trans-cyclooctene-PEG4-NHS (Click Chemistry Tools, USA) in 1× borate buffered saline supplemented with 20% DMSO for 30 minutes. Residual NHS groups were quenched by the addition of glycine and residual label was removed by desalting (Bio-Rad Micro Bio-Spin P6). Antibody-oligo conjugates were formed by mixing the appropriate labeled antibody and HTO and incubating at room temperature for at least 1 hour. Residual methyltetrazine groups on the antibody were quenched by the addition of trans-cyclooctene-PEG4-acid and unreacted oligo was removed centrifugal filtration using an Amicon Ultra 0.5 ml 50 kDa MWCO filter (Millipore, USA).

Antibody Titration Series: To test optimal concentration of Antibody-Oligo conjugates provided by BioLegend (USA) per CITE-seq experiment, we tested 5 μg, 3 μg, 1 μg, 0.5 μg, 0.25 μg, 0.06 μg and 0 μg for each conjugate. Titrations were staggered over the different batches to keep the total concentration of antibodies and oligos consistent between conditions (see Table 4 below).

TABLE 4

|  | Donor A | Donor B | Donor C | Donor D | Donor E | Donor F | Donor G | Donor H |
|---|---|---|---|---|---|---|---|---|
| CD8 | 5 | 3 | 1 | 0.5 | 0.25 | 0.06 | 0 | 0 |
| PD.1 | 3 | 1 | 0.5 | 0.25 | 0.06 | 0 | 5 | 0 |
| CCR7 | 1 | 0.5 | 0.25 | 0.06 | 0 | 5 | 3 | 0 |
| CD3 | 0.5 | 0.25 | 0.06 | 0 | 5 | 3 | 1 | 0 |
| HLA.DR | 0.25 | 0.06 | 0 | 5 | 3 | 1 | 0.5 | 0 |
| CD4 | 0.06 | 0 | 5 | 3 | 1 | 0.5 | 0.25 | 0 |
| CD45RA | 0 | 5 | 3 | 1 | 0.5 | 0.25 | 0.06 | 0 |

Sample pooling: PBMCs from different donors were independently stained with one of our HTO-conjugated antibody pools and a pool of 7 immunophenotypic markers for CITE-seq at different amounts (see above). All eight PBMC samples were pooled at equal concentration, alongside unlabeled HEK293T and mouse 3T3 as negative controls and loaded into the 10× Chromium instrument (see Table 5 below).

TABLE 5

| Sample in pool | Labeled with Hashtag# | HTO Barcode | SEQ ID NO: | # cells loaded | Est. Cell yield |
|---|---|---|---|---|---|
| PBMC donor A | A | AGGACCATCCAA | 26 | ~3.5K | ~2.5K |
| PBMC donor B | B | ACATGTTACCGT | 27 | ~3.5K | ~2.5K |
| PBMC donor C | C | AGCTTACTATCC | 28 | ~3.5K | ~2.5K |
| PBMC donor D | D | TCGATAATGCGA | 29 | ~3.5K | ~2.5K |
| PBMC donor E | E | GAGGCTGAGCTA | 30 | ~3.5K | ~2.5K |
| PBMC donor F | F | GTGTGACGTATT | 31 | ~3.5K | ~2.5K |
| PBMC donor G | G | ACTGTCTAACGG | 32 | ~3.5K | ~2.5K |
| PBMC donor H | H | TATCACATCGGT | 33 | ~3.5K | ~2.5K |
| HEK293T | — | — |  | ~3.5K | ~2.5K |
| NIH-3T3 | — | — |  | ~0.8K | ~0.5K |

CITE-seq on 10× Genomics instrument: Cells were "stained" with hashtagging antibodies and CITE-seq antibodies as described for CITE-seq[46]. "Stained" and washed cells were loaded into 10× Genomics single cell 3' v2 workflow and processed according to manufacturer's instructions up until the cDNA amplification step (10× Genomics, USA). 2 pmol of HTO and ADT additive oligonucleotides were spiked into the cDNA amplification PCR and cDNA was amplified according to the 10× Single Cell 3' v2 protocol (10× Genomics, USA). Following PCR, 0.6×SPRI was used to separate the large cDNA fraction derived from cellular mRNAs (retained on beads) from the ADT- and hashtag-containing fraction (in supernatant). The cDNA fraction was processed according to the 10× Genomics Single Cell 3' v2 protocol to generate the transcriptome library. An additional 1.4× reaction volume of SPRI beads was added to the ADT/hashtag fraction to bring the ratio up to 2.0×. Beads were washed with 80% ethanol, eluted in water, and an additional round of 2.0×SPRI performed to remove excess single-stranded oligonucleotides from cDNA amplification. After final elution, separate PCRs were set up to generate the CITEseq ADT library (SI-PCR and RPI-x primers), and the hashtag library (SI-PCR and D7xx_s). A detailed and regularly updated point-by-point protocol for CITE-seq, cell-hashtagging, and future updates can be found at www.cite-seq.com.

TABLE 6

| Oligo Name | Sequence | SEQ ID NO: |
|---|---|---|
| hashtag oligo: /5AmMC12/ | GTGACTGGAGTTCAGACGTGTGCTCTTCCGATCTnnnnnnnnnnnnBAAAAAAAAAAAAAAAAAAAAAAAAAAAAAA | 34 |
| HTO additive: | GTGACTGGAGTTCAGACGTGTGC*T*C | 35 |
| ADT additive | CCTTGGCACCCGAGAATT*C*C | 36 |
| SI-PCR | AATGATACGGCGACCACCGAGATCTACACTCTTTCCCTACACGACGC*T*C | 37 |
| RPI-x | CAAGCAGAAGACGGCATACGAGATnnnnnnnnGTGACTGGAGTTCCTTGGCACCCGAGAATTC*C*A | 38 |
| D7xx_s | CAAGCAGAAGACGGCATACGAGATnnnnnnnnGTGACTGGAGTTCAGACGTGT*G*C | 39 | n: Barcode or index sequence and can be A, T, G or C
B: T,G,C, not A
*Phosphorothioate bond Single-cell data processing: Fastq files from the 10× libraries with four distinct barcodes were pooled together and processed using the standard Drop-seq pipeline (Drop-seq tools v1.0, McCarroll Lab). Reads were aligned to the hg19-mm10 concatenated reference, and we included the top 50,000 cell barcodes in the raw digital expression matrix as output from Drop-seq tools. For ADT and HTO quantification, we implemented our previously developed tag quantification pipeline[46] as a python script, available on the web at github.com/Hoohm/CITE-seq-Count, and run with default parameters (maximum hamming distance of 1).

Demultiplexing with genotyping data using demuxlet: We first generated a VCF file that contained the individual genotype (GT) from the Infinium core exome 24 array output, using the PLINK command line tools (version 1.07). This VCF file (which contained genotype information for the 8 PBMC donors as well as HEK cells), and the tagged bam file from Drop-seq pipeline were used as inputs for demuxlet[71], with default parameters.

Single-cell RNA data processing: Normalization and downstream analysis of RNA data were performed using the Seurat R package (version 2.1, Satija Lab) which enables the integrated processing of multi-modal (RNA, ADT, HTO) single cell datasets[78,79]. We collapsed the joint-species RNA expression matrix to only include the top 100 most highly expressed mouse genes (along with all human genes) using the CollapseSpeciesExpressionMatrix function.

We first considered a set of 22,119 barcodes where we detected at least 200 UMI in the transcriptome data. Since the HEK and 3T3 cells were not labeled with HTOs, we identified these cells based on their transcriptomes. We performed a low-resolution pre-clustering by performing PCA on the 500 most highly expressed genes, followed by Louvain-Jaccard clustering on a distance matrix based on the first five principal components[58,80,81] Based on this clustering, we identified 248 3T3 cells and 3,401 HEK cells, with the remainder representing PBMCs.

As a separate test of HEK identity, we examined the demuxlet genotype for possible HEK cells. We observed 1,668 barcodes classified as HEK by the demuxlet algorithm, but whose transcriptomes clustered with PBMCs. These cells expressed ten-fold fewer UMI compared to transcriptomically-classified HEK cells, and did not express HEK-specific transcripts (i.e. NGFRAP1), both consistent with a PBMC identity. We therefore excluded these barcodes from all further analysis.

Classification of barcodes based on HTO levels: HTO raw counts were normalized using centered log ratio (CLR) transformation, where counts were divided by the geometric mean of an HTO across cells, and log-transformed:

$$x'_i = \log \frac{x_i}{\left(\prod_{i=1}^{n} x_i\right)^{1/n}}$$

Here $x_i$ denotes the count for a specified HTO in cell i, n is the total cell number, log denotes the natural log. Pairwise analysis of either normalized or raw HTO counts (FIG. 6B) revealed mutually exclusive relationships, though determining the exact cutoffs for positive and negative signals required further analysis. We reasoned that if we could determine a background distribution for each HTO based on 'negative' cells, outliers from this distribution would represent positive signals.

To assist in the unsupervised identification of "negative" cells, we performed an initial k-medoids clustering for all cells based on the normalized HTO data. We set k=9, and observed (as expected) that eight of the clusters were highly enriched for expression of a particular HTO, while the ninth cluster was highly enriched for cells with low expression of all HTO. This represents an initial solution to the demultiplexing problem that suggests likely populations of "positive" and "negative" cells for statistical analysis.

Following clustering, we performed the following procedure independently for each of the 8 HTOs. We identified the k-medoids cluster with the highest average HTO expression, and excluded these cells. We next fit a negative binomial distribution to the remaining HTO values, after further excluding the highest 0.5% values as potential outliers. We calculated the q=0.99 quantile of the fitted distribution, and thresholded each cell in the dataset based on this HTO-specific value.

We used this procedure to determine an "HTO classification" for each barcode. Barcodes that were positive for only one HTO were classified as singlets. Barcodes that were positive for two or more HTO were classified as doublets, and assigned sample IDs based on their two most highly expressed HTO. Barcodes that were negative for all eight HTO were classified as "negative".

We expect that barcodes classified as "singlets" represent single cells, as we detect only a single HTO. However, they could also represent doublets of a PBMC with a HEK or 3T3 cell, as the latter two populations were unlabeled and represent negative controls. Indeed, when we analyzed the "HTO classification" of cells that were transcriptomically annotated as HEK or 3T3 cells, we found that 73.4% were annotated as "negative", while 29.2% were annotated as singlets, in complete agreement with expected ratios in our "super-loaded" 10× experiment. These cells appear in the heatmap in FIG. 6C, but all HEK and 3T3 cells were excluded from further analysis.

Figure 1D:
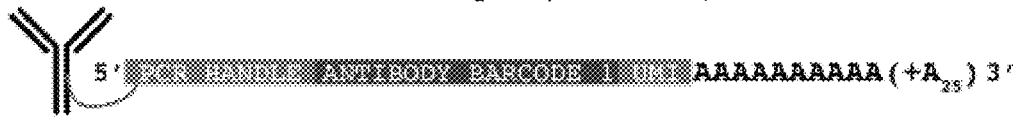
FIG. 1D is an illustration showing an embodiment of a construct described herein in which antibodies (ligands) are linked to a polymer construct containing functional sequence components (Amplification Handle and PCR handle) and a unique antibody identifier Barcode followed by a polyA tail (Anchor).
Figure 1D:
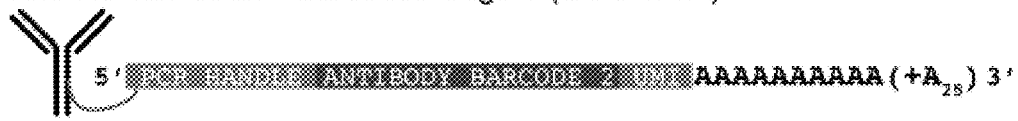

For two-dimensional visualization of HTO levels (FIG. 1D), we used Euclidean distances calculated from the normalized HTO data as inputs for tSNE. Cells are colored based on their HTO classification as previously described. For visualization and clustering based on transcriptomic data (FIG. 6F), we first performed PCA on the 2,000 most highly variable genes (as determined by variance/mean ratio), and used the distance matrix defined by the first 11 principal components as input to tSNE and graph-based clustering in Seurat (FIG. 6E). We annotated the nine clusters based on canonical markers for known hematopoietic populations.

Comparison with demuxlet: Demuxlet classifications were labeled as singlets (SNG), doublets (DBL) or ambiguous (AMB) according to the BEST column in the *.best output file. In FIG. 7E, we plot the posterior probability of a doublet assignment, from the PRB.DBL column in the same file.

Calculation of staining index for antibody titrations: To assess the optimal staining efficiency for CITE-seq experiments, we considered ADT levels for cells across a range of antibody concentrations, as multiplexed in a titration series. ADT levels were normalized using a CLR transformation of raw counts, using an identical approach to the normalization of HTO levels as previously described.

After normalization, we computed a staining index based on standard approaches in flow cytometry, which examine the difference between positive and negative peak medians, divided by the spread (i.e. twice the mean absolute deviation) of the negative peak.

$$SI = \frac{Pos_{0.5} - Neg_{0.5}}{*mad\ (Neg)}$$

In order to avoid manual classification of positive and negative peaks, we implemented an automated procedure that can scale to multiple antibodies and concentrations. To approximate the negative peak, we leveraged unstained control cells (Donor H). To approximate the positive peak, we clustered the ADT data in each titration experiment (Donor A through Donor G). To perform clustering, we computed a Euclidean distance matrix across cells based on normalized ADT levels, and used this as input to the FindClusters function in Seurat with default parameters. We examined the results to identify the cluster with the maximally enriched ADT signal, and referred to the distribution of ADT levels within this cluster as the positive peak.

Discriminating low-quality cells from ambient RNA: We performed HTO classification of low-quality barcodes (expressing between 50 and 200 UMI), using the previously determined HTO thresholds. For each barcode, we classified its expression as one of our previously determined nine hematopoietic populations using random forests, as implemented in the ranger package in R27. We first trained a classifier on the 13,757 PBMCs, using the 2,000 most variable genes as input, and their clustering identities as training labels. We then applied this classifier to each of the low-quality barcodes. We note that this classifier is guaranteed to return a result for each barcode.

This process described in Example 10 was used for droplet-based approaches, but is also applicable to microwell based approaches.

Combinatorial split-pool hashtagging can be used to increase the number of barcodes and thereby increase doublet detection capability. The Hashtagging approach is inherent in in-situ barcoding approaches (SPLiT-seq, sci-RNAseq) if the first round of barcoding defines different conditions or samples. In contrast to demuxlet, this approach can be used to multiplex samples of the same genotype. No need to perform genotyping on sample. This process can be extended to barcoding nuclei.

Here, we introduce a new method for scRNA-seq multiplexing, where cells are labeled with sample-specific "hashtags" for downstream demultiplexing and doublet detection. Our approach is complementary to pioneering genetic multiplexing strategies, with each having unique advantages. Genetic multiplexing does not utilize exogenous barcodes, and therefore does not require alterations to existing workflows prior to or after sample pooling. In contrast, cell "hashing" requires incubation with antibodies against ubiquitously expressed surface proteins, but can multiplex samples with the same genotype. Both methods do slightly increase downstream sequencing costs, due to increased depth or read length needed to identify SNPs (genetic approaches), or sequencing of HTO libraries (cell "hashing"; approximately 5% of transcriptome sequencing costs). We believe that researchers will benefit from both approaches, enabling multiplexing for a broad range of experimental designs. In particular, we envision that our method will be most useful when processing genetically identical samples subjected to diverse perturbations (or experimental conditions/optimizations, as in our titration experiment), or to reduce the doublet rate when running cells from a single sample.

By enabling the robust identification of cell multiplets, both cell "hashing" and genetic multiplexing allow the "super loading" of scRNA-seq platforms. We demonstrate this in the context of the 10× Genomics Chromium system, but this benefit applies to any single-cell technology that relies on Poisson loading for cell isolation. The per-cell cost savings for library preparation can therefore be significant, approaching an order of magnitude as the number of multiplexed samples increases. Notably, cell "hashing" enables even a single sample to be highly multiplexed, as cells can be split into an arbitrary number of pools. As clearly discussed in Kang et al[71], savings in library prep are partially offset by reads originating from multiplets, which must be sequenced and discarded. Still, as sequencing costs continue to drop, and experimental designs seek to minimize technology-driven batch effects, multiplexing should facilitate the generation of large scRNA-seq and CITE-seq datasets. Informatic detection of multiplets based on transcriptomic data also remains an important challenge for the field, for example, to identify doublets originating from two cells within the same sample.

In our current study, we used a pool of antibodies directed against highly and ubiquitously expressed lymphocyte surface proteins as the vehicle for our HTOs. This strategy aimed to mitigate the possibility that stochastic or cell-type variation in expression of any one marker would introduce bias in HTO recovery. Going forward, we expect a more universal pool of antibodies directed against ubiquitously expressed markers to be used as a universal cell "hashing" reagent for studies beyond the hematopoietic system. With the increasing interest in single nucleus sequencing[76], an additional set of "hashing" reagents directed against nuclear proteins would further generalize this approach. Beyond antibody/epitope interactions, cell or nucleus, including other protein:protein interactions, aptamers[77], or direct chemical conjugation of oligos to cells or nuclei. These improvements will further enable multiplexing strategies to generalize to diverse experiments regardless of species, tissue, or technology.

Each and every patent, patent application, and publication, including websites cited throughout the specification, and sequence identified in the specification, are incorporated herein by reference. U.S. Provisional Patent Application Nos. 62/609,332 filed on Dec. 21, 2017; 62/599,450 filed on Dec. 15, 2017; 62/559,228 filed on Sep. 15, 2017; 62/549,189 filed on Aug. 23, 2017; 62/515,180 filed on Jun. 5, 2017; and 62/453,726 filed on Feb. 2, 2017, are all incorporated herein by reference, including all text, tables, drawings, sequences and sequence listings. While the invention has been described with reference to particular embodiments, it will be appreciated that modifications can be made without departing from the spirit of the invention. Such modifications are intended to fall within the scope of the appended claims.

The following information in Table 7 is provided for sequences containing free text under numeric identifier <223>.

TABLE 7

| (Sequence Listing Free Text) | |
| --- | --- |
| SEQ ID NO: | Free text under <223> |
| 1 | <221> misc_feature<br><222> (41) . . . (42)<br><223> n is a or g or c or t/u |

TABLE 7-continued (Sequence Listing Free Text)

| SEQ ID NO: | Free text under <223> |
|---|---|
| 2 | <221> misc_feature<br><222> (41) . . . (42)<br><223> n is a or g or c or t/u |
| 3 | <221> misc_feature<br><222> (40) . . . (41)<br><223> n is a or g or c or t/u |
| 4 | <221> misc_feature<br><222> (40) . . . (41)<br><223> n is a or g or c or t/u |
| 5 | <223> Synthetic oligonucleotide sequence for CBMC profiling |
| 6 | <223> Synthetic oligonucleotide sequence for CMBC profiling |
| 7 | <223> Synthetic oligonucleotide sequence for CMBC profiling |
| 8 | <223> Synthetic oligonucleotide sequence for CMBC profiling |
| 9 | <223> Synthetic oligonucleotide sequence for CMBC profiling |
| 10 | <223> Synthetic oligonucleotide sequence for CBMC profiling |
| 11 | <223> Synthetic oligonucleotide sequence for CMBC profiling |
| 12 | <223> Synthetic oligonucleotide sequence for CMBC profiling |
| 13 | <223> Synthetic oligonucleotide sequence for CMBC profiling |
| 14 | <223> Synthetic oligonucleotide sequence for CMBC profiling |
| 15 | <223> Synthetic oligonucleotide sequence for CBMC profiling |
| 16 | <223> Synthetic oligonucleotide sequence for CMBC profiling |
| 17 | <223> Synthetic oligonucleotide sequence for CMBC profiling |
| 18 | <223> Synthetic oligonucleotide sequence amplification handle |
| 19 | <223> Synthetic oligonucleotide sequence amplification handle |
| 20 | <223> Synthetic barcode sequence |
| 21 | <223> Synthetic barcode sequence |
| 22 | <223> Synthetic barcode sequence |
| 23 | <223> Synthetic barcode sequence |
| 24 | <223> Synthetic barcode sequence |
| 25 | <223> Synthetic barcode sequence |
| 26 | <223> Synthetic barcode sequence |
| 27 | <223> Synthetic barcode sequence |
| 28 | <223> Synthetic barcode sequence |
| 29 | <223> Synthetic barcode sequence |
| 30 | <223> Synthetic barcode sequence |
| 31 | <223> Synthetic barcode sequence |
| 32 | <223> Synthetic barcode sequence |
| 33 | <223> Synthetic barcode sequence |
| 34 | <223> Synthetic hashtag oligonucleotide sequence |
| 35 | <223> synthetic oligonucleotide sequence of a hashtag additive<br><221> misc_feature<br><222> (23) . . . (24)<br><223> Bases modified by presence of phosphorothioate bond |
| 36 | <223> Synthetic ADT additive oligonucleotide sequence<br><220><br><221> misc_feature<br><222> (18) . . . (19)<br><223> Bases modified by phosphorothioate bond |
| 37 | <223> Synthetic PCR oligonucleotide sequence<br><220><br><221> misc_feature<br><222> (47) . . . (48)<br><223> Bases modified by phosphorothioate bond |
| 38 | <223> Synthetic oligonucleotide sequenc<br><220><br><221> misc_feature<br><222> (25) . . . (32)<br><223> n is A, T, G, or C from a barcode or index sequence<br><220><br><221> misc_feature<br><222> (63) . . . (64)<br><223> Bases modified by phosphorothioate bond |
| 39 | <223> Synthetic sequences forming a hashtag library of primers<br><220><br><221> misc_feature<br><222> (25) . . . (32)<br><223> n is A or C or T or G forming a barcode or index sequence<br><220><br><221> misc_feature<br><222> (53) . . . (54)<br><223> Bases modified by phosphorothioate bond |

REFERENCES

1. Macosko, E. Z. et al. Highly Parallel Genome-wide Expression Profiling of Individual Cells Using Nanoliter Droplets. *CELL* 161, 1202-1214 (2015).
2. Klein, A. M. et al. Droplet Barcoding for Single-Cell Transcriptomics Applied to Embryonic Stem Cells. *CELL* 161, 1187-1201 (2015).
3. Zheng, G. X. Y. et al. Massively parallel digital transcriptional profiling of single cells. *bioRxiv* 1-46 (Cold Spring Harbor Labs Journals, 2016). doi:10.1101/065912; also, Nat. Commun. 8, 1-12 (2017); doi: 10.1038/ncomms14049 (2017).
4. Schwanhäusser, B. et al. Global quantification of mammalian gene expression control. *Nature* 473, 337-342 (2011).
5. Grun, D. et al. Conservation of mRNA and Protein Expression during Development of *C. elegans*. *Cell Reports* 6, 565-577 (2014).
6. Stoeckius, M. et al. Global characterization of the oocyte-to-embryo transition in *Caenorhabditis elegans* uncovers a novel mRNA clearance mechanism. *The EMBO Journal* 33, 1751-1766 (2014).
7. Pontén, F. et al. A global view of protein expression in human cells, tissues, and organs. *Mol Syst Biol* 5, 337 (2009).
8. Paul, F. et al. Transcriptional Heterogeneity and Lineage Commitment in Myeloid Progenitors. *CELL* 163, 1663-1677 (2015).
9. Wilson, N. K. et al. Combined Single-Cell Functional and Gene Expression Analysis Resolves Heterogeneity within Stem Cell Populations. *CELL STEM CELL* 16, 712-724 (2015).
10. Stahlberg, A. et al. Quantitative PCR analysis of DNA, RNAs, and proteins in the same single cell. *Clinical Chemistry* 58, 1682-1691 (2012).
11. Genshaft, A. S. et al. Multiplexed, targeted profiling of single-cell proteomes and transcriptomes in a single reaction. *Genome Biol.* 17:188 (2016). doi:10.1186/s13059-016-1045-6
12. Albayrak, C. et al. Digital Quantification of Proteins and mRNA in Single Mammalian Cells. *Molecular Cell* 61, 914-924 (2016).
13. Darmanis, S. et al. Simultaneous Multiplexed Measurement of RNA and Proteins in Single Cells. *Cell Reports* 14, 380-389 (2016).
14. Frei, A. P. et al. Highly multiplexed simultaneous detection of RNAs and proteins in single cells. *Nature Methods* 13, 269-275 (2016).
15. Sano, T., et al. Immuno-PCR: very sensitive antigen detection by means of specific antibody-DNA conjugates. *SCIENCE-NEW YORK THEN* . . . (1992).
16. Gullberg, M. et al. A sense of closeness: protein detection by proximity ligation. *Current Opinion in Biotechnology* 14, 82-86 (2003).
17. Chattopadhyay, P. K. & Roederer, M. Cytometry: Today's technology and tomorrow's horizons. *Methods* 57, 251-258 (2012).
18. Bendall, S. C. & Nolan, G. P. From single cells to deep phenotypes in cancer. *Nat Biotechnol* 1-9 (2012). doi: 10.1038/nbt.2283
19. Adler, M., et al. Sensitivity by combination: Immuno-PCR and related technologies. *Analyst* 133, 702-18 (2008).
20. Cao, Junyue, et al. Comprehensive single cell transcriptional profiling of a multicellular organism by combinatorial indexing. *Sci.*, 357(6352):661-667 (2017).
21. Bendall, S. C. & Nolan, G. P. From single cells to deep phenotypes in cancer. *Nat Biotechnol* 1-9 (2012).
22. Baumgarth, N., Roederer, M. A practical approach to multicolor flow cytometry for immunophenotyping. *J Immunol Methods* 243, 77-97 (2000)
23. Mortazavi et al. Mapping and quantifying mammalian transcriptomes by RNA-seq. *Nature Methods* 5, 621-628 (2008)
24. Hermanson, G. T. Bioconjugation Techniques. $2^{nd}$ Edition. *Academic Press*, San Diego, CA (2008)
25. Lizardi, P. M., et al. Mutation detection and single-molecule counting using isothermal rolling-circle amplification. *Nat Genet.* 1998; 19:225-232.
26. Assarsson, E., et al. Homogenous 96-plex PEA immunoassay exhibiting high sensitivity, specificity, and excellent scalability. *PLOS ONE.* 2014; 9:e95192.
27. Fakruddin, M D, et al. "Nucleic acid amplification: Alternative methods of polymerase chain reaction." *Journal of Pharmacy and Bioallied Sciences* 5.4 (2013): 245.
28. Nimse, S B et al. Immobilization techniques for microarray: challenges and applications. Sensors 14.12 (2014): 22208-22229.
29. Heise, C. and Bier, F F. Immobilization of DNA on microarrays. Immobilization of DNA on Chips II. Springer Berlin Heidelberg, 2005. 1-25.
30. Rosenberg, Alexander B., et al. Scaling single cell transcriptomics through split pool barcoding. bioRxiv (2017): 105163
31. Li, Zhenhua, et al. DNA nanostructure-based universal microarray platform for high-efficiency multiplex bioanalysis in biofluids. ACS applied materials & interfaces 6(20) (2014): 17944-17953
32. Zhao, Hong, et al. Cell fixation in zinc salt solution is compatible with DNA damage response detection by phospho-specific antibodies. Cytometry Part A 79.6 (2011): 470-476.
33. Iglesias-Ussel, Maria, Luigi Marchionni, and Fabio Romerio. Isolation of microarray-quality RNA from primary human cells after intracellular immunostaining and fluorescence-activated cell sorting. Journal of Immunological Methods 391.1 (2013): 22-30.
34. L. J. P. van der Maaten and G. E. Hinton. Visualizing High-Dimensional Data Using t-SNE. Journal of Machine Learning Research 9 (November 2008):2579-2605
35. Gierahn T M, et al, Seq-Well: portable, low-cost RNA sequencing of single cells at high throughput. *Nat. Methods*, 2017 April, 14(4):395-398 (epub 2017 Feb. 13)
36. Crosetto, Nicola, Magda Bienko, and Alexander Van Oudenaarden. Spatially resolved transcriptomics and beyond. *Nature Reviews Genetics* 16.1 (2015): 57-66
37. Leah Cannon, Single Cell Analysis: A Mini-Report, lifesciencenetwork.com/blogs/leah-cannon/2017/03/21/single-cell-analysis-a-mini-report, 2017 March
38. Zhang, Kai, et al. Single-cell isolation by a modular single-cell pipette for RNA-sequencing. Lab on a Chip 16.24 (2016): 4742-4748;
39. Poulin, Jean-Francois, et al. Disentangling neural cell diversity using single-cell transcriptomics. Nature neuroscience 19.9 (2016): 1131-1141
40. Picelli, Simone. Single-cell RNA-sequencing: The future of genome biology is now. RNA biology (2016): 1-14)
41. Lai, Shujing, et al. Mapping Human Hematopoietic Hierarchy At Single Cell Resolution By Microwell-seq. bioRxiv (2017): 127217

42. Xin, Yurong, et al. Use of the Fluidigm C1 platform for RNA sequencing of single mouse pancreatic islet cells. *Proceedings of the National Academy of Sciences* (2016): 201602306
43. Islam, Saiful, et al. Quantitative single-cell RNA-seq with unique molecular identifiers. *Nature methods* 11.2 (2014): 163-166
44. Wu, Angela R., et al. Quantitative assessment of single-cell RNA-sequencing methods. *Nature methods* 11.1 (2014): 41-46
45. van Buggenum, MAGL et al., A covalent and cleavable antibody-DNA conjugation strategy for sensitive protein detection via immuno-PCR, *Sci. Reports,* 6:22675, DOI: 10.1038/srep22675
46. Stoeckius M, et al., Simultaneous epitope and transcriptome measurement in single cells 31 Jul. 2017, *Nature Methods* 9, 2579-10 (2017). DOI:10.1038/NMeth.4380
47. Murphy, K., Travers, P. & Walport, M. Janeway's Immunobiology 7th edn (Garland Publishing, 2008).
48. Robinson, J. P. & Roederer, M., Flow Cytometry Strikes Gold, *Science* 350, 739-740 (2015).
49. Fan, H. C., Fu, G. K. & Fodor, S. P. A., Combinatorial labeling of single cells for gene expression cytometry, *Science* 347, 1258367 (2015).
50. Poli, A. et al., $CD^{56}$bright natural killer (NK) cells: an important NK cell subset, Immunology 126, 458-465 (2009).
51. Ferlazzo, G. & Münz, C. J., NK Cell Compartments and Their Activation by Dendritic Cells, *Immunol.* 172, 1333-1339 (2004).
52. Wendt, K. et al., Gene and protein characteristics reflect functional diversity of $CD^{56}$dim and $CD^{56}$bright NK cells., *J. Leukoc. Biol.* 80, 1529-1541 (2006).
53. Shahi, P., Kim, S. C., Haliburton, J. R., Gartner, Z. J. & Abate, A. R., Abseq: Ultrahigh-throughput single cell protein profiling with droplet microfluidic barcoding, *Sci. Rep.* 7, 44447 (2017).
54. Yuan, J. & Sims, P. A. An Automated Microwell Platform for Large-Scale Single Cell RNA-Seq. *Sci. Rep.* 6, 33883 (2016).
55. Gierahn, T. M. et al. Seq-Well: portable, low-cost RNA sequencing of single cells at high throughput, *Nat. Methods* 14, 395-398 (2017).
56. Baranauskas, A. et al. Generation and characterization of new highly thermostable and processive M-MuLV reverse transcriptase variants, *Protein Eng. Des. Sel.* 25, 657-668 (2012).
57. Breton, G., Lee, J., Liu, K. & Nussenzweig, M. C. Defining human dendritic cell progenitors by multiparametric flow cytometry, *Nat. Protoc.* 10, 1407-1422 (2015).
58. Blondel, V. D., et al. Fast unfolding of communities in large networks, *J. Stat. Mech.* 2008, P10008 (2008).
59. van der Maaten, L. *J. Mach. Learn. Res.* 15, 1-21 (2014).
60. Stoeckius, M. & Smibert, Cite-seq, Protocol Exchange http://dx.doi.org/10.1038/protex.2017.068 (31 Jul. 2017).
61. Aitchison, J., Measures of location of compositional data sets., *Math. Geol.* 21(7): 787-790 (1989).
62. Kang, H. M. et al., Multiplexing droplet-based single cell RNA-sequencing using natural genetic barcodes, bioRxiv 118778; doi: https://doi.org/10.1101/118778
63. Stubbington, M. J. T., Rozenblatt-Rosen, O., Regev, A. & Teichmann, S. A. Single-cell transcriptomics to explore the immune system in health and disease. *Science* 358, 58-63 (2017).
64. Tanay, A. & Regev, A. Scaling single-cell genomics from phenomenology to mechanism. *Nature* 541, 331-338 (2017).
65. Villani, A.-C. et al. Single-cell RNA-seq reveals new types of human blood dendritic cells, monocytes, and progenitors. *Science* 356, (2017).
66. Velten, L. et al. Human haematopoietic stem cell lineage commitment is a continuous process. *Nature Cell Biology* 19, 271-281 (2017).
67. Karaiskos, N. et al. The *Drosophila* embryo at single-cell transcriptome resolution. *Science* 8, eaan3235-14 (2017).
68. Regev, A. et al. Science Forum: The Human Cell Atlas. *eLife* 6, e27041 (2017).
69. Stegle, O., Teichmann, S. A. & Marioni, J. C. Computational and analytical challenges in single-cell transcriptomics. *Nature Publishing Group* 16, 133-145 (2015).
70. Hicks, S. C., et al. Missing data and technical variability in single-cell RNA-sequencing experiments. *Biostatistics* (2017). doi:10.1093/biostatistics/kxx053
71. Kang, H. M. et al. Multiplexed droplet single-cell RNA-sequencing using natural genetic variation. *Nature Biotechnology* (2017). doi:10.1038/nbt.4042
72. Tung, P.-Y. et al. Batch effects and the effective design of single-cell gene expression studies. *Scientific Reports* 7, 39921 (2017).
73. Krutzik, P. O. & Nolan, G. P. Fluorescent cell barcoding in flow cytometry allows highthroughput drug screening and signaling profiling. *Nat Meth* 3, 361-368 (2006).
74. Lai, L., Ong, R., Li, J. & Albani, S. A CD45-based barcoding approach to multiplex masscytometry (CyTOF). *Cytometry* 87, 369-374 (2015).
75. Hulspas, R. Titration of fluorochrome-conjugated antibodies for labeling cell surface markers on live cells. *Curr Protoc Cytom* Chapter 6, Unit 6.29 (2010).
76. Lake, B. B. et al. A comparative strategy for single-nucleus and single-cell transcriptomes confirms accuracy in predicted cell-type expression from nuclear RNA. *Scientific Reports* 1-8 (2017). doi:10.1038/s41598-017-04426-w
77. Delley, C. L., liu, L., Sarhan, M. F. & Abate, A. R. Combined aptamer and transcriptome sequencing of single cells. bioRxiv 1-10 (2017). doi:10.1101/228338
78. Satija, R., Farrell, J. A., Gennert, D., Schier, A. F. & Regev, A. Spatial reconstruction of single-cell gene expression data. Nature Biotechnology 33, 495-502 (2015).
79. Butler, A. & Satija, R. Integrated analysis of single cell transcriptomic data across conditions, technologies, and species. bioRxiv (2017). doi:10.1101/164889
80. Levine, J. H. et al. Data-Driven Phenotypic Dissection of AML Reveals Progenitor-like Cells that Correlate with Prognosis. *Cell* 162, 184-197 (2015).
81. Shekhar, K. et al. Comprehensive Classification of Retinal Bipolar Neurons by Single-Cell Transcriptomics. *Cell* 166, 1308-1323.e30 (2016).
82. Wright, M. N. & Ziegler, A. ranger: A Fast Implementation of Random Forests for High Dimensional Data in C and R. *Journal of Statistical Software* 77, (2017).

The invention claimed is:

1. A method of simultaneously identifying from a single sequencing run a transcriptome and one or more proteins on one or more cells which comprise cellular mRNA, the method comprising:
- a) providing the one or more cells originating from a biological sample, wherein each of the one or more cells comprises one or more epitopes, and each of the one or more epitopes corresponds to one of the one or more proteins on the one or more cells;
- b) generating one or more complexes, wherein each of the one or more generated complexes comprises:
  - (i) one of the one or more cells;
  - (ii) a first construct comprising:
    - (a) a first antibody or fragment thereof that specifically binds to a first of the one or more epitopes; and,
    - (b) a first construct oligonucleotide, the first construct oligonucleotide conjugated to the first antibody or fragment thereof by a linker, wherein the first construct oligonucleotide comprises:
      - (i) an amplification handle;
      - (ii) a first antibody barcode sequence that specifically identifies said first antibody or fragment thereof from any other antibody or fragment thereof that recognizes a different epitope of the one or more epitopes; and,
      - (iii) an anchor sequence;

and,
  - (iii) one or more distinct additional constructs, each distinct additional construct comprising:
    - (a) an additional antibody or fragment thereof that specifically binds to an additional epitope of the one or more epitopes; and,
    - (b) an additional construct oligonucleotide, wherein each additional construct oligonucleotide is conjugated to the additional antibody or fragment thereof by a linker, wherein each of the additional construct oligonucleotides comprises:
      - (i) an amplification handle;
      - (ii) an additional antibody barcode sequence that specifically identifies said additional antibody or fragment thereof from any other antibody or fragment that recognizes a different epitope of the one or more epitopes; and,
      - (iii) an anchor sequence,
    wherein each of the additional one or more epitopes is different from the first epitope and the additional epitope of the one or more epitopes of the other distinct additional constructs, and each of the distinct additional constructs differs from the corresponding components of the first construct and the other distinct additional constructs by the additional antibody or fragment thereof and the additional antibody barcode sequence;
- c) individually partitioning each of the generated one or more complexes with a bead, each bead conjugated to capture oligonucleotides that comprise:
  - (i) sequences that hybridize to the anchor sequences; and,
  - (ii) a bead-specific barcode sequence unique to each bead;
- d) lysing the one or more cells to release:
  - (i) the first construct;
  - (ii) the one or more distinct additional constructs; and,
  - (iii) the cellular mRNA present in the one or more cells;
- e) annealing:
  - (i) the cellular mRNA to the capture oligonucleotides; and,
  - (ii) the first construct oligonucleotide and the additional construct oligonucleotides to the capture oligonucleotides;
- f) generating:
  - (i) cDNA from the annealed cellular mRNA and the capture oligonucleotides; and
  - (ii) DNA from the annealed first construct oligonucleotide, the additional construct oligonucleotides, and the capture oligonucleotides;
- g) substantially separating by size:
  - (i) the cDNA generated from the annealed cellular mRNA and the capture oligonucleotides; and,
  - (ii) the DNA generated from the annealed first construct oligonucleotide, the additional construct oligonucleotides, and the capture oligonucleotides;
- h) generating, independently from each other:
  - (i) a transcriptome amplification library comprising cDNAs amplified from the cDNAs generated from the annealed cellular mRNA and the capture oligonucleotides; and,
  - (ii) a protein amplification library comprising DNAs amplified from the DNAs generated from the annealed first construct oligonucleotide, the additional construct oligonucleotides, and the capture oligonucleotides;
- i) pooling the transcriptome amplification library and the protein amplification library after they are generated;
- j) sequencing, in parallel, the pooled transcriptome amplification library and the protein amplification library, in a single sequencing run; and,
- k) from the parallel sequencing, using the antibody barcode sequences and the bead-specific barcode sequences to simultaneously identify the transcriptome and the one or more proteins on the one or more cells.

2. The method of claim 1, wherein the cDNA from step (g) comprises fragments of greater than 300 nucleotides in length, and the DNA from step (g) comprises fragments of less than 300 nucleotides in length.

3. The method of claim 1, wherein the one or more distinct additional constructs of step (b) comprises at least 100 or more distinct additional constructs.

4. The method of claim 1, wherein after step (b) the one or more cells are washed.

5. The method of claim 1, wherein the linker comprises a cleavable covalent bond.

6. The method of claim 5, wherein the cleavable covalent bond comprises a disulfide bond.

7. The method of claim 1, further comprising: assigning a biological sample of origin to each of the one or more cells.

8. The method of claim 1, wherein the anchor sequence is a polyA anchor sequence and the capture oligonucleotides are polyT capture oligonucleotides.

* * * * *

SEQUENCE LISTING

<160> NUMBER OF SEQ ID NOS: 39

<210> SEQ ID NO 1
<211> LENGTH: 78
<212> TYPE: DNA
<213> ORGANISM: Artificial Sequence
<220> FEATURE:
<223> OTHER INFORMATION: Synthetic reagent sequence for analytic
      procedure
<220> FEATURE:
<221> NAME/KEY: misc_feature
<222> LOCATION: (41)..(42)
<223> OTHER INFORMATION: n is a or g or c or t/u

<400> SEQUENCE: 1
gtctcgtggg ctcggagatg tgtataagag acaggccaat nnbaaaaaaa aaaaaaaaaa    60
aaaaaaaaaa aaaaaaaa                                                  78

<210> SEQ ID NO 2
<211> LENGTH: 78
<212> TYPE: DNA
<213> ORGANISM: artificial sequence
<220> FEATURE:
<223> OTHER INFORMATION: Unique molecular identifier - random sequence
<220> FEATURE:
<221> NAME/KEY: misc_feature
<222> LOCATION: (41)..(42)
<223> OTHER INFORMATION: n is a or g or c or t/u

<400> SEQUENCE: 2
gtctcgtggg ctcggagatg tgtataagag acagcttgta nnbaaaaaaa aaaaaaaaaa    60
aaaaaaaaaa aaaaaaaa                                                  78

<210> SEQ ID NO 3
<211> LENGTH: 77
<212> TYPE: DNA
<213> ORGANISM: Artificial Sequence
<220> FEATURE:
<223> OTHER INFORMATION: Unique molecular identifier-random sequence
<220> FEATURE:
<221> NAME/KEY: misc_feature
<222> LOCATION: (40)..(41)
<223> OTHER INFORMATION: n is a or g or c or t/u

<400> SEQUENCE: 3
tcgtcggcag cgtcagatgt gtataagaga caggccaatn nbaaaaaaaa aaaaaaaaaa    60
aaaaaaaaaa aaaaaaa                                                   77

<210> SEQ ID NO 4
<211> LENGTH: 77
<212> TYPE: DNA
<213> ORGANISM: Artificial Sequence
<220> FEATURE:
<223> OTHER INFORMATION: Unique molecular sequence - random
<220> FEATURE:
<221> NAME/KEY: misc_feature
<222> LOCATION: (40)..(41)
<223> OTHER INFORMATION: n is a or g or c or t/u

<400> SEQUENCE: 4
tcgtcggcag cgtcagatgt gtataagaga cagcttgtan nbaaaaaaaa aaaaaaaaaa    60
aaaaaaaaaa aaaaaaa                                                   77

<210> SEQ ID NO 5
<211> LENGTH: 60
<212> TYPE: DNA

```
<213> ORGANISM: Artificial Sequence
<220> FEATURE:
<223> OTHER INFORMATION: Synthetic oligonucleotide sequence for CBMC
      profiling

<400> SEQUENCE: 5
ccttggcacc cgagaattcc aatcacgbaa aaaaaaaaaa aaaaaaaaaa aaaaaaaaaa    60

<210> SEQ ID NO 6
<211> LENGTH: 60
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 6
ccttggcacc cgagaattcc acgatgtbaa aaaaaaaaaa aaaaaaaaaa aaaaaaaaaa    60

<210> SEQ ID NO 7
<211> LENGTH: 59
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 7
ccttggcacc gagaattcca ttaggcbaaa aaaaaaaaaa aaaaaaaaaa aaaaaaaaa     59

<210> SEQ ID NO 8
<211> LENGTH: 60
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 8
ccttggcacc cgagaattcc atgaccabaa aaaaaaaaaa aaaaaaaaaa aaaaaaaaaa    60

<210> SEQ ID NO 9
<211> LENGTH: 60
<212> TYPE: DNA
<213> ORGANISM: Artificial Sequence
<220> FEATURE:
<223> OTHER INFORMATION: Synthetic oligonucleotide sequence for CBMC
      profiling

<400> SEQUENCE: 9
ccttggcacc cgagaattcc agccaatbaa aaaaaaaaaa aaaaaaaaaa aaaaaaaaaa    60

<210> SEQ ID NO 10
<211> LENGTH: 60
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 10
ccttggcacc cgagaattcc agatcagbaa aaaaaaaaaa aaaaaaaaaa aaaaaaaaaa    60

<210> SEQ ID NO 11
<211> LENGTH: 60
<212> TYPE: DNA
<213> ORGANISM: Artificial Sequence
```

```
<220> FEATURE:
<223> OTHER INFORMATION: Synthetic oligonucleotide sequence for CMBC
      profiling

<400> SEQUENCE: 11
ccttggcacc cgagaattcc atagcttbaa aaaaaaaaa aaaaaaaaa aaaaaaaaa            60

<210> SEQ ID NO 12
<211> LENGTH: 60
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 12
ccttggcacc cgagaattcc acttgtabaa aaaaaaaaa aaaaaaaaa aaaaaaaaa            60

<210> SEQ ID NO 13
<211> LENGTH: 60
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 13
ccttggcacc cgagaattcc aacttgabaa aaaaaaaaa aaaaaaaaa aaaaaaaaa            60

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 14
ccttggcacc cgagaattcc aggctacbaa aaaaaaaaa aaaaaaaaa aaaaaaaaa            60

<210> SEQ ID NO 15
<211> LENGTH: 60
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 15
ccttggcacc cgagaattcc aagtcaabaa aaaaaaaaa aaaaaaaaa aaaaaaaaa            60

<210> SEQ ID NO 16
<211> LENGTH: 57
<212> TYPE: DNA
<213> ORGANISM: Artificial Sequence
<220> FEATURE:
<223> OTHER INFORMATION: Synthetic oligonucleotide sequence for CMBC
      profiling

<400> SEQUENCE: 16
ccttggcacc cgagaattcc aagttccbaa aaaaaaaaa aaaaaaaaa aaaaaa               57

<210> SEQ ID NO 17
<211> LENGTH: 63
<212> TYPE: DNA
<213> ORGANISM: Artificial Sequence
<220> FEATURE:
```

```
<223> OTHER INFORMATION: Synthetic oligonucleotide sequence for CMBC
      profiling

<400> SEQUENCE: 17
ccttggcacc cgagaattcc aacagtgbaa aaaaaaaaaa aaaaaaaaaa aaaaaaaaaa      60
aaa                                                                   63

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide sequence
      amplification handle

<400> SEQUENCE: 18
ccttggcacc cgagaattcc a                                               21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide sequence
      amplification handle

<400> SEQUENCE: 19
ccttggcacc cgagaattcc a                                               21

<210> SEQ ID NO 20
<211> LENGTH: 10
<212> TYPE: DNA
<213> ORGANISM: Artificial Sequence
<220> FEATURE:
<223> OTHER INFORMATION: Synthetic barcode sequence

<400> SEQUENCE: 20
ttcgtgaggt                                                            10

<210> SEQ ID NO 21
<211> LENGTH: 10
<212> TYPE: DNA
<213> ORGANISM: Artificial Sequence
<220> FEATURE:
<223> OTHER INFORMATION: Synthetic barcode sequence

<400> SEQUENCE: 21
tcttcgtcca                                                            10

<210> SEQ ID NO 22
<211> LENGTH: 10
<212> TYPE: DNA
<213> ORGANISM: Artificial Sequence
<220> FEATURE:
<223> OTHER INFORMATION: Synthetic barcode sequence

<400> SEQUENCE: 22
atgctctacc                                                            10

<210> SEQ ID NO 23
<211> LENGTH: 10
<212> TYPE: DNA
<213> ORGANISM: Artificial Sequence
<220> FEATURE:
<223> OTHER INFORMATION: Synthetic barcode sequence
```

```
<400> SEQUENCE: 23
tagacagctg                                                          10

<210> SEQ ID NO 24
<211> LENGTH: 10
<212> TYPE: DNA
<213> ORGANISM: Artificial Sequence
<220> FEATURE:
<223> OTHER INFORMATION: Synthetic barcode sequence

<400> SEQUENCE: 24
atggaggtag                                                          10

<210> SEQ ID NO 25
<211> LENGTH: 10
<212> TYPE: DNA
<213> ORGANISM: Artificial Sequence
<220> FEATURE:
<223> OTHER INFORMATION: Synthetic barcode sequence

<400> SEQUENCE: 25
agatgaaccc                                                          10

<210> SEQ ID NO 26
<211> LENGTH: 12
<212> TYPE: DNA
<213> ORGANISM: Artificial Sequence
<220> FEATURE:
<223> OTHER INFORMATION: Synthetic barcode sequence

<400> SEQUENCE: 26
aggaccatcc aa                                                       12

<210> SEQ ID NO 27
<211> LENGTH: 12
<212> TYPE: DNA
<213> ORGANISM: Artificial Sequence
<220> FEATURE:
<223> OTHER INFORMATION: Synthetic barcode sequence

<400> SEQUENCE: 27
acatgttacc gt                                                       12

<210> SEQ ID NO 28
<211> LENGTH: 12
<212> TYPE: DNA
<213> ORGANISM: Artificial Sequence
<220> FEATURE:
<223> OTHER INFORMATION: Synthetic barcode sequence

<400> SEQUENCE: 28
agcttactat cc                                                       12

<210> SEQ ID NO 29
<211> LENGTH: 12
<212> TYPE: DNA
<213> ORGANISM: Artificial Sequence
<220> FEATURE:
<223> OTHER INFORMATION: Synthetic barcode sequence

<400> SEQUENCE: 29
tcgataatgc ga                                                       12

<210> SEQ ID NO 30
<211> LENGTH: 12
```

```
<212> TYPE: DNA
<213> ORGANISM: Artificial Sequence
<220> FEATURE:
<223> OTHER INFORMATION: Synthetic barcode sequence

<400> SEQUENCE: 30
gaggctgagc ta                                                          12

<210> SEQ ID NO 31
<211> LENGTH: 12
<212> TYPE: DNA
<213> ORGANISM: Artificial Sequence
<220> FEATURE:
<223> OTHER INFORMATION: Synthetic barcode sequence

<400> SEQUENCE: 31
gtgtgacgta tt                                                          12

<210> SEQ ID NO 32
<211> LENGTH: 12
<212> TYPE: DNA
<213> ORGANISM: Artificial Sequence
<220> FEATURE:
<223> OTHER INFORMATION: Synthetic barcode sequence

<400> SEQUENCE: 32
actgtctaac gg                                                          12

<210> SEQ ID NO 33
<211> LENGTH: 12
<212> TYPE: DNA
<213> ORGANISM: Artificial Sequence
<220> FEATURE:
<223> OTHER INFORMATION: Synthetic barcode sequence

<400> SEQUENCE: 33
tatcacatcg gt                                                          12

<210> SEQ ID NO 34
<211> LENGTH: 79
<212> TYPE: DNA
<213> ORGANISM: Artificial Sequence
<220> FEATURE:
<223> OTHER INFORMATION: Synthetic hashtag oligonucleotide sequence
<220> FEATURE:
<221> NAME/KEY: misc_feature
<222> LOCATION: (35)..(46)
<223> OTHER INFORMATION: n is a, t, c, g from a barcode or index
      sequence

<400> SEQUENCE: 34
gtgactggag ttcagacgtg tgctcttccg atctnnnnnn nnnnnnbaaa aaaaaaaaa       60 aaaaaaaaaa aaaaaaaa                                                    79

<210> SEQ ID NO 35
<211> LENGTH: 25
<212> TYPE: DNA
<213> ORGANISM: Artificial Sequence
<220> FEATURE:
<223> OTHER INFORMATION: synthetic oligonucleotide sequence of a hashtag
      additive
<220> FEATURE:
<221> NAME/KEY: misc_feature
<222> LOCATION: (23)..(24)
<223> OTHER INFORMATION: Bases modified by presence of phosphorothioate
      bond

<400> SEQUENCE: 35
```
gtgactggag ttcagacgtg tgctc                                          25

<210> SEQ ID NO 36
<211> LENGTH: 20
<212> TYPE: DNA
<213> ORGANISM: Artificial Sequence
<220> FEATURE:
<223> OTHER INFORMATION: Synthetic ADT additive oligonucleotide sequence
<220> FEATURE:
<221> NAME/KEY: misc_feature
<222> LOCATION: (18)..(19)
<223> OTHER INFORMATION: Bases modified by phosphorothioate bond

<400> SEQUENCE: 36
ccttggcacc cgagaattcc                                                20

<210> SEQ ID NO 37
<211> LENGTH: 49
<212> TYPE: DNA
<213> ORGANISM: Artificial Sequence
<220> FEATURE:
<223> OTHER INFORMATION: Synthetic PCR oligonucleotide sequence
<220> FEATURE:
<221> NAME/KEY: misc_feature
<222> LOCATION: (47)..(48)
<223> OTHER INFORMATION: Bases modified by phosphorothioate bond

<400> SEQUENCE: 37
aatgatacgg cgaccaccga gatctacact ctttccctac acgacgctc                49

<210> SEQ ID NO 38
<211> LENGTH: 65
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: misc_feature
<222> LOCATION: (25)..(32)
<223> OTHER INFORMATION: n is A, T, G, or C from a barcode or index
      sequence
<220> FEATURE:
<221> NAME/KEY: misc_feature
<222> LOCATION: (63)..(64)
<223> OTHER INFORMATION: Bases modified by phosphorothioate bond

<400> SEQUENCE: 38
caagcagaag acggcatacg agatnnnnnn nngtgactgg agttccttgg cacccgagaa    60
ttcca                                                                65

<210> SEQ ID NO 39
<211> LENGTH: 55
<212> TYPE: DNA
<213> ORGANISM: Artificial Sequence
<220> FEATURE:
<223> OTHER INFORMATION: Synthetic sequences forming a hashtag library
      of primers
<220> FEATURE:
<221> NAME/KEY: misc_feature
<222> LOCATION: (25)..(32)
<223> OTHER INFORMATION: n is A or C or T or G forming a barcode or
      index sequence
<220> FEATURE:
<221> NAME/KEY: misc_feature
<222> LOCATION: (53)..(54)
<223> OTHER INFORMATION: Bases modified by phosphorothioate bond

```
<400> SEQUENCE: 39
caagcagaag acggcatacg agatnnnnnn nngtgactgg agttcagacg tgtgc        55
```